US012807696B2

(12) United States Patent
Rommelaere et al.

(10) Patent No.: US 12,807,696 B2
(45) Date of Patent: Nov. 24, 2026

(54) POLYPEPTIDES COMPRISING IMMUNOGLOBULIN SINGLE VARIABLE DOMAINS TARGETING TNFα AND IL-23

(71) Applicants: Ablynx N.V., Zwijnaarde (BE); Sanofi, Paris (FR)

(72) Inventors: Heidi Rommelaere, Ghent (BE); Christian Asbrand, Frankfurt am Main (DE); Ann Brigé, Ertvelde (BE); Sigrid Cornelis, St. Martens-Latem (BE); Eric Lorent, Zwijnaarde (BE)

(73) Assignees: Ablynx NV, Zwijnaarde (BE); Sanofi, Paris (FR)

( * ) Notice: Subject to any disclaimer, the term of this patent is extended or adjusted under 35 U.S.C. 154(b) by 1249 days.

(21) Appl. No.: 17/727,868

(22) Filed: Apr. 25, 2022

(65) Prior Publication Data

US 2022/0372128 A1 Nov. 24, 2022

Related U.S. Application Data

(60) Division of application No. 17/502,332, filed on Oct. 15, 2021, now Pat. No. 11,332,525, which is a continuation of application No. 17/111,689, filed on Dec. 4, 2020, now abandoned.

(60) Provisional application No. 62/944,619, filed on Dec. 6, 2019.

(30) Foreign Application Priority Data

Jan. 23, 2020 (EP) .................................... 20305056
Feb. 28, 2020 (EP) .................................... 20000090
Mar. 2, 2020 (EP) .................................... 20305216

(51) Int. Cl.
*A61K 39/395* (2006.01)
*A61P 17/00* (2006.01)
*A61P 19/02* (2006.01)
*A61P 37/06* (2006.01)
*C07K 16/18* (2006.01)
*C07K 16/24* (2006.01)
*A61K 39/00* (2006.01)

(52) U.S. Cl.
CPC .......... *C07K 16/244* (2013.01); *A61K 39/395* (2013.01); *A61P 17/00* (2018.01); *A61P 19/02* (2018.01); *A61P 37/06* (2018.01); *C07K 16/18* (2013.01); *C07K 16/241* (2013.01); *A61K 2039/505* (2013.01); *C07K 2317/31* (2013.01); *C07K 2317/565* (2013.01); *C07K 2317/569* (2013.01); *C07K 2317/76* (2013.01); *C07K 2317/92* (2013.01)

(58) Field of Classification Search
CPC ................ C07K 16/241; C07K 16/244; C07K 2039/505; C07K 2317/31; C07K 2317/569; C07K 2319/00; A61K 39/395
See application file for complete search history.

(56) References Cited

U.S. PATENT DOCUMENTS

| | | | |
|---|---|---|---|
| 11,332,525 | B2 | 5/2022 | Rommelaere et al. |
| 2016/0122429 | A1 | 5/2016 | Millican et al. |
| 2021/0188963 | A1 | 6/2021 | Rommelaere et al. |
| 2022/0363747 | A1 | 11/2022 | Rommelaere et al. |

FOREIGN PATENT DOCUMENTS

| | | | |
|---|---|---|---|
| CN | 101970490 | A | 2/2011 |
| CN | 106661100 | A | 5/2017 |
| CN | 108473563 | A | 8/2018 |
| JP | 2017-533705 | A | 11/2017 |
| WO | WO 2009/068627 | A2 | 6/2009 |
| WO | WO 2015/173325 | A2 | 11/2015 |
| WO | WO 2016/073406 | A1 | 5/2016 |
| WO | WO 2017/068186 | A1 | 4/2017 |
| WO | WO 2017/081320 | A1 | 5/2017 |
| WO | WO 2017/137579 | A1 | 8/2017 |
| WO | WO 2019/027780 | A1 | 2/2019 |

OTHER PUBLICATIONS

Phan et al., Intest. Res., 2020, vol. 18(3):282-288.*
Knappik et al., J. Mol. Biol., 2000, vol. 296(1):57-86.*
Rudikoff et al., Proc. Natl. Acad. Sci, USA, 1982, vol. 79:1979-1983.*
Rabia et al., Biochem. Eng. J., 2018, vol. 137:365-374.*
[No Author Listed], Nanobodies as a versatile and clinically validated approach for multi-specifics. Ablynx N.V.. IBC next Generation Protein Therapeutics Conference. May 20, 2015. 37 pages.
Bannas et al., Nanobodies and Nanobody-Based Human Heavy Chain Antibodies as Antitumor Therapeutics. Front Immunol. Nov. 22, 2017;8:1603. doi: 10.3389/fimmu.2017.01603.
Chanier et al., Nanobody Engineering: Toward Next Generation Immunotherapies and Immunoimaging of Cancer. Antibodies (Basel). Jan. 21, 2019;8(1):13. doi: 10.3390/antib8010013.
Morrison, Nanobody approval gives domain antibodies a boost. Nat Rev Drug Discov. Jul. 2019;18(7):485-487. doi: 10.1038/d41573-019-00104-w.
Rudikoff et al., Single amino acid substitution altering antigen-binding specificity. Proc Natl Acad Sci U S A. Mar. 1982;79(6):1979-83. doi: 10.1073/pnas.79.6.1979.

(Continued)

*Primary Examiner* — Xiaozhen Xie

(74) *Attorney, Agent, or Firm* — Wolf, Greenfield & Sacks, P.C.

(57) ABSTRACT

The present technology aims at providing a novel type of drug. Specifically, the present technology provides polypeptides comprising at least three immunoglobulin single variable domains (ISVDs), characterized in that at least one ISVD binds to TNFα and at least two ISVDs bind to IL-23. The present technology also provides nucleic acids, vectors and compositions.

20 Claims, 16 Drawing Sheets

Figure 1:
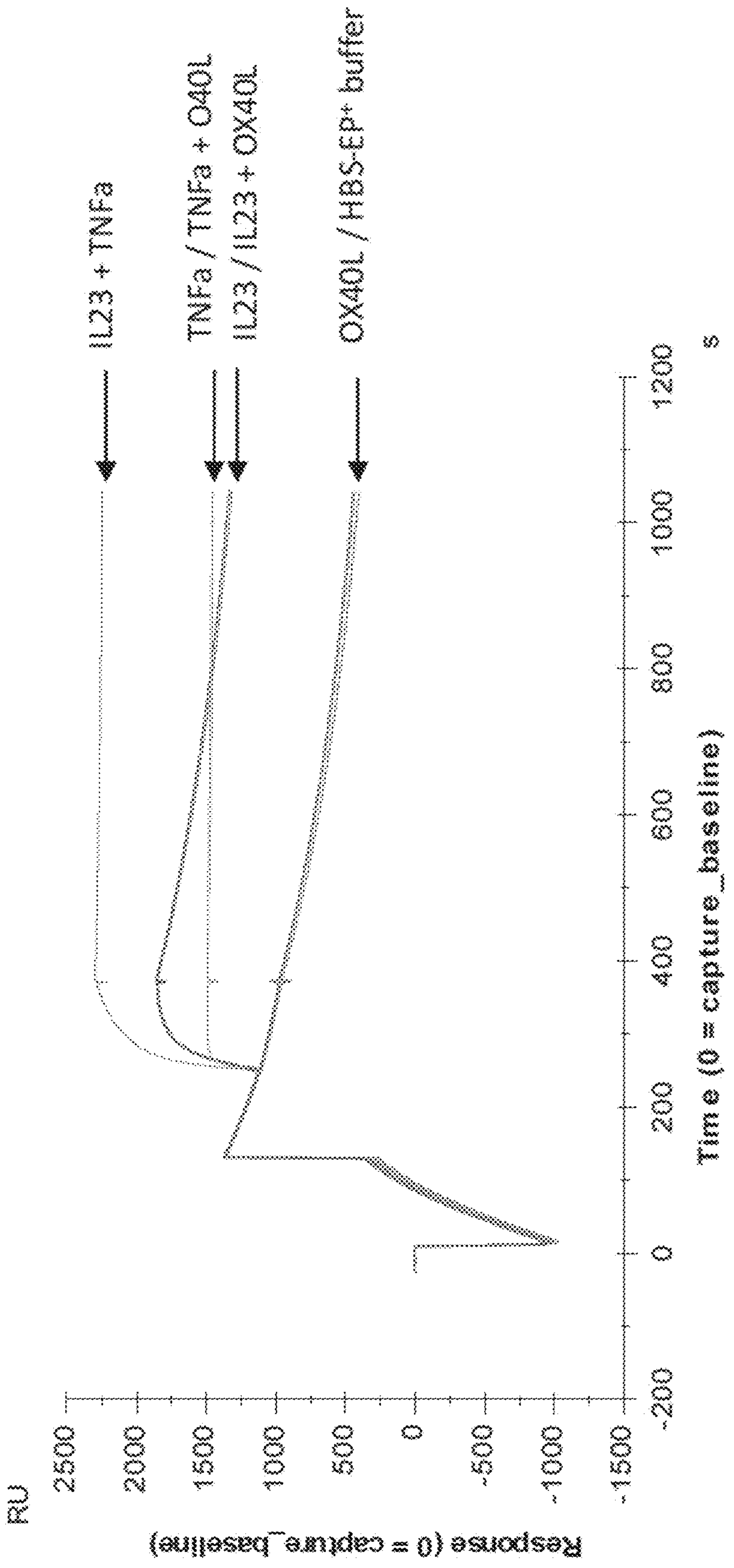

Specification includes a Sequence Listing.

(56) References Cited

OTHER PUBLICATIONS

Kitsis et al., Discordance between gene regulation in vitro and in vivo. Gene Expr. 1992;2(4):313-8.

* cited by examiner

| Bonferroni multiple comparisons test | week 7 | | week 8 | | week 9 | | week 10 | | week 11 | |
|---|---|---|---|---|---|---|---|---|---|---|
| Human IgG1 vs F027500069 1.3mg/kg | ** | 0.0037 | * | 0.0395 | * | 0.0481 | * | 0.0212 | ns | 0.9646 |
| Human IgG1 vs F027500069 4mg/kg | * | 0.0191 | ns | 0.1424 | * | 0.0278 | ns | 0.3645 | ns | 0.0927 |
| Human IgG1 vs F027500069 13.5mg/kg | ** | 0.0052 | ** | 0.0014 | ** | 0.0047 | ** | 0.0014 | *** | 0.0003 |
| Human IgG1 vs anti-hTNFα reference mAb 10mg/kg | ** | 0.0023 | *** | 0.0002 | *** | 0.0004 | *** | 0.0002 | *** | 0.0001 |

| Bonferroni multiple comparisons test | Adjusted P value | |
|---|---|---|
| Human IgG1 vs F027500069 1.3mg/kg | ** | 0.0043 |
| Human IgG1 vs F027500069 4mg/kg | ** | 0.0074 |
| Human IgG1 vs F027500069 13.5mg/kg | **** | <0.0001 |
| Human IgG1 vs anti-hTNFα reference mAb 10mg/kg | **** | <0.0001 |

| Bonferroni multiple comparisons test | Adjusted P value | |
|---|---|---|
| Human IgG1 vs F027500069 1.3mg/kg | ns | 0.1951 |
| Human IgG1 vs F027500069 4mg/kg | * | 0.012 |
| Human IgG1 vs F027500069 13.5mg/kg | **** | <0.0001 |
| Human IgG1 vs anti-hTNFα reference mAb 10mg/kg | **** | <0.0001 |

| Bonferroni multiple comparisons test | Adjusted P value | |
|---|---|---|
| PBS [-IL23] vs Human IgG1 ctrl 3mg/kg | * | 0.024 |
| Human IgG1 vs F027500069 0.13mg/kg | ns | >0.9999 |
| Human IgG1 vs F027500069 0.4mg/kg | ns | 0.6531 |
| Human IgG1 vs F027500069 1mg/kg | ns | 0.2667 |
| Human IgG1 vs F027500069 4mg/kg | * | 0.0253 |
| Human IgG1 vs anti-hIL-23 reference mAb1 3mg/kg | ns | >0.9999 |

| Bonferroni multiple comparisons test | Adjusted P value | |
|---|---|---|
| Human IgG1 vs F027500069 0.13mg/kg | **** | <0.0001 |
| Human IgG1 vs F027500069 0.4mg/kg | **** | <0.0001 |
| Human IgG1 vs F027500069 1mg/kg | Not assessed | |
| Human IgG1 vs F027500069 4mg/kg | **** | <0.0001 |
| Human IgG1 vs anti-hIL-23 reference mAb1 3mg/kg | **** | <0.0001 |

| Bonferroni multiple comparisons test | Adjusted P value | |
|---|---|---|
| PBS [-IL23] vs NAb ctrl 1 mg/kg | **** | <0.0001 |
| NAb ctrl vs F027500069 0.1 mg/kg IP | *** | 0.0005 |
| NAb ctrl vs F027500069 1 mg/kg IP | **** | <0.0001 |
| NAb ctrl vs F027500069 0.1 mg/kg SC | * | 0.0107 |
| NAb ctrl vs F027500069 1 mg/kg SC | **** | <0.0001 |
| NAb ctrl vs anti-hIL-23 reference mAb1 3mg/kg | **** | <0.0001 |
| F027500069 0.1 mg/kg IP vs SC | ns | >0.9999 |
| F027500069 1 mg/kg IP vs SC | ns | >0.9999 |

| Bonferroni multiple comparisons test | Adjusted P value | |
|---|---|---|
| PBS (-IL23) vs NAb ctrl 1 mg/kg | ** | 0.0048 |
| NAb ctrl vs F027500069 0.1 mg/kg IP | *** | 0.001 |
| NAb ctrl vs F027500069 1 mg/kg IP | **** | <0.0001 |
| NAb ctrl vs F027500069 0.1 mg/kg SC | *** | 0.0005 |
| NAb ctrl vs F027500069 1 mg/kg SC | **** | <0.0001 |
| NAb ctrl vs anti-hIL-23 reference mAb1 3mg/kg | *** | 0.0006 |
| F027500069 0.1 mg/kg IP vs SC | ns | >0.9999 |
| F027500069 1 mg/kg IP vs SC | ns | >0.9999 |

| Bonferroni multiple comparisons test | day 3 | | day 4 | | day 5 | | day 6 | | day 7 | |
|---|---|---|---|---|---|---|---|---|---|---|
| Vehicle ctrl vs F027500069 1.3mg/kg | ns | 0.6577 | ns | 0.1694 | ns | 0.0908 | ns | 0.0751 | * | 0.0404 |
| Vehicle ctrl vs anti-hTNFα reference mAb 0.5mg/kg | ns | 0.3713 | ns | 0.1945 | ns | 0.0621 | ns | 0.0524 | * | 0.0453 |

| Bonferroni multiple comparisons test | Adjusted P value | |
|---|---|---|
| NAb ctrl 1 mg/kg vs. F027500101 0.1 mg/kg | * | 0.0115 |
| NAb ctrl 1 mg/kg vs. F027500017 0.15 mg/kg | **** | <0.0001 |
| NAb ctrl 1 mg/kg vs. F027500069 0.2 mg/kg | **** | <0.0001 |
| F027500101 0.1 mg/kg vs. F027500069 0.2 mg/kg | ** | 0.0091 |
| F027500017 0.15 mg/kg vs. F027500069 0.2 mg/kg | ns | 0.557 |

POLYPEPTIDES COMPRISING IMMUNOGLOBULIN SINGLE VARIABLE DOMAINS TARGETING TNFα AND IL-23

RELATED APPLICATIONS

This application is a divisional of U.S. application Ser. No. 17/502,332, filed Oct. 15, 2021, now U.S. Pat. No. 11,332,525, which is a continuation of U.S. application Ser. No. 17/111,689, filed Dec. 4, 2020, now abandoned, which claims the benefit under 35 U.S.C. § 119 (e) of U.S. provisional application Ser. No. 62/944,619, filed Dec. 6, 2019, the entire content of each of which is incorporated by reference herein.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Apr. 19, 2022, is named A084870213US03-SEQ-JRV, and is 51,891 bytes in size.

DESCRIPTION

Field of the Present Technology

The present technology relates to polypeptides targeting TNFα and the p19 subunit of IL-23. It also relates to nucleic acid molecules encoding the polypeptide and vectors comprising the nucleic acids, and to compositions comprising the polypeptide, nucleic acid or vector. The present technology further relates to these products for use in a method of treating a subject suffering from inflammatory bowel disease, psoriasis, psoriatic arthritis or Hidradenitis suppurativa. Moreover, the present technology relates to methods of producing these products.

Technological Background

Autoimmune or inflammatory diseases are the result of an immune response produced by a body against its own tissue. Autoimmune or inflammatory diseases are often chronic and can even be life-threatening. Amongst others, autoimmune or inflammatory diseases include inflammatory bowel disease, such as Crohn's disease and ulcerative colitis, psoriasis, psoriatic arthritis and hidradenitis suppurativa. Inflammatory bowel disease, such as Crohn's disease and ulcerative colitis, is a chronic inflammatory disease involving intestinal inflammation and concomitant epithelial injury. Other chronic autoimmune diseases, such as psoriasis, psoriatic arthritis and hidradenitis suppurativa, are characterized by patches of red, dry, itchy or scaly skin, painful inflammation of joints or inflamed and swollen lumps on the skin. It has been found that patients suffering from psoriasis are more likely to have certain comorbidities, including diabetes and inflammatory bowel disease, such as Crohn's disease or ulcerative colitis, and cancer.

Interleukin 23 (IL-23) is a cytokine important in the activation of various immune cells during induction of chronic inflammation. IL-23 is an upstream regulator of cytokines IL-6, IL-17, GM-CSF and IL-22, and is a heterodimer consisting of a p19 subunit (IL-23 alpha subunit, also referred to herein as IL-23p19) covalently linked to a p40 subunit (the p40 subunit is shared with cytokine IL-12 and is also called IL-12 beta subunit). In addition, IL-23 plays an important role in T-cell inflammatory immune response as well as in the regulation of inflammatory activity of innate lymphoid cells. IL-23 has been implicated with inflammatory diseases including inflammatory bowel disease and other autoimmune diseases.

Tumor Necrosis Factor alpha (TNFα) is a homotrimeric cytokine which is produced mainly by monocytes and macrophages, but also known to be secreted by $CD4^+$ and $CD8^+$ peripheral blood T lymphocytes. TNFα can exist as a soluble form or as a transmembrane protein. The primary role of TNFα is in the regulation of immune cells. TNFα acts as an endogenous pyrogen and dysregulation of its production has been implicated in a variety of human diseases including inflammatory bowel disease and other autoimmune diseases, such as psoriasis.

Treatments currently approved by the FDA for inflammatory bowel disease include anti-TNFα biologicals (such as Simponi® [golimumab], Enbrel® [etanercept], Remicade® [infliximab] and Humira® [adalimumab]). However, current anti-TNFα treatments for inflammatory bowel disease face a large percentage of patients being non-responsive to currently available treatments, and loss of response to anti-TNFα treatment occurs in a high percentage of patients following 12 months of treatment.

For psoriasis and psoriatic arthritis, only a minority of patients is treated with biologicals (including REMICADE® [infliximab] and HUMIRA® [adalimumab], as well as STELARA® [ustekinumab] which targets the shared p40 subunit of cytokines IL-12 and IL-23). Further antibody treatments targeting IL-23 are underway, including guselkumab (Tremfya; approved in psoriasis and in clinical trial phase 3 for inflammatory bowel disease and psoriatic arthritis) and risankizumab (Skyrizi; approved in psoriasis and in clinical trial phase 3 for psoriatic arthritis and Crohn's disease). While the class of p19-targeting anti-IL-23 antibodies could confer some disease suppressing efficacy in psoriasis, patients with different and/or additional autoimmune diseases do not necessarily profit from those treatments to the same extent. In psoriatic arthritis for example, treatment with anti-IL23 does not improve the response of the inflamed joints. In inflammatory bowel diseases, more than half of the patients do not respond or lose response to TNF inhibitors. The same holds true for hidradenitis suppurativa, for which the only approved treatment so far is HUMIRA® [adalimumab], though only about 50% of patients respond.

Targeting multiple disease factors may be achieved for example by co-administration or combinatorial use of two separate biologicals, e.g. antibodies binding to different therapeutic targets. However, co-administration or combinatorial use of separate biologicals can be challenging, both from a practical and a commercial point of view. For example, two injections of separate products result in a more inconvenient and more painful treatment regime to the patients which may negatively affect compliance. With regard to a single injection of two separate products, it can be difficult or impossible to provide formulations that allow for acceptable viscosity at the required concentrations and suitable stability of both products. Additionally, co-administration and co-formulation requires production of two separate drugs which can increase overall costs.

Bispecific antibodies that are able to bind to two different antigens have been suggested as one strategy for addressing such limitations associated with co-administration or combinatorial use of separate biologicals, such as antibodies.

Bispecific antibody constructs have been proposed in multiple formats. For example, bispecific antibody formats may involve the chemical conjugation of two antibodies or fragments thereof (Brennan, M, et al., Science, 1985. 229 (4708): p. 81-83; Glennie, M. J., et al., J Immunol, 1987. 139(7): p. 2367-2375). In certain formats, a single chain Fv (scFv) fragments binding to a specific antigen is linked to an IgG antibody binding to a separate antigen (for example, WO 2016/073406 which describes an anti-TNFα/anti-IL-23 IgG-scFv bispecific antibody). WO 2019/027780 describes a heterodimeric IgG antibody in which one pair of heavy and light chain variable region targets TNFα and the other pair of heavy and light chain variable region targets IL-23.

Disadvantages of such bispecific antibody formats include, however, high viscosity at high concentration, making e.g. subcutaneous administration challenging, and in that each binding unit requires the interaction of two variable domains for specific and high affinity binding, comprising implications on polypeptide stability and efficiency of production. Such bispecific antibody formats may also potentially lead to Chemistry, Manufacturing and Control (CMC) issues related to mispairing of the light chains or mispairing of the heavy chains.

SUMMARY OF THE PRESENT TECHNOLOGY

In some embodiments, the present technology relates to a polypeptide or construct specifically targeting TNFα and IL-23. Targeting TNFα and IL-23 at the same time leads to an increased efficiency of modulating an inflammatory response as compared to monospecific anti-TNFα or anti-IL-23 polypeptides.

Said polypeptides showed to be highly potent on TNFα and IL-23 (e.g. human and cyno TNFα and IL-23), could be efficiently produced (e.g. in microbial hosts such as *Pichia*, e.g. *P. pastoris*) and showed low viscosity at high concentrations which is advantageous and convenient for subcutaneous administration. Furthermore, such polypeptides could be shown to have limited reactivity to pre-existing antibodies in the subject to be treated (i.e. antibodies present in the subject before the first treatment with the antibody construct). In other embodiments such polypeptides exhibit a half-life in the subject to be treated that is long enough such that consecutive treatments can be conveniently spaced apart.

The polypeptide of the present technology comprises or consists of at least three immunoglobulin single variable domains (ISVDs), wherein at least one ISVD specifically binds to TNFα and at least two ISVDs specifically bind to the p19 subunit of IL-23. In one embodiment, the at least one ISVD binding to TNFα specifically binds to human TNFα and the at least two ISVDs binding to IL-23 specifically bind to the p19 subunit of human IL-23.

In one embodiment, the polypeptide further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units. For example, the binding unit can be an ISVD that binds to a (human) serum protein, such as to human serum albumin.

Also provided is a nucleic acid molecule capable of expressing the polypeptide of the present technology, a vector comprising the nucleic acid, and a composition comprising the polypeptide, nucleic acid or vector.

The polypeptide of the present technology, a composition comprising the polypeptide, and a composition comprising a nucleic acid comprising a nucleotide sequence that encodes the polypeptide can be used as a medicament. The polypeptide for use as a medicament comprises or consists of at least three immunoglobulin single variable domains (ISVDs), wherein each of said ISVDs comprises three complementarity determining regions (CDR1 to CDR3, respectively), optionally linked via one or more peptidic linkers; and wherein:

- a) a first ISVD comprises
  - i. a CDR1 that is the amino acid sequence of SEQ ID NO: 6 or an amino acid sequence with 2 or 1 amino acid difference(s) with SEQ ID NO: 6;
  - ii. a CDR2 that is the amino acid sequence of SEQ ID NO: 10 or an amino acid sequence with 2 or 1 amino acid difference(s) with SEQ ID NO: 10; and
  - iii. a CDR3 that is the amino acid sequence of SEQ ID NO: 14 or an amino acid sequence with 2 or 1 amino acid difference(s) with SEQ ID NO: 14;
- b) a second ISVD comprises
  - iv. a CDR1 that is the amino acid sequence of SEQ ID NO: 7 or an amino acid sequence with 2 or 1 amino acid difference(s) with SEQ ID NO: 7;
  - v. a CDR2 that is the amino acid sequence of SEQ ID NO: 11 or an amino acid sequence with 2 or 1 amino acid difference(s) with SEQ ID NO: 11; and
  - vi. a CDR3 that is the amino acid sequence of SEQ ID NO: 15 or an amino acid sequence with 2 or 1 amino acid difference(s) with SEQ ID NO: 15; and
- c) a third ISVD comprises
  - vii. a CDR1 that is the amino acid sequence of SEQ ID NO: 9 or an amino acid sequence with 2 or 1 amino acid difference(s) with SEQ ID NO: 9;
  - viii. a CDR2 that is the amino acid sequence of SEQ ID NO: 13 or an amino acid sequence with 2 or 1 amino acid difference(s) with SEQ ID NO: 13; and
  - ix. a CDR3 that is the amino acid sequence of SEQ ID NO: 17 or an amino acid sequence with 2 or 1 amino acid difference(s) with SEQ ID NO: 17, wherein the ISVDs are in the order starting from the N-terminus.

The composition of the present technology is for use as a medicament. The composition can be a pharmaceutical composition which further comprises at least one pharmaceutically acceptable carrier, diluent or excipient and/or adjuvant, and optionally comprises one or more further pharmaceutically active polypeptides and/or compounds.

The polypeptide as such (possibly present in a composition or possibly encoded by a nucleic acid) comprises or consists of at least three immunoglobulin single variable domains (ISVDs), wherein each of said ISVDs comprises three complementarity determining regions (CDR1 to CDR3, respectively), optionally linked via one or more peptidic linkers; and wherein:

- a) a first ISVD comprises
  - i. a CDR1 that is the amino acid sequence of SEQ ID NO: 6 or an amino acid sequence with 2 or 1 amino acid difference(s) with SEQ ID NO: 6;
  - ii. a CDR2 that is the amino acid sequence of SEQ ID NO: 10 or an amino acid sequence with 2 or 1 amino acid difference(s) with SEQ ID NO: 10; and
  - iii. a CDR3 that is the amino acid sequence of SEQ ID NO: 14 or an amino acid sequence with 2 or 1 amino acid difference(s) with SEQ ID NO: 14;
- b) a second ISVD comprises
  - iv. a CDR1 that is the amino acid sequence of SEQ ID NO: 7 or an amino acid sequence with 2 or 1 amino acid difference(s) with SEQ ID NO: 7;

v. a CDR2 that is the amino acid sequence of SEQ ID NO: 11 or an amino acid sequence with 2 or 1 amino acid difference(s) with SEQ ID NO: 11; and vi. a CDR3 that is the amino acid sequence of SEQ ID NO: 15 or an amino acid sequence with 2 or 1 amino acid difference(s) with SEQ ID NO: 15; and c) a third ISVD comprises vii. a CDR1 that is the amino acid sequence of SEQ ID NO: 9 or an amino acid sequence with 2 or 1 amino acid difference(s) with SEQ ID NO: 9;

viii. a CDR2 that is the amino acid sequence of SEQ ID NO: 13 or an amino acid sequence with 2 or 1 amino acid difference(s) with SEQ ID NO: 13; and ix. a CDR3 that is the amino acid sequence of SEQ ID NO: 17 or an amino acid sequence with 2 or 1 amino acid difference(s) with SEQ ID NO: 17, wherein the ISVDs are in the order starting from the N-terminus.

In one embodiment, the polypeptide specifically binds TNFα and the p19 subunit of IL-23. In one embodiment, the polypeptide specifically binds human TNFα and the p19 subunit of human IL-23. In one embodiment, the first ISVD present in the polypeptide specifically binds to TNFα and the second and third ISVDs present in the polypeptide specifically bind to the p19 subunit of IL-23. In one embodiment, the first ISVD present in the polypeptide specifically binds to human TNFα and the second and third ISVDs present in the polypeptide specifically bind to the p19 subunit of human IL-23.

The Polypeptide of the Present Technology May Comprise:

a) a first ISVD comprising a CDR1 that is the amino acid sequence of SEQ ID NO: 6, a CDR2 that is the amino acid sequence of SEQ ID NO: 10 and a CDR3 that is the amino acid sequence of SEQ ID NO: 14;

b) a second ISVD comprising a CDR1 that is the amino acid sequence of SEQ ID NO: 7, a CDR2 that is the amino acid sequence of SEQ ID NO: 11 and a CDR3 that is the amino acid sequence of SEQ ID NO: 15; and c) a third ISVD comprising a CDR1 that is the amino acid sequence of SEQ ID NO: 9, a CDR2 that is the amino acid sequence of SEQ ID NO: 13 and a CDR3 that is the amino acid sequence of SEQ ID NO: 17.

The Polypeptide of the Present Technology May Comprise:

a) a first ISVD that has an amino acid sequence comprising a sequence identity of more than 90% (such as 95%) with SEQ ID NO: 2;

b) a second ISVD that has an amino acid sequence comprising a sequence identity of more than 90% (such as 95%) with SEQ ID NO: 3; and c) a third amino acid sequence comprising a sequence identity of more than 90% (such as 95%) identity with SEQ ID NO: 5.

The Polypeptide of the Present Technology May Comprise:

a) a first ISVD comprising the amino acid sequence of SEQ ID NO: 2;

b) a second ISVD comprising the amino acid sequence of SEQ ID NO: 3; and c) a third ISVD comprising the amino acid sequence of SEQ ID NO: 5.

The polypeptide of the present technology may further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units. Said one or more other groups, residues, moieties or binding units that provide the polypeptide with increased half-life may be chosen from the group consisting of a polyethylene glycol molecule, serum proteins or fragments thereof, binding units that can bind to serum proteins, an Fc portion, and small proteins or peptides that can bind to serum proteins. The binding units that provide the polypeptide with increased half-life may be chosen from the group consisting of binding units that can bind to serum albumin (such as human serum albumin) or a serum immunoglobulin (such as IgG), e.g. human serum albumin.

The polypeptide of the present technology may comprise an ISVD binding to human serum albumin that comprises:

i. a CDR1 that is the amino acid sequence of SEQ ID NO: 8 or an amino acid sequence with 2 or 1 amino acid difference(s) with SEQ ID NO: 8;

ii. a CDR2 that is the amino acid sequence of SEQ ID NO: 12 or an amino acid sequence with 2 or 1 amino acid difference(s) with SEQ ID NO: 12; and iii. a CDR3 that is the amino acid sequence of SEQ ID NO: 16 or an amino acid sequence with 2 or 1 amino acid difference(s) with SEQ ID NO: 16.

In one embodiment, the ISVD binding to human serum albumin comprises a CDR1 that is the amino acid sequence of SEQ ID NO: 8, a CDR2 that is the amino acid sequence of SEQ ID NO: 12 and a CDR3 that is the amino acid sequence of SEQ ID NO: 16. In one embodiment, the ISVD binding to human serum albumin comprises a sequence identity of more than 90% (such as 95%) with SEQ ID NO: 4. In one embodiment, the ISVD binding to human serum albumin comprises or consists of the amino acid sequence of SEQ ID NO: 4.

The ISVD binding to human serum albumin may be positioned in the polypeptide of the present technology at any position (i.e. N-terminal, between two building blocks, or C-terminal. In one embodiment the ISVD binding to human serum albumin is positioned between the second and the third ISVD that specifically bind to the p19 subunit of IL-23.

The polypeptide of the present technology may comprise an amino acid sequence comprising a sequence identity of more than 90% (such as 95%) with SEQ ID NO: 1. In one embodiment, the polypeptide of the present technology comprises or consists of the amino acid sequence of SEQ ID NO: 1.

Also provided is a nucleic acid comprising a nucleotide sequence that encodes a polypeptide of the present technology.

Also provided is a host or host cell comprising such a nucleic acid.

Also provided is a method for producing a polypeptide of the present technology, said method at least comprising the steps of:

a) expressing, in a suitable host cell or host organism or in another suitable expression system, a nucleic acid encoding the polypeptide of the present technology; optionally followed by:

b) isolating and/or purifying the polypeptide.

Also provided is a composition comprising at least one polypeptide of the present technology, or a nucleic acid encoding a polypeptide of the present technology. The composition may be a pharmaceutical composition which further comprises at least one pharmaceutically acceptable carrier, diluent or excipient and/or adjuvant, and optionally comprises one or more further pharmaceutically active polypeptides and/or compounds.

The polypeptide of the present technology can be used in the treatment. More specifically, the polypeptide of the present technology can be used in the treatment of an autoimmune or inflammatory disease, such as a disease selected from inflammatory bowel disease, such as Crohn's disease and ulcerative colitis, psoriasis, psoriatic arthritis and Hidradenitis suppurativa.

Accordingly, the present technology also encompasses a method of treating an autoimmune or inflammatory disease. In some embodiments, the present technology encompasses a method of treating a disease selected from inflammatory bowel disease, such as Crohn's disease and ulcerative colitis, psoriasis, psoriatic arthritis and Hidradenitis suppurativa, wherein said method comprises administering, to a subject in need thereof, a pharmaceutically active amount of a polypeptide of the present technology, a nucleic acid encoding a polypeptide of the present technology or a composition comprising the same.

Accordingly, the present technology also encompasses the use of a polypeptide of the present technology, in the preparation of a pharmaceutical composition for treating an autoimmune or inflammatory disease. In some embodiments, the present technology also encompasses the use of a polypeptide of the present technology, in the preparation of a pharmaceutical composition for treating a disease selected from inflammatory bowel disease, such as Crohn's disease and ulcerative colitis, psoriasis, psoriatic arthritis and Hidradenitis suppurativa.

In Particular, the Present Technology Provides the Following Embodiments:

Embodiment 1. A polypeptide, a composition comprising the polypeptide, or a composition comprising a nucleic acid comprising a nucleotide sequence that encodes the polypeptide, for use as a medicament, wherein the polypeptide comprises or consists of at least three immunoglobulin single variable domains (ISVDs), wherein each of said ISVDs comprises three complementarity determining regions (CDR1 to CDR3, respectively), optionally linked via one or more peptidic linkers; and wherein:

a) a first ISVD comprises
  - x. a CDR1 that is the amino acid sequence of SEQ ID NO: 6 or an amino acid sequence with 2 or 1 amino acid difference(s) with SEQ ID NO: 6;
  - xi. a CDR2 that is the amino acid sequence of SEQ ID NO: 10 or an amino acid sequence with 2 or 1 amino acid difference(s) with SEQ ID NO: 10; and
  - xii. a CDR3 that is the amino acid sequence of SEQ ID NO: 14 or an amino acid sequence with 2 or 1 amino acid difference(s) with SEQ ID NO: 14;

b) a second ISVD comprises
  - xiii. a CDR1 that is the amino acid sequence of SEQ ID NO: 7 or an amino acid sequence with 2 or 1 amino acid difference(s) with SEQ ID NO: 7;
  - xiv. a CDR2 that is the amino acid sequence of SEQ ID NO: 11 or an amino acid sequence with 2 or 1 amino acid difference(s) with SEQ ID NO: 11; and
  - xv. a CDR3 that is the amino acid sequence of SEQ ID NO: 15 or an amino acid sequence with 2 or 1 amino acid difference(s) with SEQ ID NO: 15; and c) a third ISVD comprises
  - xvi. a CDR1 that is the amino acid sequence of SEQ ID NO: 9 or an amino acid sequence with 2 or 1 amino acid difference(s) with SEQ ID NO: 9;
  - xvii. a CDR2 that is the amino acid sequence of SEQ ID NO: 13 or an amino acid sequence with 2 or 1 amino acid difference(s) with SEQ ID NO: 13; and
  - xviii. a CDR3 that is the amino acid sequence of SEQ ID NO: 17 or an amino acid sequence with 2 or 1 amino acid difference(s) with SEQ ID NO: 17, wherein the ISVDs are in the order starting from the N-terminus.

Embodiment 2. The composition for use according to embodiment 1, which is a pharmaceutical composition which further comprises at least one pharmaceutically acceptable carrier, diluent or excipient and/or adjuvant, and optionally comprises one or more further pharmaceutically active polypeptides and/or compounds.

Embodiment 3. The polypeptide or composition for use according to embodiment 1 or 2, wherein the polypeptide specifically binds TNFα and the p19 subunit of IL-23.

Embodiment 4. The polypeptide or composition for use according to any of embodiments 1 to 3, wherein the polypeptide specifically binds human TNFα and the p19 subunit of human IL-23.

Embodiment 5. The polypeptide or composition for use according to any of embodiments 1 to 4, wherein the first ISVD specifically binds to TNFα and the second and third ISVDs specifically bind to the p19 subunit of IL-23.

Embodiment 6. The polypeptide or composition for use according to any of embodiments 1 to 5, wherein the first ISVD specifically binds to human TNFα and the second and third ISVDs specifically bind to the p19 subunit of human IL-23.

Embodiment 7. The polypeptide or composition for use according to any of embodiments 1 to 6, wherein:

a) said first ISVD comprises a CDR1 that is the amino acid sequence of SEQ ID NO: 6, a CDR2 that is the amino acid sequence of SEQ ID NO: 10 and a CDR3 that is the amino acid sequence of SEQ ID NO: 14;

b) said second ISVD comprises a CDR1 that is the amino acid sequence of SEQ ID NO: 7, a CDR2 that is the amino acid sequence of SEQ ID NO: 11 and a CDR3 that is the amino acid sequence of SEQ ID NO: 15; and c) said third ISVD comprises a CDR1 that is the amino acid sequence of SEQ ID NO: 9, a CDR2 that is the amino acid sequence of SEQ ID NO: 13 and a CDR3 that is the amino acid sequence of SEQ ID NO: 17.

Embodiment 8. The polypeptide or composition for use according to any of embodiments 1 to 7, wherein:

a) the amino acid sequence of said first ISVD comprises a sequence identity of more than 90% (such as 95%) with SEQ ID NO: 2;

b) the amino acid sequence of said second ISVD comprises a sequence identity of more than 90% (such as 95%) with SEQ ID NO: 3; and c) the amino acid sequence of said third ISVD comprises a sequence identity of more than 90% (such as 95%) identity with SEQ ID NO: 5.

Embodiment 9. The polypeptide or composition for use according to any of embodiments 1 to 8, wherein:

a) said first ISVD comprises the amino acid sequence of SEQ ID NO: 2;

b) said second ISVD comprises the amino acid sequence of SEQ ID NO: 3; and c) said third ISVD comprises the amino acid sequence of SEQ ID NO: 5.

Embodiment 10. The polypeptide or composition for use according to any of embodiments 1 to 9, wherein said polypeptide further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units.

Embodiment 11. The polypeptide or composition for use according to embodiment 10, in which said one or more other groups, residues, moieties or binding units that provide the polypeptide with increased half-life is chosen from the group consisting of a polyethylene glycol molecule, serum proteins or fragments thereof, binding units that can bind to serum proteins, an Fc portion, and small proteins or peptides that can bind to serum proteins.

Embodiment 12. The polypeptide or composition for use according to any one of embodiments 10 to 11, in which said binding units that provide the polypeptide with increased half-life is chosen from the group consisting of binding units that can bind to serum albumin (such as human serum albumin) or a serum immunoglobulin (such as IgG).

Embodiment 13. The polypeptide or composition for use according to embodiment 12, in which said binding unit that provides the polypeptide with increased half-life is an ISVD that can bind to human serum albumin.

Embodiment 14. The polypeptide or composition for use according to embodiment 13, wherein the ISVD binding to human serum albumin comprises i. a CDR1 that is the amino acid sequence of SEQ ID NO: 8 or an amino acid sequence with 2 or 1 amino acid difference(s) with SEQ ID NO: 8;
ii. a CDR2 that is the amino acid sequence of SEQ ID NO: 12 or an amino acid sequence with 2 or 1 amino acid difference(s) with SEQ ID NO: 12; and
iii. a CDR3 that is the amino acid sequence of SEQ ID NO: 16 or an amino acid sequence with 2 or 1 amino acid difference(s) with SEQ ID NO: 16.

Embodiment 15. The polypeptide or composition for use according to any of embodiments 13 to 14, wherein the ISVD binding to human serum albumin comprises a CDR1 that is the amino acid sequence of SEQ ID NO: 8, a CDR2 that is the amino acid sequence of SEQ ID NO: 12 and a CDR3 that is the amino acid sequence of SEQ ID NO: 16.

Embodiment 16. The polypeptide or composition for use according to any of embodiments 13 to 15, wherein the amino acid sequence of said ISVD binding to human serum albumin comprises a sequence identity of more than 90% (such as 95%) with SEQ ID NO: 4.

Embodiment 17. The polypeptide or composition for use according to any of embodiments 13 to 16, wherein said ISVD binding to human serum albumin comprises or consists of the amino acid sequence of SEQ ID NO: 4.

Embodiment 18. The polypeptide or composition for use according to any of embodiments 1 to 17, wherein the amino acid sequence of the polypeptide comprises a sequence identity of more than 90% (such as 95%) with SEQ ID NO: 1.

Embodiment 19. The polypeptide or composition for use according to any of embodiments 1 to 18, wherein the polypeptide comprises or consists of the amino acid sequence of SEQ ID NO: 1.

Embodiment 20. The polypeptide or composition for use according to any of embodiments 1 to 19, for use in the treatment of an autoimmune disease or an inflammatory disease, such as a disease selected from inflammatory bowel disease, such as Crohn's disease and ulcerative colitis, psoriasis, psoriatic arthritis and Hidradenitis suppurativa.

Embodiment 21. A polypeptide that comprises or consists of at least three immunoglobulin single variable domains (ISVDs), wherein each of said ISVDs comprises three complementarity determining regions (CDR1 to CDR3, respectively), optionally linked via one or more peptidic linkers; and wherein:

a) a first ISVD comprises
   x. a CDR1 that is the amino acid sequence of SEQ ID NO: 6 or an amino acid sequence with 2 or 1 amino acid difference(s) with SEQ ID NO: 6;
   xi. a CDR2 that is the amino acid sequence of SEQ ID NO: 10 or an amino acid sequence with 2 or 1 amino acid difference(s) with SEQ ID NO: 10; and
   xii. a CDR3 that is the amino acid sequence of SEQ ID NO: 14 or an amino acid sequence with 2 or 1 amino acid difference(s) with SEQ ID NO: 14;
b) a second ISVD comprises
   xiii. a CDR1 that is the amino acid sequence of SEQ ID NO: 7 or an amino acid sequence with 2 or 1 amino acid difference(s) with SEQ ID NO: 7;
   xiv. a CDR2 that is the amino acid sequence of SEQ ID NO: 11 or an amino acid sequence with 2 or 1 amino acid difference(s) with SEQ ID NO: 11; and
   xv. a CDR3 that is the amino acid sequence of SEQ ID NO: 15 or an amino acid sequence with 2 or 1 amino acid difference(s) with SEQ ID NO: 15; and
c) a third ISVD comprises
   xvi. a CDR1 that is the amino acid sequence of SEQ ID NO: 9 or an amino acid sequence with 2 or 1 amino acid difference(s) with SEQ ID NO: 9;
   xvii. a CDR2 that is the amino acid sequence of SEQ ID NO: 13 or an amino acid sequence with 2 or 1 amino acid difference(s) with SEQ ID NO: 13; and
   xviii. a CDR3 that is the amino acid sequence of SEQ ID NO: 17 or an amino acid sequence with 2 or 1 amino acid difference(s) with SEQ ID NO: 17, wherein the ISVDs are in the order starting from the N-terminus.

Embodiment 22. The polypeptide according to embodiment 21, wherein the polypeptide specifically binds TNFα and the p19 subunit of IL-23.

Embodiment 23. The polypeptide according to embodiments 21 or 22, wherein the polypeptide specifically binds human TNFα and the p19 subunit of human IL-23.

Embodiment 24. The polypeptide according to any of embodiments 21 to 23, wherein the first ISVD specifically binds to TNFα and the second and third ISVDs specifically bind to the p19 subunit of IL-23.

Embodiment 25. The polypeptide according to any of embodiments 21 to 24, wherein the first ISVD specifically binds to human TNFα and the second and third ISVDs specifically bind to the p19 subunit of human IL-23.

Embodiment 26. The polypeptide according to any of embodiments 21 to 25, wherein:

a) said first ISVD comprises a CDR1 that is the amino acid sequence of SEQ ID NO: 6, a CDR2 that is the amino acid sequence of SEQ ID NO: 10 and a CDR3 that is the amino acid sequence of SEQ ID NO: 14;
b) said second ISVD comprises a CDR1 that is the amino acid sequence of SEQ ID NO: 7, a CDR2 that is the amino acid sequence of SEQ ID NO: 11 and a CDR3 that is the amino acid sequence of SEQ ID NO: 15; and
c) said third ISVD comprises a CDR1 that is the amino acid sequence of SEQ ID NO: 9, a CDR2 that is the amino acid sequence of SEQ ID NO: 13 and a CDR3 that is the amino acid sequence of SEQ ID NO: 17.

Embodiment 27. The polypeptide according to any of embodiments 21 to 26, wherein:

a) the amino acid sequence of said first ISVD comprises a sequence identity of more than 90% (such as 95%) with SEQ ID NO: 2;

b) the amino acid sequence of said second ISVD comprises a sequence identity of more than 90% (such as 95%) with SEQ ID NO: 3; and c) the amino acid sequence of said third ISVD comprises a sequence identity of more than 90% (such as 95%) identity with SEQ ID NO: 5.

Embodiment 28. The polypeptide according to any of embodiments 21 to 27, wherein:

a) said first ISVD comprises the amino acid sequence of SEQ ID NO: 2;

b) said second ISVD comprises the amino acid sequence of SEQ ID NO: 3; and c) said third ISVD comprises the amino acid sequence of SEQ ID NO: 5.

Embodiment 29. The polypeptide according to any of embodiments 21 to 28, wherein said polypeptide further comprises one or more other groups, residues, moieties or binding units, optionally linked via one or more peptidic linkers, in which said one or more other groups, residues, moieties or binding units provide the polypeptide with increased half-life, compared to the corresponding polypeptide without said one or more other groups, residues, moieties or binding units.

Embodiment 30. The polypeptide according to embodiment 29, in which said one or more other groups, residues, moieties or binding units that provide the polypeptide with increased half-life is chosen from the group consisting of a polyethylene glycol molecule, serum proteins or fragments thereof, binding units that can bind to serum proteins, an Fc portion, and small proteins or peptides that can bind to serum proteins.

Embodiment 31. The polypeptide according to any one of embodiments 29 to 30, in which said one or more other groups, residues, moieties or binding units that provide the polypeptide with increased half-life is chosen from the group consisting of binding units that can bind to serum albumin (such as human serum albumin) or a serum immunoglobulin (such as IgG).

Embodiment 32. The polypeptide according to embodiment 31, in which said binding unit that provides the polypeptide with increased half-life is an ISVD that can bind to human serum albumin.

Embodiment 33. The polypeptide according to embodiment 32, wherein the ISVD binding to human serum albumin comprises:

i. a CDR1 that is the amino acid sequence of SEQ ID NO: 8 or an amino acid sequence with 2 or 1 amino acid difference(s) with SEQ ID NO: 8;

ii. a CDR2 that is the amino acid sequence of SEQ ID NO: 12 or an amino acid sequence with 2 or 1 amino acid difference(s) with SEQ ID NO: 12; and iii. a CDR3 that is the amino acid sequence of SEQ ID NO: 16 or an amino acid sequence with 2 or 1 amino acid difference(s) with SEQ ID NO: 16.

Embodiment 34. The polypeptide according to any of embodiments 32 to 33, wherein the ISVD binding to human serum albumin comprises a CDR1 that is the amino acid sequence of SEQ ID NO: 8, a CDR2 that is the amino acid sequence of SEQ ID NO: 12 and a CDR3 that is the amino acid sequence of SEQ ID NO: 16.

Embodiment 35. The polypeptide according to any of embodiments 32 to 34, wherein the amino acid sequence of said ISVD binding to human serum albumin comprises a sequence identity of more than 90% (such as 95%) with SEQ ID NO: 4.

Embodiment 36. The polypeptide according to any of embodiments 32 to 35, wherein said ISVD binding to human serum albumin comprises or consists of the amino acid sequence of SEQ ID NO: 4.

Embodiment 37. The polypeptide according to any of embodiments 21 to 36, wherein the amino acid sequence of the polypeptide comprises a sequence identity of more than 90% (such as 95%) with SEQ ID NO: 1.

Embodiment 38. The polypeptide according to any of embodiments 21 to 37, wherein the polypeptide comprises or consists of the amino acid sequence of SEQ ID NO: 1.

Embodiment 39. A nucleic acid comprising a nucleotide sequence that encodes a polypeptide according to any of embodiments 21 to 38.

Embodiment 40. A host or host cell comprising a nucleic acid according to embodiment 39.

Embodiment 41. A method for producing a polypeptide according to any of embodiments 21 to 38, said method at least comprising the steps of:

a) expressing, in a suitable host cell or host organism or in another suitable expression system, a nucleic acid according to embodiment 39; optionally followed by:

b) isolating and/or purifying the polypeptide according to any of embodiments 21 to 38.

Embodiment 42. A composition comprising at least one polypeptide according to any of embodiments 21 to 38, or a nucleic acid according to embodiment 39.

Embodiment 43. The composition according to embodiment 42, which is a pharmaceutical composition which further comprises at least one pharmaceutically acceptable carrier, diluent or excipient and/or adjuvant, and optionally comprises one or more further pharmaceutically active polypeptides and/or compounds.

Embodiment 44. A method of treating an autoimmune disease or an inflammatory disease, wherein said method comprises administering, to a subject in need thereof, a pharmaceutically active amount of a polypeptide according to any of embodiments 21 to 38 or a composition according to any of embodiments 42 to 43.

Embodiment 45. The method according to embodiment 44, wherein the autoimmune disease or inflammatory disease is selected from inflammatory bowel disease, such as Crohn's disease and ulcerative colitis, psoriasis, psoriatic arthritis and Hidradenitis suppurativa.

Embodiment 45. Use of a polypeptide according to any of embodiments 21 to 38 or a composition according to any of embodiments 42 to 43, in the preparation of a pharmaceutical composition for treating an autoimmune disease or an inflammatory disease.

Embodiment 46. Use of the polypeptide or composition according to embodiment 45, wherein the autoimmune disease or inflammatory disease is selected from inflammatory bowel disease, such as Crohn's disease and ulcerative colitis, psoriasis, psoriatic arthritis and Hidradenitis suppurativa.

4 BRIEF DESCRIPTION OF THE DRAWINGS

FIG. 1: Sensorgram showing simultaneous binding of TNFα and IL-23 to F027500069 captured via human serum albumin (HSA).

Figure 2A:
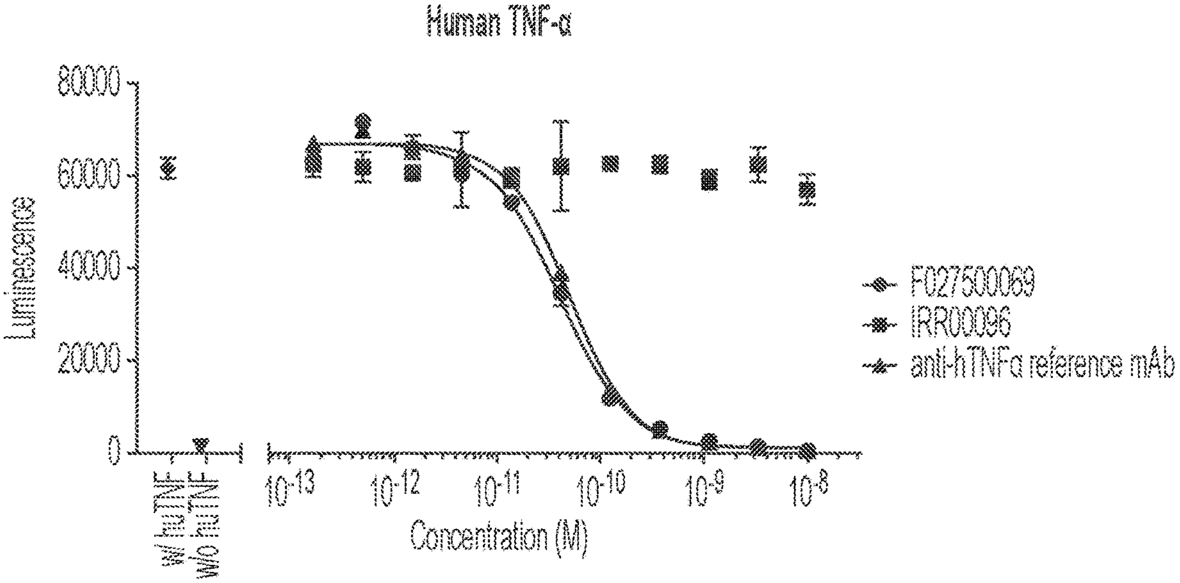
Figure 2B:
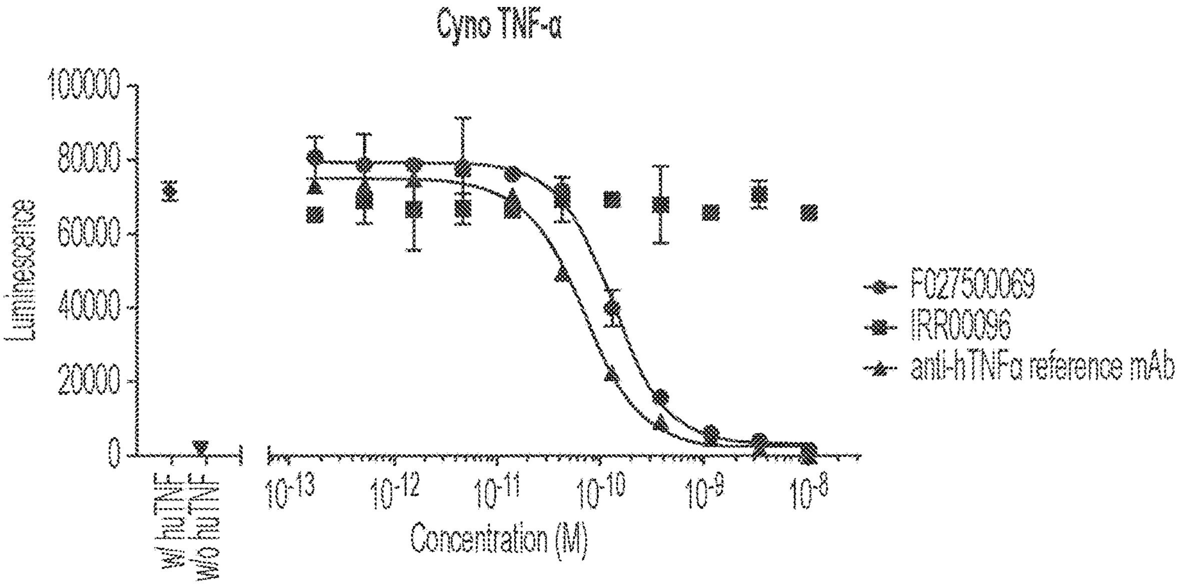

FIGS. 2A-2B: Inhibition of soluble human (FIG. 2A) and cyno (FIG. 2B) TNFα in the Glo Response™ HEK293_NFκB-NLucP reporter assay by F027500069 and anti-hTNFα reference mAb. IRR00096 is a negative control $V_{HH}$. Datapoints are global mean values (n=2), error bars represent+/−SD.

Figure 3A:
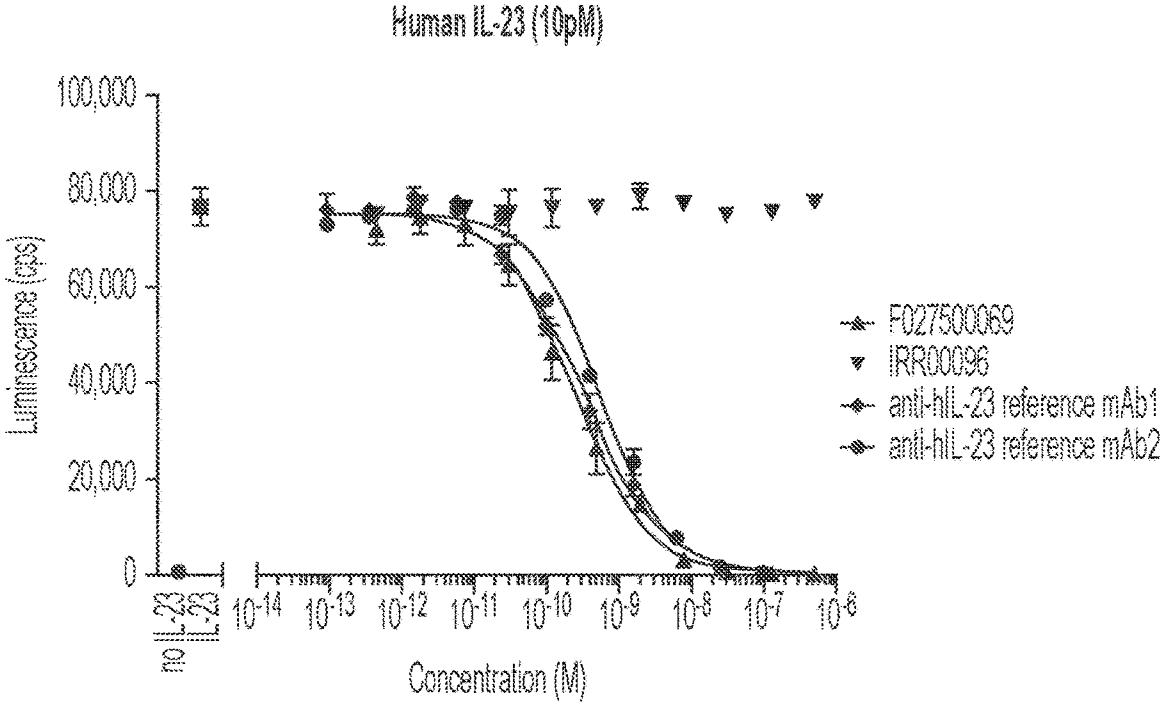
Figure 3B:
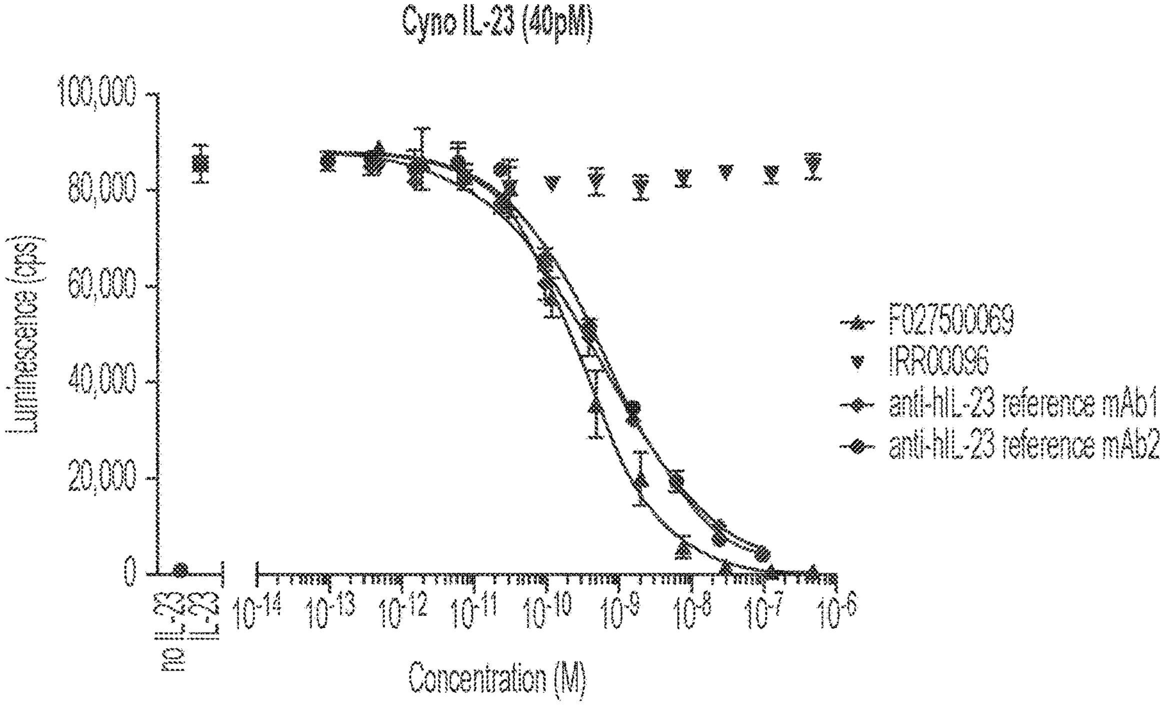

FIGS. 3A-3B: Inhibition of human (FIG. 3A) and cyno (FIG. 3B) IL-23 using the in the Glo Response™ HEK293_human IL-23R/IL-12Rb1-Luc2P reporter assay by F027500069, an anti-hIL-23 reference mAb1, an anti-hIL-23 reference mAb2. IRR00096 is a negative control $V_{HH}$. Datapoints are global mean values (n=2), error bars represent+/−SD.

Figure 4:
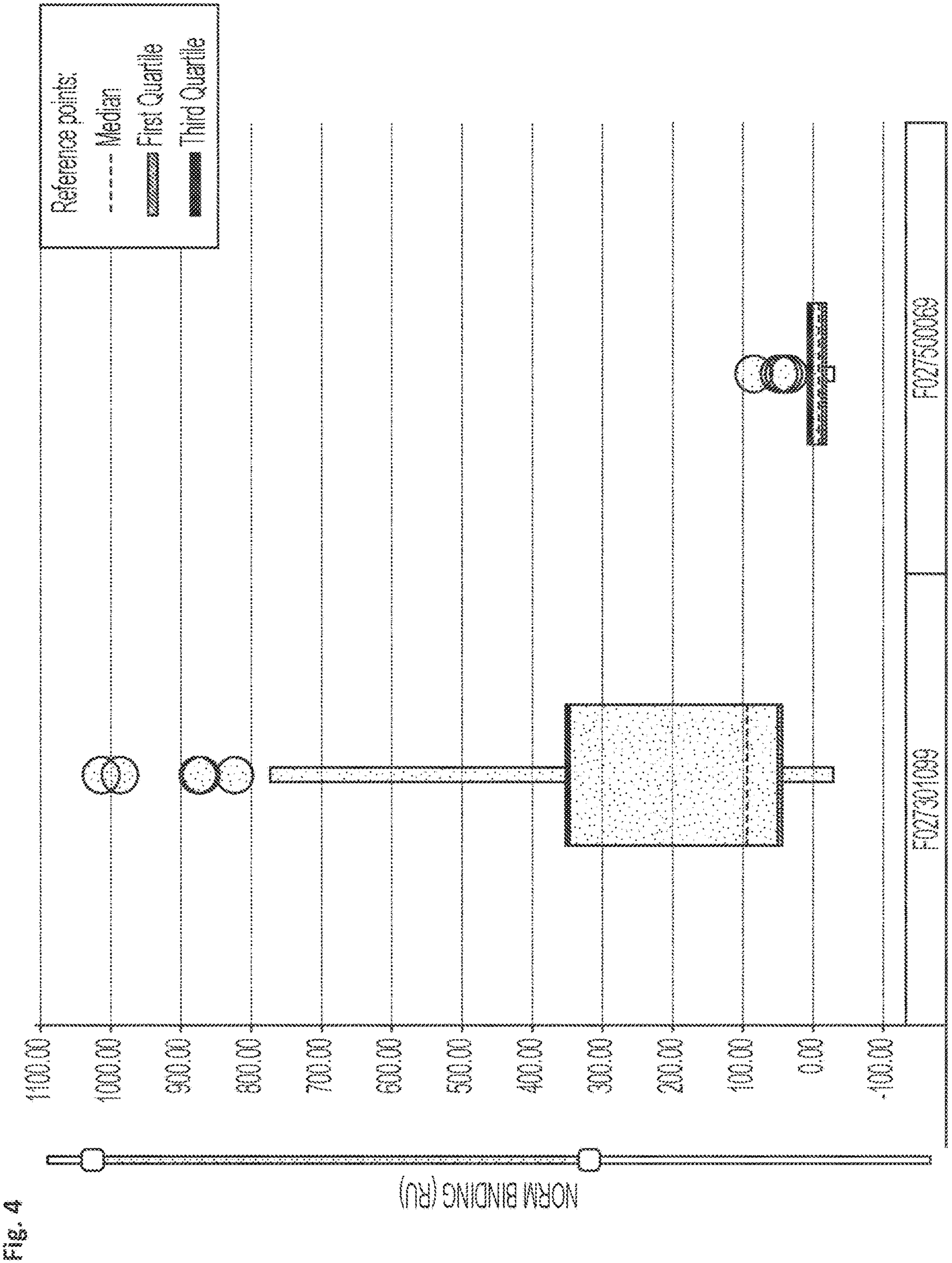

FIG. 4: Box plot showing the binding of pre-existing antibodies present in 96 human serum samples to F027500069 compared to control F027301099.

Figure 5:
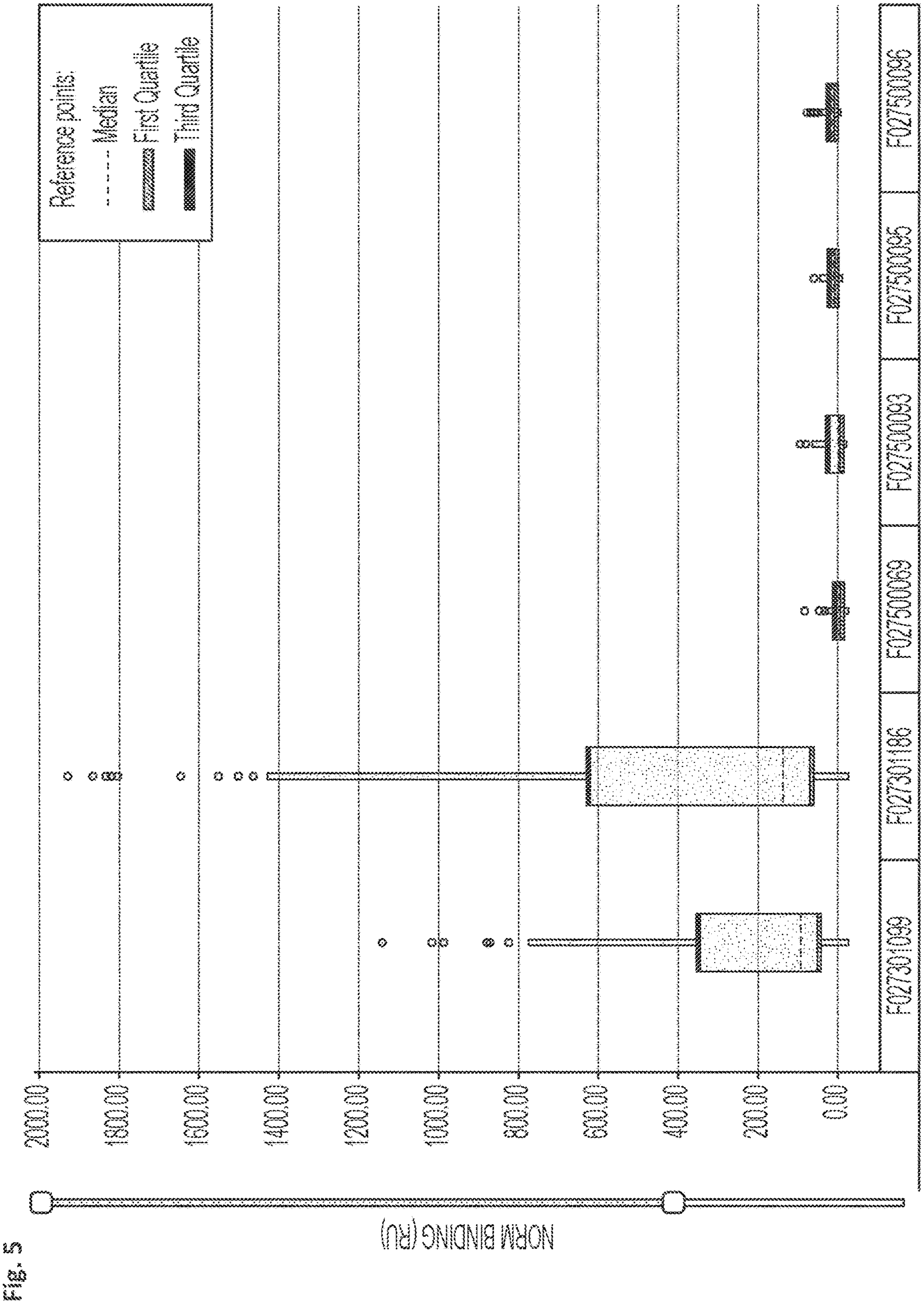

FIG. 5: Box plot showing the binding of pre-existing antibodies present in 96 human serum samples to F027500069, F027500093, F027500095 and F027500096 compared to control polypeptides F027301099 and F027301186.

Figure 6:
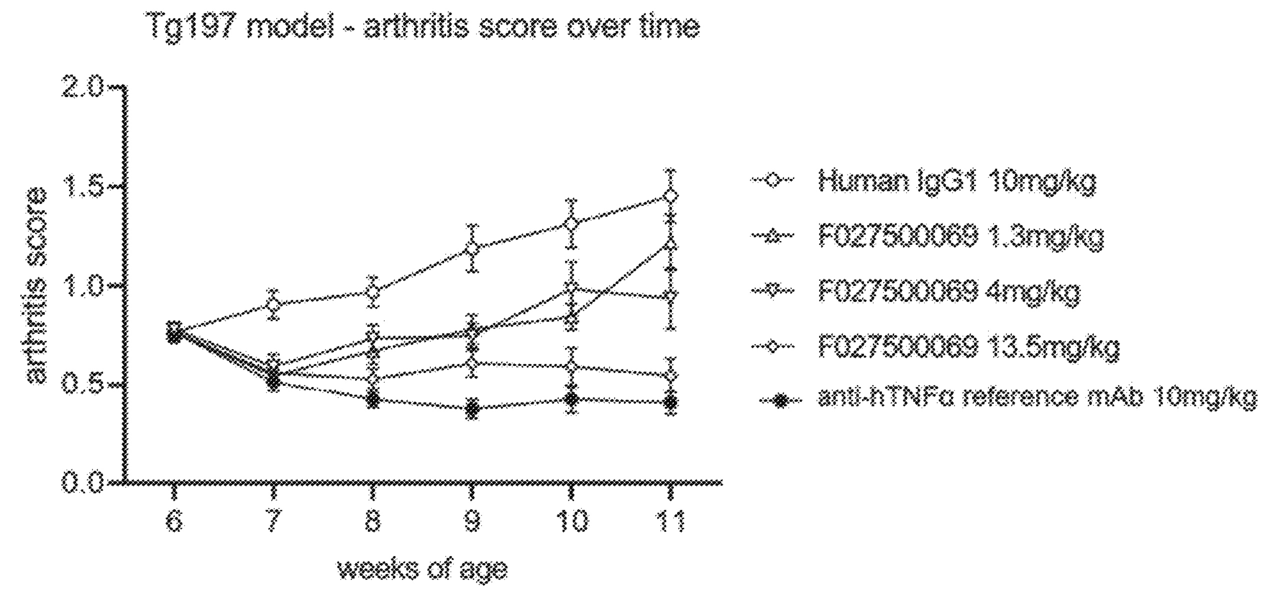

FIG. 6: Inhibition of polyarthritis in Tg197 human TNF transgenic mouse model. Plotted is arthritis score over time in different treatment groups (n=8 mice/group). Animals received intraperitoneal injections of the indicated compounds twice per week, starting at 6 weeks of age. Shown are mean weekly arthritis scores±SEM. Statistics are 2-way ANOVA and Bonferroni multiple comparison test.

Figure 7:
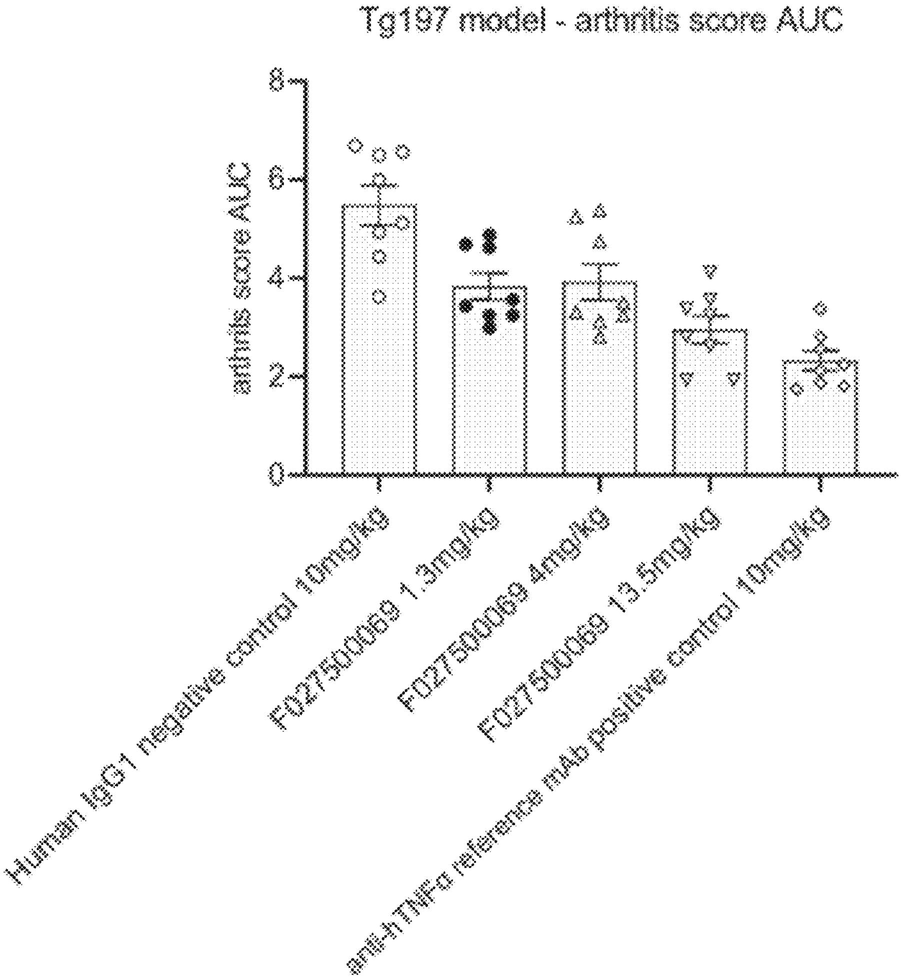

FIG. 7: Bar graph of the area under the curve for arthritis score in Tg197 mouse model over time. Shown are individual values (symbols) and means±SEM (bars). Statistics are 1-way ANOVA and Bonferroni multiple comparison test.

Figure 8:
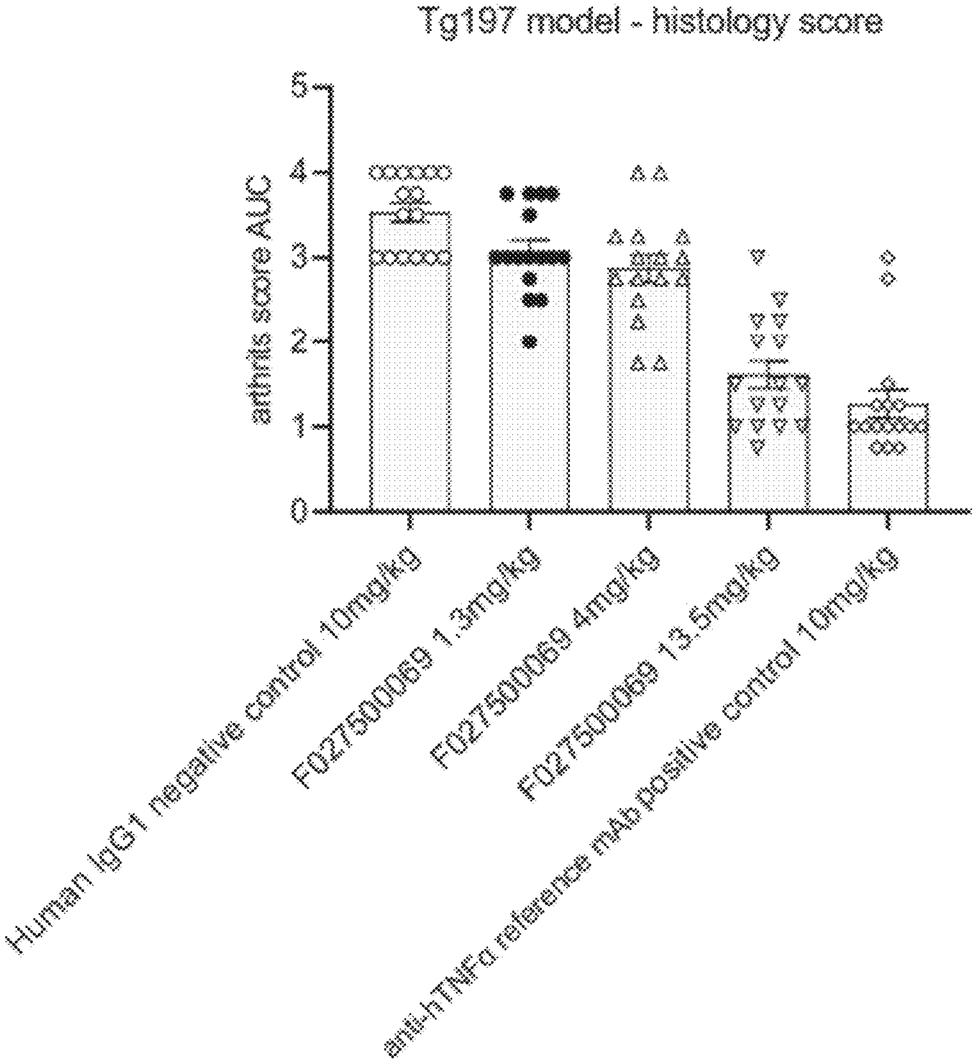

FIG. 8: Bar graph of histology score of paws of the Tg197 mouse model. Shown are individual values (symbols) and means±SEM (bars). Statistics are 1-way ANOVA and Bonferroni multiple comparison test.

Figure 9:
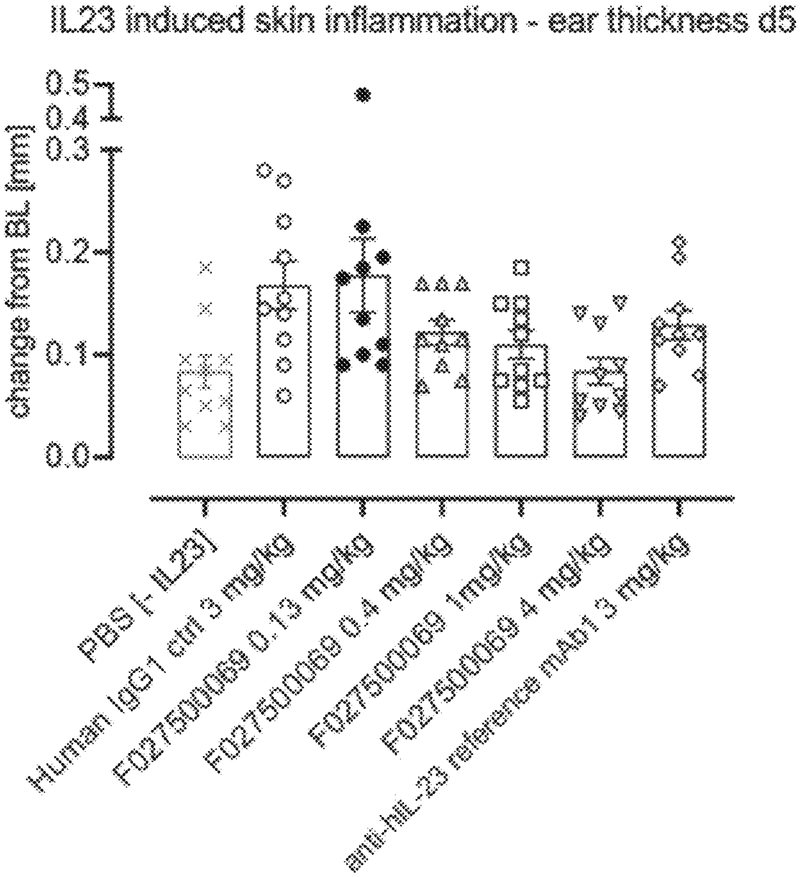

FIG. 9: Inhibition of skin inflammation in the human IL-23 model. Bar graph illustrates ear skin swelling of different treatment groups (n=10 mice/group). Animals received daily intradermal injections of recombinant human IL-23 or PBS from day 1 through 4. Animals received intraperitoneal injections of the indicated compounds on day 1 and 3. Shown are ear skin thickness mean change from baseline at day 5±SEM. Statistics are ANOVA and Bonferroni multiple comparison test.

Figure 10:
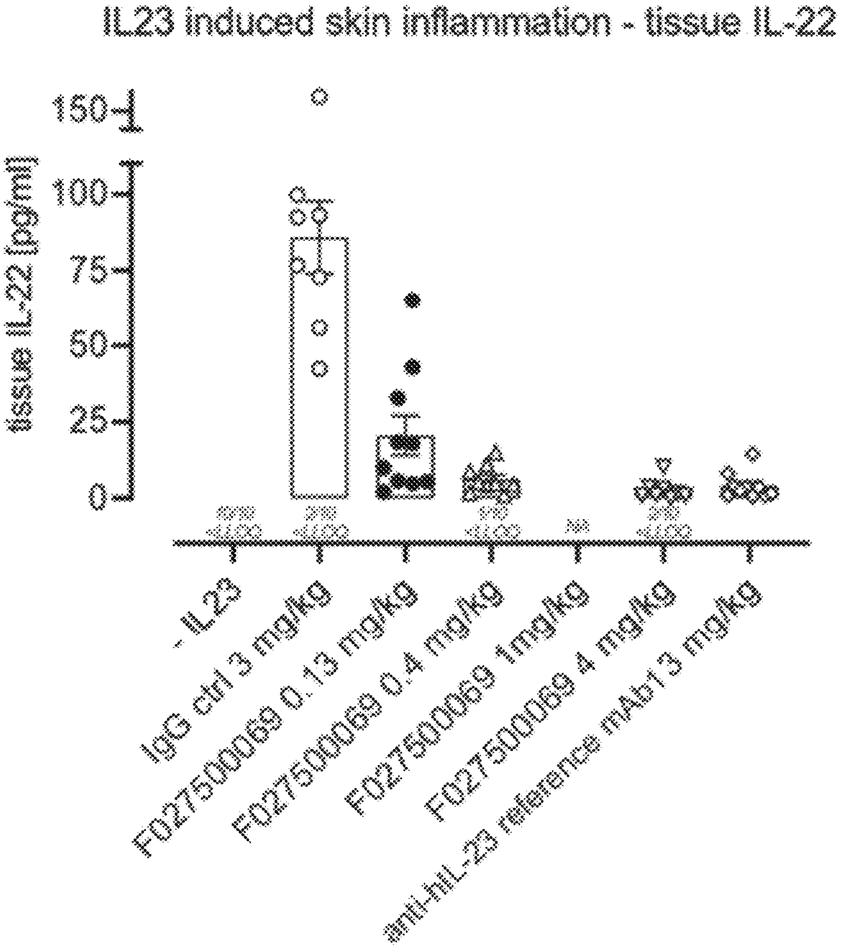

FIG. 10: Bar graph of tissue IL-22 concentrations form skin biopsies at day 5 of the human IL-23-induced skin inflammation model. Shown are individual values (symbols) and means±SEM (bars). Statistics are ANOVA and Bonferroni multiple comparison test.

Figure 11:
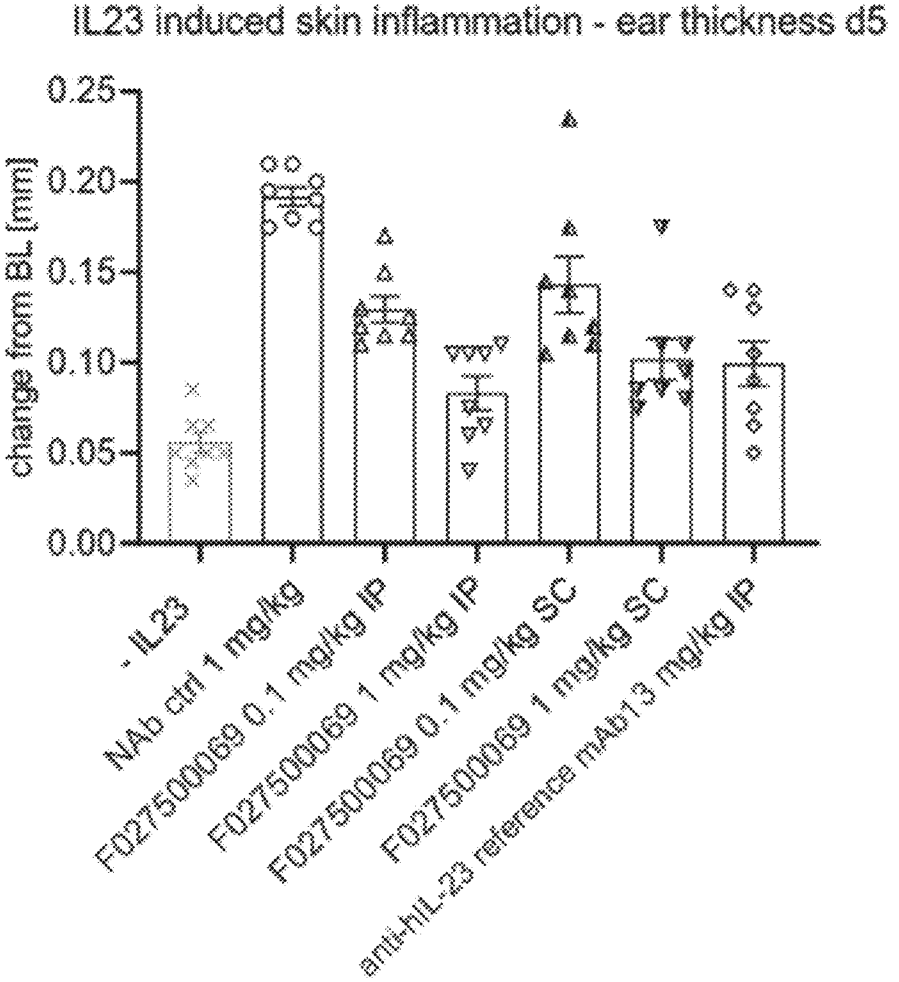

FIG. 11: Inhibition of skin inflammation by F027500069 administered both by the intraperitoneal as well as the subcutaneous route. Bar graph illustrates ear skin swelling of different treatment groups (n=8 mice/group). Animals received daily intradermal injections of recombinant human IL-23 or PBS from day 1 through 4. Intraperitoneal (IP) or subcutaneous (SC) injections of the indicated doses were administered on day 1 and 3. Shown are ear skin thickness mean change from baseline at day 5±SEM. Statistics are ANOVA and Bonferroni multiple comparison test.

Figure 12:
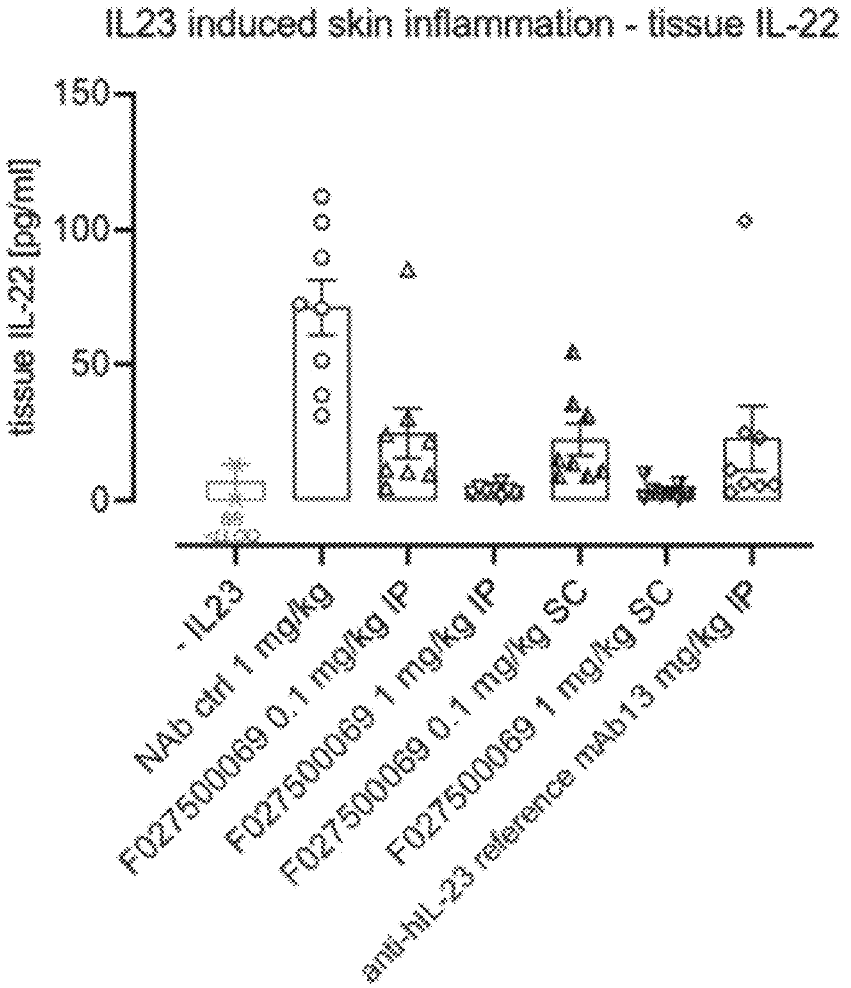

FIG. 12: Bar graph tissue IL-22 concentrations form skin biopsies at day 5 with F027500069 delivered by both the intraperitoneal as well as subcutaneous route. Shown are individual values (symbols) and means±SEM (bars). Statistics are ANOVA and Bonferroni multiple comparison test.

Figure 13:
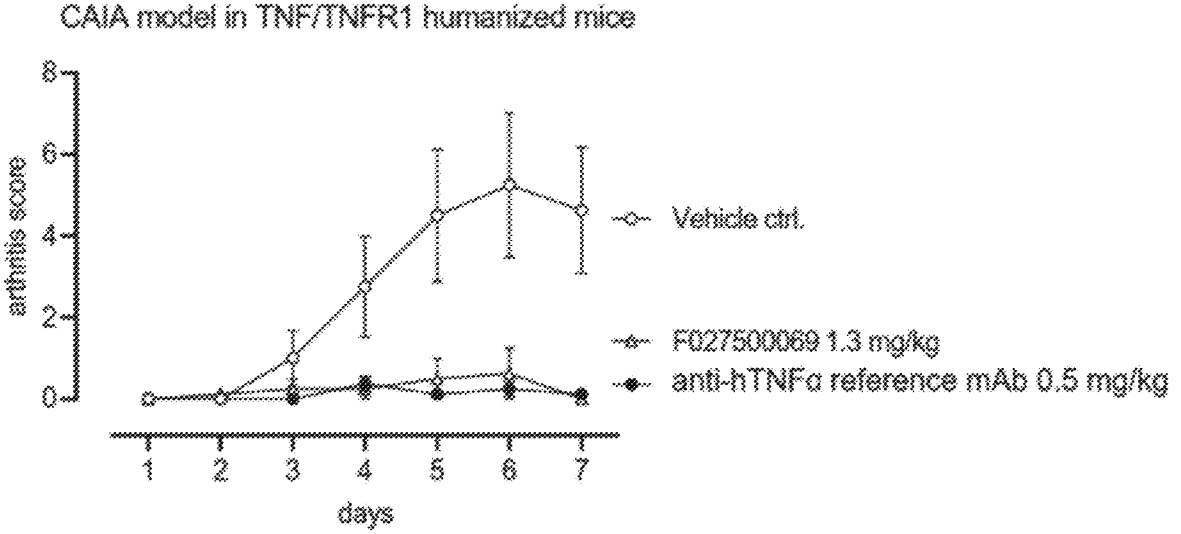

FIG. 13: Suppression of arthritis score in the Collagen-Antibody Induced Arthritis (CAIA) model in human TNFα/TNFR1 knock in mice. Shown is arthritis score over time in different treatment groups (n=8 mice/group). Animals received a single intraperitoneal injection of the indicated compounds at day 1, 6 hours after the LPS injection. Shown are mean daily arthritis scores±SEM. Statistics are 2-way ANOVA and Bonferroni multiple comparison test.

Figure 14:
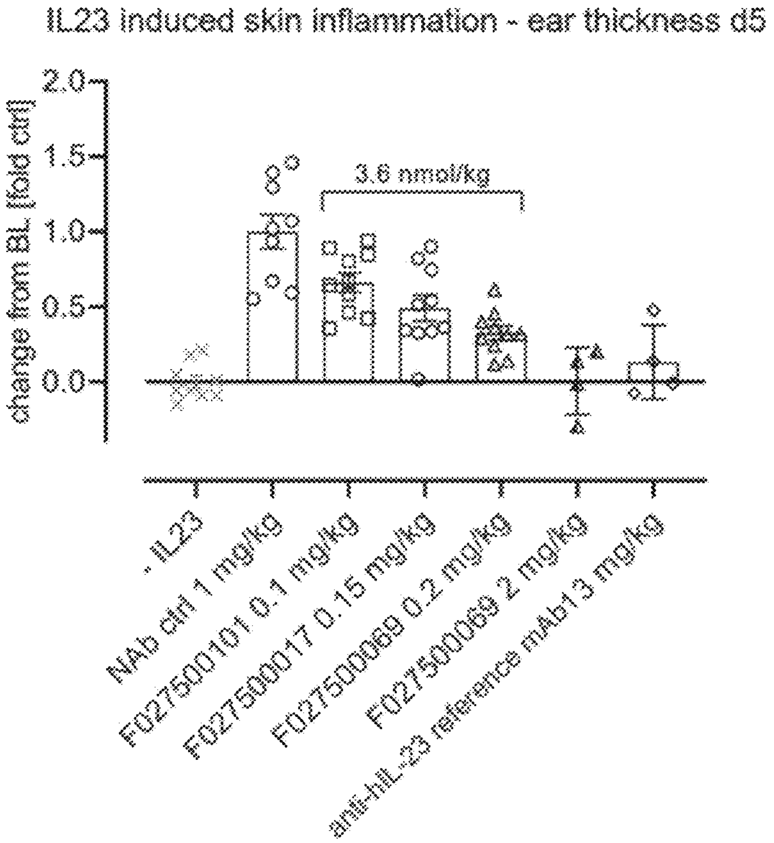

FIG. 14: Dual inhibition of IL-23 and TNFα induced inflammation in the human IL-23 skin injection model performed in human TNFα knock in mice (n=4-10 mice/group). Animals received daily intradermal injections of recombinant human IL-23 or PBS from day 1 through 4. Intraperitoneal injections of the indicated compounds on day 1 and 3. Shown are ear skin thickness mean change from baseline at day 5±SEM. Statistics are ANOVA and Bonferroni multiple comparison test.

Figure 15:
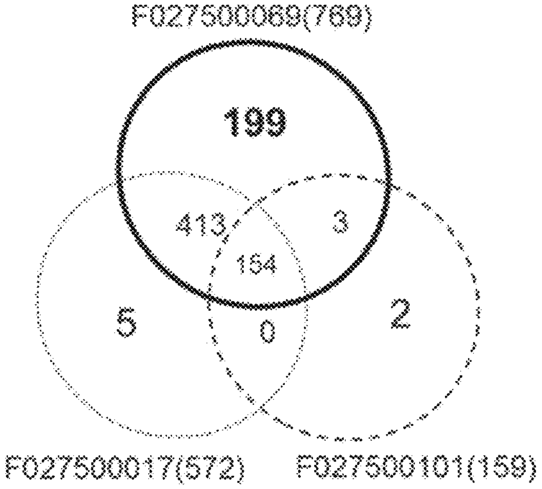

FIG. 15: Differential skin tissue gene expression in inflamed skin tissue after mono- or bi-specific inhibition of cytokines. Venn diagram of differentially expressed genes (DEGs, with fold change >2 at p<0.001). 199 out of a total 769 DEGs in the F027500069 were specific for this treatment.

Figure 16:
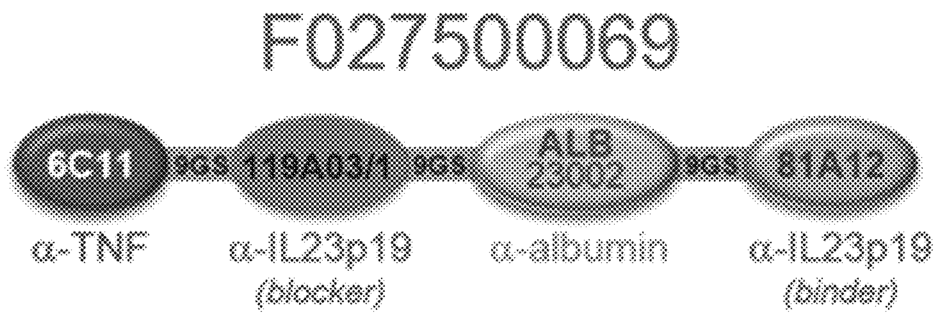

FIG. 16: Schematic presentation of ISVD construct F027500069 showing from the N-terminus to the C-terminus the monovalent building blocks/ISVDs 6C11, 119A03/1, ALB23002, and 81A12 connected via 9GS linkers.

5 DETAILED DESCRIPTION OF THE PRESENT TECHNOLOGY

The present technology aims at providing a novel type of drug for treating inflammatory bowel disease, such as Crohn's disease and ulcerative colitis, psoriasis, psoriatic arthritis or Hidradenitis suppurativa.

The present inventors have surprisingly found that a polypeptide comprising at least three ISVDs, wherein at least one ISVD specifically binds to TNFα and at least two ISVDs specifically bind to the p19 subunit of IL-23, can be used for more efficient treatment of autoimmune or inflammatory diseases as compared to monospecific anti-TNFα or anti-IL-23p19 polypeptides.

In some embodiments, the polypeptides of the present technology show a highly potency on TNFα and IL-23 (e.g. human or cyno TNFα and IL-23). In some embodiments, the polypeptides of the present technology are efficiently produced (e.g. in microbial hosts, such as *Pichia*, e.g. *P. pastoris*). In some embodiments, the polypeptides of the present technology have low viscosity at high concentrations, which is advantageous and convenient for subcutaneous administration. Furthermore, in some embodiments, the polypeptides of the present technology have limited reactivity to pre-existing antibodies in the subject to be treated (i.e. antibodies present in the subject before the first treatment with the antibody construct). In other embodiments such polypeptides exhibit a half-life in the subject to be treated that is long enough such that consecutive treatments can be conveniently spaced apart.

The polypeptide is at least bispecific, but can also be e.g. trispecific, tetraspecific or pentaspecific. Moreover, the polypeptide is at least trivalent, but can also be e.g. tetravalent or pentavalent.

The terms "bispecific", "trispecific", "tetraspecific" or "pentaspecific" all fall under the term "multispecific" and refer to binding to two, three, four or five different target molecules, respectively. The terms "bivalent", "trivalent", "tetravalent" or "pentavalent" all fall under the term "multivalent" and indicate the presence of two, three, four or five binding units (such as ISVDs), respectively. For example, the polypeptide may be trispecific-tetravalent, such as a polypeptide comprising or consisting of four ISVDs, wherein one ISVD binds to human TNFα, two ISVDs bind to human IL-23 and one ISVD binds to human serum albumin. Such a polypeptide may at the same time be biparatopic, for example if two ISVDs bind two different epitopes on the p19 subunit of IL-23. The term "biparatopic" refers to binding to two different parts (i.e., epitopes) of the same target molecule.

The terms "first ISVD", "second ISVD", "third ISVD", etc., as used herein only indicate the relative position of the ISVDs to each other, wherein the numbering is started from the N-terminus of the polypeptide of the present technology. The "first ISVD" is thus closer to the N-terminus than the "second ISVD", whereas the "second ISVD" is closer to the N-terminus than the "third ISVD", etc. Accordingly, the ISVD arrangement is inverse when considered from the C-terminus. Since the numbering is not absolute and only indicates the relative position of the at least three ISVDs it is not excluded that other binding units/building blocks such as additional ISVDs binding to TNFα or p19 subunit of IL-23, or ISVDs binding to another target may be present in the polypeptide. Moreover, it does not exclude the possibility that other binding units/building blocks such as ISVDs can be placed in between. For instance, as described further below (see in particular, section 5.3 "(In vivo) half-life extension"), the polypeptide can further comprise another ISVD binding to human serum albumin that can even be located between e.g., the "second ISVD" and "third ISVD".

In light of the above, the present technology provides a polypeptide comprising or consisting of at least three ISVDs, wherein at least one ISVD specifically binds to TNFα and at least two ISVDs specifically bind to the p19 subunit of IL-23.

The at least two ISVDs that specifically bind to IL-23 bind to the p19 subunit of IL-23. The at least two ISVDs that specifically bind to IL-23 may bind to different epitopes on the p19 subunit of IL-23. At least one of the ISVDs that specifically binds to IL-23 may be capable of blocking a function of IL-23, such as blocking the interaction between IL-23 and IL-23R and/or inhibiting IL-23-induced release of IL-22.

The components, e.g. the ISVDs, of the polypeptide may be linked to each other by one or more suitable linkers, such as peptidic linkers.

The use of linkers to connect two or more (poly)peptides is well known in the art. Exemplary peptidic linkers are shown in Table A-5. One often used class of peptidic linker are known as the "Gly-Ser" or "GS" linkers. These are linkers that essentially consist of glycine (G) and serine (S) residues, and usually comprise one or more repeats of a peptide motif such as the GGGGS (SEQ ID NO: 47) motif (for example, have the formula (Gly-Gly-Gly-Gly-Ser)n in which n may be 1, 2, 3, 4, 5, 6, 7 or more). Some often used examples of such GS linkers are 9GS linkers (GGGGSGGGS, SEQ ID NO: 50), 15GS linkers (n=3; SEQ ID NO: 52) and 35GS linkers (n=7; SEQ ID NO: 57). Reference is for example made to Chen et al., Adv. Drug Deliv. Rev. 2013 Oct. 15; 65(10): 1357-1369; and Klein et al., Protein Eng. Des. Sel. (2014) 27 (10): 325-330. In one embodiment of the polypeptide of the present technology, 9GS linkers to link the components of the polypeptide to each other, is used.

In one embodiment, the ISVD specifically binding to TNFα is positioned at the N-terminus of the polypeptide. The inventors surprisingly found that such a configuration can increase the production yield of the polypeptide.

Also in an embodiment, one of the ISVDs specifically binding to IL-23 is positioned at the C-terminus of the polypeptide.

Accordingly, the polypeptide comprises or consists of the following, in order starting from the N-terminus of the polypeptide: an ISVD specifically binding to TNFα, a first ISVD specifically binding to IL-23 that can block a function of IL-23, an optional binding unit providing the polypeptide with increased half-life as defined herein, and a second ISVD specifically binding to IL-23. In one embodiment, the binding unit providing the polypeptide with increased half-life is an ISVD.

In one embodiment, the polypeptide comprises or consists of the following, in order starting from the N-terminus of the polypeptide: an ISVD specifically binding to TNFα, a linker, a first ISVD specifically binding to IL-23 that can block a function of IL-23, a linker, an ISVD binding to human serum albumin, a linker, and a second ISVD specifically binding to IL-23. In one aspect each linker is a 9GS linker.

Such configurations of the polypeptide can provide for increased production yield and good CMC characteristics, including expression yield, viscosity and other biophysical properties.

In one embodiment, the polypeptide of the present technology exhibits reduced binding by pre-existing antibodies in human serum. To this end, in one embodiment, the polypeptide comprises a valine (V) at amino acid position 11 and a leucine (L) at amino acid position 89 (according to Kabat numbering) in at least one ISVD. In one embodiment, the polypeptide comprises a valine (V) at amino acid position 11 and a leucine (L) at amino acid position 89 (according to Kabat numbering) in each ISVD. In another embodiment, the polypeptide comprises an extension of 1 to 5 (naturally occurring) amino acids, such as a single alanine (A) extension, at the C-terminus of the C-terminal ISVD. The C-terminus of an ISVD is normally VTVSS (SEQ ID NO: 112). In another embodiment the polypeptide comprises a lysine (K) or glutamine (Q) at position 110 (according to Kabat numbering) in at least one ISVD. In another embodiment, the ISVD comprises a lysine (K) or glutamine (Q) at position 112 (according to Kabat numbering) in at least one ISVD. In these embodiments, the C-terminus of the ISVD is VKVSS (SEQ ID NO: 113), VQVSS (SEQ ID NO: 114), VTVKS (SEQ ID NO:146), VTVQS (SEQ ID NO:147), VKVKS (SEQ ID NO:148), VKVQS (SEQ ID NO:149), VQVKS (SEQ ID NO:150), or VQVQS (SEQ ID NO:151) such that after addition of a single alanine the C-terminus of the polypeptide for example comprises the sequence VTVSSA (SEQ ID NO: 115), VKVSSA (SEQ ID NO: 116), VQVSSA (SEQ ID NO: 117), VTVKSA (SEQ ID NO:152), VTVQSA (SEQ ID NO:153), VKVKSA (SEQ ID NO:154), VKVQSA (SEQ ID NO:155), VQVKSA (SEQ ID NO:156), or VQVQSA (SEQ ID NO:157). In one embodiment, the C-terminus comprises VKVSSA (SEQ ID NO: 116). In another embodiment, the polypeptide comprises a valine (V) at amino acid position 11 and a leucine (L) at amino acid position 89 (according to Kabat numbering) in each ISVD, optionally a lysine (K) or glutamine (Q) at position 110 (according to Kabat numbering) in at least one ISVD, and comprises an extension of 1 to 5 (naturally occurring) amino acids, such as a single alanine (A) extension, at the C-terminus of the C-terminal ISVD, such that the C-terminus of the polypeptide for example comprises the sequence VTVSSA (SEQ ID NO: 115), VKVSSA (SEQ ID NO: 116) or VQVSSA (SEQ ID NO: 117), such as VKVSSA (SEQ ID NO: 116). See e.g. WO2012/175741 and WO2015/173325 for further information in this regard.

In another embodiment, the polypeptide of the present technology comprises or consists of an amino acid sequence comprising a sequence identity of more than 90%, such as, more than 95% or more than 99%, with SEQ ID NO: 1, wherein the CDRs of the four ISVDs are as defined in items A to D (or A' to D' if using the Kabat definition) set forth in sections "5.1 Immunoglobulin single variable domains" and "5.3 (In vivo) half-life extension" below, respectively, wherein in particular:

- the ISVD specifically binding to TNFα comprises a CDR1 that is the amino acid sequence of SEQ ID NO: 6, a CDR2 that is the amino acid sequence of SEQ ID NO: 10 and a CDR3 that is the amino acid sequence of SEQ ID NO: 14;
- the first ISVD specifically binding to the p19 subunit of IL-23 comprises a CDR1 that is the amino acid sequence of SEQ ID NO: 7, a CDR2 that is the amino acid sequence of SEQ ID NO: 11 and a CDR3 that is the amino acid sequence of SEQ ID NO: 15;
- the second ISVD specifically binding to the p19 subunit of IL-23 comprises a CDR1 that is the amino acid sequence of SEQ ID NO: 9, a CDR2 that is the amino acid sequence of SEQ ID NO: 13 and a CDR3 that is the amino acid sequence of SEQ ID NO: 17; and
- the ISVD binding to human serum albumin comprises a CDR1 that is the amino acid sequence of SEQ ID NO: 8, a CDR2 that is the amino acid sequence of SEQ ID NO: 12 and a CDR3 that is the amino acid sequence of SEQ ID NO: 16, or alternatively if using the Kabat definition:

- the ISVD specifically binding to TNFα comprises a CDR1 that is the amino acid sequence of SEQ ID NO: 122, a CDR2 that is the amino acid sequence of SEQ ID NO: 130 and a CDR3 that is the amino acid sequence of SEQ ID NO: 138;
- the first ISVD specifically binding to the p19 subunit of IL-23 comprises a CDR1 that is the amino acid sequence of SEQ ID NO: 123, a CDR2 that is the amino acid sequence of SEQ ID NO: 131 and a CDR3 that is the amino acid sequence of SEQ ID NO: 139;
- the second ISVD specifically binding to the p19 subunit of IL-23 comprises a CDR1 that is the amino acid sequence of SEQ ID NO: 125, a CDR2 that is the amino acid sequence of SEQ ID NO: 133 and a CDR3 that is the amino acid sequence of SEQ ID NO: 141; and
- the ISVD binding to human serum albumin comprises a CDR1 that is the amino acid sequence of SEQ ID NO: 124, a CDR2 that is the amino acid sequence of SEQ ID NO: 132 and a CDR3 that is the amino acid sequence of SEQ ID NO: 140.

In another embodiment, the polypeptide comprises or consists of the amino acid sequence of SEQ ID NO: 1. In another embodiment, the polypeptide consists of the amino acid sequence of SEQ ID NO: 1.

In one embodiment, the polypeptide of the present technology has at least half the binding affinity, or at least the same binding affinity, to human TNFα and to human IL-23 as compared to a polypeptide consisting of the amino acid of SEQ ID NO: 1, wherein the binding affinity is measured using the same method, such as Surface Plasmon Resonance (SPR).

5.1 Immunoglobulin Single Variable Domains

The term "immunoglobulin single variable domain" (ISVD), interchangeably used with "single variable domain", defines immunoglobulin molecules wherein the antigen binding site is present on, and formed by, a single immunoglobulin domain. This sets ISVDs apart from "conventional" immunoglobulins (e.g. monoclonal antibodies) or their fragments (such as Fab, Fab', $F(ab')_2$, scFv, di-scFv), wherein two immunoglobulin domains, in particular two variable domains, interact to form an antigen binding site. Typically, in conventional immunoglobulins, a heavy chain variable domain ($V_H$) and a light chain variable domain ($V_L$) interact to form an antigen binding site. In this case, the complementarity determining regions (CDRs) of both $V_H$ and $V_L$ will contribute to the antigen binding site, i.e. a total of 6 CDRs will be involved in antigen binding site formation.

In view of the above definition, the antigen-binding domain of a conventional 4-chain antibody (such as an IgG, IgM, IgA, IgD or IgE molecule; known in the art) or of a Fab fragment, a $F(ab')_2$ fragment, an Fv fragment such as a disulphide linked Fv or a scFv fragment, or a diabody (all known in the art) derived from such conventional 4-chain antibody, would normally not be regarded as an ISVD as, in these cases, binding to the respective epitope of an antigen would normally not occur by one single immunoglobulin domain but by a pair of associating immunoglobulin domains such as light and heavy chain variable domains, i.e., by a $V_H$-$V_L$ pair of immunoglobulin domains, which jointly bind to an epitope of the respective antigen.

In contrast, ISVDs are capable of specifically binding to an epitope of the antigen without pairing with an additional immunoglobulin variable domain. The binding site of an ISVD is formed by a single $V_H$, a single $V_{HH}$ or single $V_L$ domain.

As such, the ISVD may be a light chain variable domain sequence (e.g., a $V_L$-sequence) or a suitable fragment thereof; or a heavy chain variable domain sequence (e.g., a $V_H$-sequence or $V_{HH}$ sequence) or a suitable fragment thereof; as long as it is capable of forming a single antigen binding unit; i.e., a functional antigen binding unit that essentially consists of the ISVD, such that the single antigen binding domain does not need to interact with another variable domain to form a functional antigen binding unit.

An ISVD can for example be a heavy chain ISVD, such as a $V_H$, $V_{HH}$, including a camelized $V_H$ or humanized $V_{HH}$. In one embodiment, it is a $V_{HH}$, including a camelized $V_H$ or humanized $V_{HH}$. Heavy chain ISVDs can be derived from a conventional four-chain antibody or from a heavy chain antibody.

For example, the ISVD may be a single domain antibody (or an amino acid sequence that is suitable for use as a single domain antibody), a "dAb" or dAb (or an amino acid sequence that is suitable for use as a dAb) or a Nanobody® (as defined herein, and including but not limited to a $V_{HH}$); other single variable domains, or any suitable fragment of any one thereof.

In particular, the ISVD may be a Nanobody® (such as a $V_{HH}$, including a humanized $V_{HH}$ or camelized $V_H$) or a suitable fragment thereof. Nanobody® Nanobodies® and Nanoclone® are registered trademarks.

"$V_{HH}$ domains", also known as $V_{HH}$5, $V_{HH}$ antibody fragments, and $V_{HH}$ antibodies, have originally been described as the antigen binding immunoglobulin variable domain of "heavy chain antibodies"; i.e. of "antibodies devoid of light chains", see Hamers-Casterman et al. Nature 363: 446-448, 1993. The term "$V_{HH}$ domain" has been chosen in order to distinguish these variable domains from the heavy chain variable domains that are present in conventional 4-chain antibodies, which are referred to herein as "$V_H$ domains", and from the light chain variable domains that are present in conventional 4-chain antibodies, which are referred to herein as "$V_L$ domains". For a further description of $V_{HH}$'s, reference is made to the review article by Muyldermans (Reviews in Molecular Biotechnology 74: 277-302, 2001).

Typically, the generation of immunoglobulins involves the immunization of experimental animals, fusion of immunoglobulin producing cells to create hybridomas and screening for the desired specificities. Alternatively, immunoglobulins can be generated by screening of naïve, immune or synthetic libraries e.g. by phage display.

The generation of immunoglobulin sequences, such as Nanobodies®, has been described extensively in various publications, among which WO 94/04678, Hamers-Casterman et al. 1993 (Nature 363: 446-448, 1993) and Muyldermans et al. 2001 (Reviews in Molecular Biotechnology 74: 277-302, 2001) can be exemplified. In these methods, camelids are immunized with the target antigen in order to induce an immune response against said target antigen. The repertoire of Nanobodies® obtained from said immunization is further screened for Nanobodies® that bind the target antigen.

In these instances, the generation of antibodies requires purified antigen for immunization and/or screening. Antigens can be purified from natural sources, or in the course of recombinant production.

Immunization and/or screening for immunoglobulin sequences can be performed using peptide fragments of such antigens.

The present technology may use immunoglobulin sequences of different origin, comprising mouse, rat, rabbit, donkey, human and camelid immunoglobulin sequences. The present technology also includes fully human, humanized or chimeric sequences. For example, the present technology comprises camelid immunoglobulin sequences and humanized camelid immunoglobulin sequences, or camelized domain antibodies, e.g. camelized dAb as described by Ward et al. (Nature 341: 544, 1989) (see for example WO 94/04678 and Davies and Riechmann, Febs Lett., 339:285-290, 1994 and Prot. Eng., 9:531-537, 1996). Moreover, the present technology also uses fused immunoglobulin sequences, e.g. forming a multivalent and/or multispecific construct (for multivalent and multispecific polypeptides containing one or more $V_{HH}$ domains and their preparation, reference is also made to Conrath et al., J. Biol. Chem., Vol. 276, 10. 7346-7350, 2001, as well as to for example WO 96/34103 and WO 99/23221), and immunoglobulin sequences comprising tags or other functional moieties, e.g. toxins, labels, radiochemicals, etc., which are derivable from the immunoglobulin sequences of the present technology.

A "humanized $V_{HH}$" comprises an amino acid sequence that corresponds to the amino acid sequence of a naturally occurring $V_{HH}$ domain, but that has been "humanized", i.e. by replacing one or more amino acid residues in the amino acid sequence of said naturally occurring $V_{HH}$ sequence (and in particular in the framework sequences) by one or more of the amino acid residues that occur at the corresponding position(s) in a $V_H$ domain from a conventional 4-chain antibody from a human being (e.g. indicated above). This can be performed in a manner known per se, which will be clear to the skilled person, for example on the basis of the further description herein and the prior art (e.g. WO 2008/020079). Again, it should be noted that such humanized $V_{HH}$s can be obtained in any suitable manner known per se and thus are not strictly limited to polypeptides that have been obtained using a polypeptide that comprises a naturally occurring $V_{HH}$ domain as a starting material.

A "camelized $V_H$" comprises an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the further description herein and the prior art (e.g. WO 2008/020079). Such "camelizing" substitutions are usually inserted at amino acid positions that form and/or are present at the $V_H$-$V_L$ interface, and/or at the so-called Camelidae hallmark residues, as defined herein (see for example WO 94/04678 and Davies and Riechmann, 1994 and 1996, supra). In one embodiment, the $V_H$ sequence that is used as a starting material or starting point for generating or designing the camelized $V_H$ is a $V_H$ sequence from a mammal, or the $V_H$ sequence of a human being, such as a $V_H3$ sequence. However, it should be noted that such camelized $V_H$ can be obtained in any suitable manner known per se and thus are not strictly limited to polypeptides that have been obtained using a polypeptide that comprises a naturally occurring $V_H$ domain as a starting material.

The structure of an ISVD sequence can be considered to be comprised of four framework regions ("FRs"), which are referred to in the art and herein as "Framework region 1" ("FR1"); as "Framework region 2" ("FR2"); as "Framework region 3" ("FR3"); and as "Framework region 4" ("FR4"), respectively; which framework regions are interrupted by three complementary determining regions ("CDRs"), which are referred to in the art and herein as "Complementarity Determining Region 1" ("CDR1"); as "Complementarity Determining Region 2" ("CDR2"); and as "Complementarity Determining Region 3" ("CDR3"), respectively.

As further described in paragraph q) on pages 58 and 59 of WO 08/020079, the amino acid residues of an ISVD can be numbered according to the general numbering for $V_H$ domains given by Kabat et al. ("Sequence of proteins of immunological interest", US Public Health Services, NIH Bethesda, MD, Publication No. 91), as applied to $V_{HH}$ domains from Camelids in the article of Riechmann and Muyldermans, 2000 (J. Immunol. Methods 240 (1-2): 185-195; see for example FIG. 2 of this publication). It should be noted that—as is well known in the art for $V_H$ domains and for $V_{HH}$ domains—the total number of amino acid residues in each of the CDRs may vary and may not correspond to the total number of amino acid residues indicated by the Kabat numbering. That is, one or more positions according to the Kabat numbering may not be occupied in the actual sequence, or the actual sequence may contain more amino acid residues than the number allowed for by the Kabat numbering. This means that, generally, the numbering according to Kabat may or may not correspond to the actual numbering of the amino acid residues in the actual sequence. The total number of amino acid residues in a $V_H$ domain and a $V_{HH}$ domain will usually be in the range of from 110 to 120, often between 112 and 115. It should however be noted that smaller and longer sequences may also be suitable for the purposes described herein.

In the present application, unless indicated otherwise, CDR sequences were determined according to the AbM numbering as described in Kontermann and Dübel (Eds. 2010, Antibody Engineering, vol 2, Springer Verlag Heidelberg Berlin, Martin, Chapter 3, pp. 33-51). According to this method, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113.

Determination of CDR regions may also be done according to different methods. In the CDR determination according to Kabat, FR1 of an ISVD comprises the amino acid residues at positions 1-30, CDR1 of an ISVD comprises the amino acid residues at positions 31-35, FR2 of an ISVD comprises the amino acids at positions 36-49, CDR2 of an ISVD comprises the amino acid residues at positions 50-65, FR3 of an ISVD comprises the amino acid residues at positions 66-94, CDR3 of an ISVD comprises the amino acid residues at positions 95-102, and FR4 of an ISVD comprises the amino acid residues at positions 103-113.

In such an immunoglobulin sequence, the framework sequences may be any suitable framework sequences, and examples of suitable framework sequences will be clear to the skilled person, for example on the basis the standard handbooks and the further disclosure and prior art mentioned herein.

The framework sequences are a suitable combination of immunoglobulin framework sequences or framework sequences that have been derived from immunoglobulin framework sequences, for example by humanization or camelization. For example, the framework sequences may be framework sequences derived from a light chain variable domain (e.g. a $V_L$-sequence) and/or from a heavy chain variable domain (e.g. a $V_H$-sequence or $V_{HH}$ sequence). In one aspect, the framework sequences are either framework sequences that have been derived from a $V_{HH}$-sequence in which said framework sequences may optionally have been partially or fully humanized or are conventional $V_H$ sequences that have been camelized (as defined herein).

In particular, the framework sequences present in the ISVD sequence used in the present technology may contain one or more of Hallmark residues (as defined herein), such that the ISVD sequence is a Nanobody®, such as a $V_{HH}$, including a humanized $V_{HH}$ or camelized $V_H$. Some non-limiting examples of suitable combinations of such framework sequences will become clear from the further disclosure herein.

Again, as generally described herein for the immunoglobulin sequences, it is also possible to use suitable fragments or combinations of fragments of any of the foregoing, such as fragments that contain one or more CDR sequences, suitably flanked by and/or linked via one or more framework sequences; for example, in the same order as these CDR's and framework sequences may occur in the full-sized immunoglobulin sequence from which the fragment has been derived.

However, it should be noted that the present technology is not limited as to the origin of the ISVD sequence or the origin of the nucleotide sequence used to express it, nor as to the way that the ISVD sequence or nucleotide sequence is or has been generated or obtained. Thus, the ISVD sequences may be naturally occurring sequences (from any suitable species) or synthetic or semi-synthetic sequences. In a specific but non-limiting aspect, the ISVD sequence is a naturally occurring sequence (from any suitable species) or a synthetic or semi-synthetic sequence, including but not limited to "humanized" (as defined herein) immunoglobulin sequences (such as partially or fully humanized mouse or rabbit immunoglobulin sequences, and in particular partially or fully humanized $V_{HH}$ sequences), "camelized" (as defined herein) immunoglobulin sequences, as well as immunoglobulin sequences that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing.

Similarly, nucleotide sequences may be naturally occurring nucleotide sequences or synthetic or semi-synthetic sequences, and may for example be sequences that are isolated by PCR from a suitable naturally occurring template, e.g. DNA or RNA isolated from a cell, nucleotide sequences that have been isolated from a library (and in particular, an expression library), nucleotide sequences that have been prepared by introducing mutations into a naturally occurring nucleotide sequence (using any suitable technique known per se, such as mismatch PCR), nucleotide sequence that have been prepared by PCR using overlapping primers, or nucleotide sequences that have been prepared using techniques for DNA synthesis known per se.

As described above, an ISVD may be a Nanobody® or a suitable fragment thereof. For a general description of Nanobodies®, reference is made to the further description below, as well as to the prior art cited herein. In this respect, it should however be noted that this description and the prior art mainly described Nanobodies® of the so-called "$V_H3$ class", i.e. Nanobodies® with a high degree of sequence homology to human germline sequences of the $V_H3$ class such as DP-47, DP-51 or DP-29. It should however be noted that the present technology in its broadest sense can generally use any type of Nanobody®, and for example also uses the Nanobodies® belonging to the so-called "$V_H4$ class", i.e. Nanobodies® with a high degree of sequence homology to human germline sequences of the $V_H4$ class such as DP-78, as for example described in WO 2007/118670.

Generally, Nanobodies® (in particular $V_{HH}$ sequences, including (partially) humanized $V_{HH}$ sequences and camelized $V_H$ sequences) can be characterized by the presence of one or more "Hallmark residues" (as described herein) in one or more of the framework sequences (again as further described herein). Thus, generally, a Nanobody® can be defined as an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which one or more of the Hallmark residues are as further defined herein.

In particular, a Nanobody® can be an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which the framework sequences are as further defined herein.

More in particular, a Nanobody® can be an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

one or more of the amino acid residues at positions 11, 37, 44, 45, 47, 83, 84, 103, 104 and 108 according to the Kabat numbering are chosen from the Hallmark residues mentioned in Table A-6 below.

TABLE A-6

Hallmark Residues in Nanobodies

| Position | Human $V_H$3 | Hallmark Residues |
|---|---|---|
| 11 | L, V; predominantly L | L, S, V, M, W, F, T, Q, E, A, R, G, K, Y, N, P, I; preferably L |
| 37 | V, I, F; usually V | F[(1)], Y, V, L, A, H, S, I, W, C, N, G, D, T, P, preferably F[(1)] or Y |
| 44[(8)] | G | E[(3)], Q[(3)], G[(2)], D, A, K, R, L, P, S, V, H, T, N, W, M, I; preferably G[(2)], E[(3)] or Q[(3)]; most preferably G[(2)] or Q[(3)] |
| 45[(8)] | L | L[(2)], R[(3)], P, H, F, G, Q, S, E, T, Y, C, I, D, V; preferably L[(2)] or R[(3)] |
| 47[(8)] | W, Y | F[(1)], L[(1)] or W[(2)] G, I, S, A, V, M, R, Y, E, P, T, C, H, K, Q, N, D; preferably W[(2)], L[(1)] or F[(1)] |
| 83 | R or K; usually R | R, K[(5)], T, E[(5)], Q, N, S, I, V, G, M, L, A, D, Y, H; preferably K or R; most preferably K |
| 84 | A, T, D; predominantly A | P[(5)], S, H, L, A, V, I, T, F, D, R, Y, N, Q, G, E; preferably P |
| 103 | W | W[(4)], R[(6)], G, S, K, A, M, Y, L, F, T, N, V, Q, P[(6)], E, C; preferably W |
| 104 | G | G, A, S, T, D, P, N, E, C, L; preferably G |
| 108 | L, M or T; predominantly L | Q, L[(7)], R, P, E, K, S, T, M, A, H; preferably Q or L[(7)] |

Notes:

(1)In particular, but not exclusively, in combination with KERE or KQRE at positions 43-46.

(2)Usually as GLEW at positions 44-47.

(3)Usually as KERE or KQRE at positions 43-46, e.g. as KEREL, KEREF, KQREL, KQREF, KEREG, KQREW or KQREG at positions 43-47. Alternatively, also sequences such as TERE (for example TEREL), TQRE (for example TQREL), KECE (for example KECEL or KECER), KQCE (for example KQCEL), RERE (for example REREG), RQRE (for example RQREL, RQREF or RQREW), QERE (for example QEREG), QQRE, (for example QQREW, QQREL or QQREF), KGRE (for example KGREG), KDRE (for example KDREV) are possible. Some other possible, but less preferred sequences include for example DECKL and NVCEL.

(4)With both GLEW at positions 44-47 and KERE or KQRE at positions 43-46.

(5)Often as KP or EP at positions 83-84 of naturally occurring $V_{HH}$ domains.

(6)In particular, but not exclusively, in combination with GLEW at positions 44-47.

(7)With the proviso that when positions 44-47 are GLEW, position 108 is always Q in (non-humanized) $V_{HH}$ sequences that also contain a W at 103.

(8)The GLEW group also contains GLEW-like sequences at positions 44-47, such as for example GVEW, EPEW, GLER, DQEW, DLEW, GIEW, ELEW, GPEW, EWLP, GPER, GLER and ELEW.

The present technology inter alia uses ISVDs that can bind to TNFα or the p19 subunit of IL-23. In the context of the present technology, "binding to" a certain target molecule has the usual meaning in the art as understood in the context of antibodies and their respective antigens.

The polypeptide of the present technology may comprise one or more ISVDs binding to TNFα and two or more ISVDs binding to IL-23. For example, the polypeptide may comprise one ISVD that binds to TNFα and two ISVDs that bind to the p19 subunit of IL-23.

In some embodiments, at least one ISVD can functionally block its target molecule. For example, the ISVD can block the interaction between TNFα and TNFR (TNF receptor) or can block the interaction between IL-23 and IL-23R (IL-23 receptor). In the polypeptide of the present technology at least one ISVD can functionally block IL-23, for example by blocking the interaction between IL-23 and IL-23R and/or inhibiting IL-23-induced release of IL-22. Accordingly, in one embodiment, the polypeptide of the present technology comprises one ISVD that binds to TNFα and functionally blocks TNFα and two ISVDs that bind to IL-23, one of which can functionally block IL-23.

The ISVDs used in the present technology form part of a polypeptide of the present technology, which comprises or consists of at least three ISVDs, such that the polypeptide can specifically bind to TNFα and IL-23.

Accordingly, the target molecules for the at least three ISVDs as used in the polypeptide of the present technology are TNFα and IL-23. Examples are mammalian TNFα and IL-23. Besides human TNFα (Uniprot accession P01375) and human IL-23 (Uniprot accession for p19 subunit, IL-23A: Q9NPF7), the versions from other species are also amenable to the present technology, for example TNFα and IL-23 from mice, rats, rabbits, cats, dogs, goats, sheep, horses, pigs, non-human primates, such as cynomolgus monkeys (also referred to herein as "cyno"), or camelids, such as llama or alpaca.

Specific examples of ISVDs specifically binding to TNFα or the p19 subunit of IL-23 that can be used in the present technology are as described in the following items A to C:

A. An ISVD that specifically binds to human TNFα and comprises
   i. a CDR1 that is the amino acid sequence of SEQ ID NO: 6 or an amino acid sequence with 2 or 1 amino acid difference with SEQ ID NO: 6;
   ii. a CDR2 that is the amino acid sequence SEQ ID NO: 10 or an amino acid sequence with 2 or 1 amino acid difference with SEQ ID NO: 10; and
   iii. a CDR3 that is the amino acid sequence of SEQ ID NO: 14 or an amino acid sequence with 2 or 1 amino acid difference with SEQ ID NO: 14.

In one embodiment, the ISVD comprises a CDR1 that is the amino acid sequence of SEQ ID NO: 6, a CDR2 that is the amino acid sequence of SEQ ID NO: 10 and a CDR3 that is the amino acid sequence of SEQ ID NO: 14.

Examples of such an ISVD that specifically binds to human TNFα have one or more, or all, framework regions as indicated for construct 6C11 in Table A-2 (in addition to the CDRs as defined in the preceding item A). In one embodiment, it is an ISVD comprising or consisting of the full amino acid sequence of construct 6C11 (SEQ ID NO: 2, see Table A-1 and A-2).

In another embodiment, the amino acid sequence of the ISVD specifically binding to human TNFα may have a sequence identity of more than 90%, such as more than 95% or more than 99%, with SEQ ID NO: 2, wherein the CDRs are as defined in the preceding item A. In one embodiment, the ISVD specifically binding to TNFα comprises or consists of the amino acid sequence of SEQ ID NO: 2.

When such an ISVD specifically binding to TNFα has 2 or 1 amino acid difference in at least one CDR relative to a corresponding reference CDR sequence (item A above), the ISVD has at least half the binding affinity, or at least the same binding affinity, to human TNFα compared to construct 6C11 (SEQ ID NO: 2), wherein the binding affinity is measured using the same method, such as SPR.

B. An ISVD that specifically binds to the p19 subunit of human IL-23 and comprises
   i. a CDR1 that is the amino acid sequence SEQ ID NO: 7 or an amino acid sequence with 2 or 1 amino acid difference with SEQ ID NO: 7;
   ii. a CDR2 that is the amino acid sequence SEQ ID NO: 11 or an amino acid sequence with 2 or 1 amino acid difference with SEQ ID NO: 11; and
   iii. a CDR3 that is the amino acid sequence SEQ ID NO: 15 or an amino acid sequence with 2 or 1 amino acid difference with SEQ ID NO: 15.

In one embodiment, the ISVD comprises a CDR1 that is the amino acid sequence of SEQ ID NO: 7, a CDR2 that is the amino acid sequence of SEQ ID NO: 11 and a CDR3 that is the amino acid sequence of SEQ ID NO: 15.

Examples of such an ISVD that specifically binds to human IL-23 have one or more, or all, framework regions as indicated for construct 119A03/1 in Table A-2 (in addition to the CDRs as defined in the preceding item B). In one embodiment, it is an ISVD comprising or consisting of the full amino acid sequence of construct 119A03/1 (SEQ ID NO: 3, see Table A-1 and A-2).

Also, in another embodiment, the amino acid sequence of an ISVD specifically binding to human IL-23 may have a sequence identity of more than 90%, such as more than 95% or more than 99%, with SEQ ID NO: 3, wherein the CDRs are as defined in the preceding item B. In one embodiment, the ISVD binding to IL-23 comprises or consists of the amino acid sequence of SEQ ID NO: 3.

When such an ISVD binding to IL-23 has 2 or 1 amino acid difference in at least one CDR relative to a corresponding reference CDR sequence (item B above), the ISVD has at least half the binding affinity, or at least the same binding affinity, to human IL-23 compared to construct 119A03/1 (SEQ ID NO: 3), wherein the binding affinity is measured using the same method, such as SPR.

In one embodiment, an ISVD comprising a CDR2, which has 2 or 1 amino acid difference with SEQ ID NO: 11 (TIESGSRTN), does not have an E to N substitution at amino acid position 3 of the CDR2 sequence and/or does not have a N to Y substitution at amino acid position 9 of the CDR2 sequence. In another embodiment such ISVD does not have an E to N substitution at amino acid position 3 of the CDR2 sequence and does not have a N to Y substitution at amino acid position 9 of the CDR2 sequence. In such embodiments of an ISVD comprising a CDR2, which has 2 or 1 amino acid difference with SEQ ID NO: 11 (TIESGSRTN), E is maintained as amino acid at position 3 and/or N is maintained as amino acid at position 9 of said CDR2 sequence. In another embodiment, both E at amino acid position 3 and N at amino acid position 9 of said CDR2 sequence are maintained. Using an ISVD comprising an N at amino acid position 3 of said CDR2 sequence may result in reduced amino acid sequence stability during production of the polypeptide, e.g. due to deamination, compared to the same polypeptide not comprising N at said amino acid position, and especially compared to the same polypeptide comprising an E at said amino acid position. Using an ISVD comprising a Y at amino acid position 9 of said CDR2 sequence may result in increased protein aggregation of the polypeptide compared to the same polypeptide not comprising Y at said amino acid position, and especially compared to the same polypeptide comprising an N at said amino acid position.

C. An ISVD that specifically binds to the p19 subunit of human IL-23 and comprises
   i. a CDR1 that is the amino acid sequence of SEQ ID NO: 9 or an amino acid sequence with 2 or 1 amino acid difference with SEQ ID NO: 9;
   ii. a CDR2 that is the amino acid sequence of SEQ ID NO: 13 or an amino acid sequence with 2 or 1 amino acid difference with SEQ ID NO: 13; and
   iii. a CDR3 that is the amino acid sequence of SEQ ID NO: 17 or an amino acid sequence with 2 or 1 amino acid difference with SEQ ID NO: 17.

In one embodiment, the ISVD comprises a CDR1 that is the amino acid sequence of SEQ ID NO: 9, a CDR2 that is the amino acid sequence of SEQ ID NO: 13 and a CDR3 that is the amino acid sequence of SEQ ID NO: 17.

Examples of such an ISVD that specifically binds to human IL-23 have one or more, or all, framework regions as indicated for construct 81A12 in Table A-2 (in addition to the CDRs as defined in the preceding item C). In one embodiment it is an ISVD comprising or consisting of the full amino acid sequence of construct 81A12 (SEQ ID NO: 5, see Table A-1 and A-2).

Also, in another embodiment, the amino acid sequence of an ISVD specifically binding to human IL-23 may have a sequence identity of more than 90%, such as more than 95% or more than 99%, with SEQ ID NO: 5, wherein the CDRs are as defined in the preceding item C. In one embodiment, the ISVD binding to IL-23 comprises or consists of the amino acid sequence of SEQ ID NO: 5.

When such an ISVD specifically binding to IL-23 has 2 or 1 amino acid difference in at least one CDR relative to a corresponding reference CDR sequence (item C above), the ISVD has at least half the binding affinity, or at least the same binding affinity, to human IL-23 compared to construct 81A12 (SEQ ID NO: 5), wherein the binding affinity is measured using the same method, such as SPR.

In an embodiment, each of the ISVDs as defined under items A to C above is comprised in the polypeptide of the present technology. Such a polypeptide of the present technology comprising each of the ISVDs as defined under items A to C above has at least half the binding affinity, or at least the same binding affinity, to human TNFα and to human IL-23 compared to a polypeptide consisting of the amino acid of SEQ ID NO: 1, wherein the binding affinity is measured using the same method, such as SPR.

The SEQ ID NOs referred to in the above items A to C are based on the CDR definition according to the AbM definition (see Table A-2). It is noted that the SEQ ID NOs defining the same CDRs according to the Kabat definition (see Table A-2.1) can likewise be used in the above items A to C.

Accordingly, the specific ISVDs specifically binding to TNFα or the p19 subunit of IL-23 that can be used in the present technology as described above using the AbM definition can be also described using the Kabat definition as set forth in items A' to C' below:

A'. An ISVD that specifically binds to human TNFα and comprises
- i. a CDR1 that is the amino acid sequence of SEQ ID NO: 122 or an amino acid sequence with 2 or 1 amino acid difference with SEQ ID NO: 122;
- ii. a CDR2 that is the amino acid sequence SEQ ID NO: 130 or an amino acid sequence with 2 or 1 amino acid difference with SEQ ID NO: 130; and
- iii. a CDR3 that is the amino acid sequence of SEQ ID NO: 138 or an amino acid sequence with 2 or 1 amino acid difference with SEQ ID NO: 138.

In one embodiment, the ISVD comprises a CDR1 that is the amino acid sequence of SEQ ID NO: 122, a CDR2 that is the amino acid sequence of SEQ ID NO: 130 and a CDR3 that is the amino acid sequence of SEQ ID NO: 138.

Examples of such an ISVD that specifically binds to human TNFα have one or more, or all, framework regions as indicated for construct 6C11 in Table A-2.1 (in addition to the CDRs as defined in the preceding item A'). In one embodiment, it is an ISVD comprising or consisting of the full amino acid sequence of construct 6C11 (SEQ ID NO: 2, see Table A-1 and A-2.1).

Also, in another embodiment, the amino acid sequence of the ISVD specifically binding to human TNFα may have a sequence identity of more than 90%, such as more than 95% or more than 99%, with SEQ ID NO: 2, wherein the CDRs are as defined in the preceding item A'. In one embodiment, the ISVD specifically binding to TNFα comprises or consists of the amino acid sequence of SEQ ID NO: 2.

When such an ISVD specifically binding to TNFα has 2 or 1 amino acid difference in at least one CDR relative to a corresponding reference CDR sequence (item A' above), the ISVD has at least half the binding affinity, or at least the same binding affinity, to human TNFα compared to construct 6C11 (SEQ ID NO: 2), wherein the binding affinity is measured using the same method, such as SPR.

B'. An ISVD that specifically binds to the p19 subunit of human IL-23 and comprises
- i. a CDR1 that is the amino acid sequence SEQ ID NO: 123 or an amino acid sequence with 2 or 1 amino acid difference with SEQ ID NO: 123;
- ii. a CDR2 that is the amino acid sequence SEQ ID NO: 131 or an amino acid sequence with 2 or 1 amino acid difference with SEQ ID NO: 131; and
- iii. a CDR3 that is the amino acid sequence SEQ ID NO: 139 or an amino acid sequence with 2 or 1 amino acid difference with SEQ ID NO: 139.

In one embodiment, the ISVD comprises a CDR1 that is the amino acid sequence of SEQ ID NO: 123, a CDR2 that is the amino acid sequence of SEQ ID NO: 131 and a CDR3 that is the amino acid sequence of SEQ ID NO: 139.

Examples of such an ISVD that specifically binds to human IL-23 have one or more, or all, framework regions as indicated for construct 119A03/1 in Table A-2.1 (in addition to the CDRs as defined in the preceding item B'). In one embodiment, it is an ISVD comprising or consisting of the full amino acid sequence of construct 119A03/1 (SEQ ID NO: 3, see Table A-1 and A-2.1).

Also, in another embodiment, the amino acid sequence of an ISVD specifically binding to human IL-23 may have a sequence identity of more than 90%, such as more than 95% or more than 99%, with SEQ ID NO: 3, wherein the CDRs are as defined in the preceding item B'. In one embodiment, the ISVD binding to IL-23 comprises or consists of the amino acid sequence of SEQ ID NO: 3.

When such an ISVD binding to IL-23 has 2 or 1 amino acid difference in at least one CDR relative to a corresponding reference CDR sequence (item B' above), the ISVD has at least half the binding affinity, or at least the same binding affinity, to human IL-23 compared to construct 119A03/1 (SEQ ID NO: 3), wherein the binding affinity is measured using the same method, such as SPR.

In one embodiment, an ISVD comprising a CDR2, comprising or consisting of an amino acid sequence with 2 or 1 amino acid difference with SEQ ID NO: 131 (TIESGSRTNYADSVKG), does not have an E to N substitution at amino acid position 3 and/or does not have a N to Y substitution at amino acid position 9 of said CDR2 sequence. In another embodiment, such ISVD does not have an E to N substitution at amino acid position 3 of the CDR2 sequence and does not have a N to Y substitution at amino acid position 9 of the CDR2 sequence. In such embodiments of an ISVD comprising a CDR2, comprising or consisting of an amino acid sequence with 2 or 1 amino acid difference with SEQ ID NO: 131 (TIESGSRTNYADSVKG), E is maintained as amino acid at position 3 and/or N is maintained as amino acid at position 9 of said CDR2 sequence. In another embodiment, both E at amino acid position 3 and N at amino acid position 9 of said CDR2 sequence are maintained. Using an ISVD comprising an N at amino acid position 3 of said CDR2 sequence may result in reduced amino acid sequence stability during production of the polypeptide, e.g. due to deamination, compared to the same polypeptide not comprising N at said amino acid position, and especially compared to the same polypeptide comprising an E at said amino acid position. Using an ISVD comprising a Y at amino acid position 9 of said CDR2 sequence may result in increased protein aggregation of the polypeptide compared to the same polypeptide not comprising Y at said amino acid position, and especially compared to the same polypeptide comprising an N at said amino acid position.

C'. An ISVD that specifically binds to the p19 subunit of human IL-23 and comprises
- i. a CDR1 that is the amino acid sequence of SEQ ID NO: 125 or an amino acid sequence with 2 or 1 amino acid difference with SEQ ID NO: 125;
- ii. a CDR2 that is the amino acid sequence of SEQ ID NO: 133 or an amino acid sequence with 2 or 1 amino acid difference with SEQ ID NO: 133; and
- iii. a CDR3 that is the amino acid sequence of SEQ ID NO: 141 or an amino acid sequence with 2 or 1 amino acid difference with SEQ ID NO: 141.

In one embodiment, the ISVD comprises a CDR1 that is the amino acid sequence of SEQ ID NO: 125, a CDR2 that is the amino acid sequence of SEQ ID NO: 133 and a CDR3 that is the amino acid sequence of SEQ ID NO: 141.

Examples of such an ISVD that specifically binds to human IL-23 have one or more, or all, framework regions as indicated for construct 81A12 in Table A-2.1 (in addition to the CDRs as defined in the preceding item C'). In one embodiment, it is an ISVD comprising or consisting of the full amino acid sequence of construct 81A12 (SEQ ID NO: 5, see Table A-1 and A-2.1).

Also, in another embodiment, the amino acid sequence of an ISVD specifically binding to human IL-23 may have a sequence identity of more than 90%, such as more than 95% or more than 99%, with SEQ ID NO: 5, wherein the CDRs are as defined in the preceding item C'. In one embodiment, the ISVD binding to IL-23 comprises or consists of the amino acid sequence of SEQ ID NO: 5.

When such an ISVD specifically binding to IL-23 has 2 or 1 amino acid difference in at least one CDR relative to a corresponding reference CDR sequence (item C' above), the ISVD has at least half the binding affinity, or at least the same binding affinity, to human IL-23 compared to construct 81A12 (SEQ ID NO: 5), wherein the binding affinity is measured using the same method, such as SPR.

In an embodiment, each of the ISVDs as defined under items A' to C' above is comprised in the polypeptide of the present technology. Such a polypeptide of the present technology comprising each of the ISVDs as defined under items A' to C' above has at least half the binding affinity, or at least the same binding affinity, to human TNFα and to human IL-23 compared to a polypeptide consisting of the amino acid of SEQ ID NO: 1, wherein the binding affinity is measured using the same method, such as SPR.

The percentage of "sequence identity" between a first amino acid sequence and a second amino acid sequence may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (i.e. at a single position).

Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

An "amino acid difference" as used herein refers to a deletion, insertion or substitution of a single amino acid residue vis-à-vis a reference sequence. In one embodiment, an "amino acid difference" is a substitution.

In one embodiment, amino acid substitutions are conservative substitutions. Such conservative substitutions are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp.

In one embodiment, conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

5.2 Specificity

The terms "specificity", "binding specifically" or "specific binding" refer to the number of different target molecules, such as antigens, from the same organism to which a particular binding unit, such as an ISVD, can bind with sufficiently high affinity (see below). "Specificity", "binding specifically" or "specific binding" are used interchangeably herein with "selectivity", "binding selectively" or "selective binding". Binding units, such as ISVDs, specifically bind to their designated targets.

The specificity/selectivity of a binding unit can be determined based on affinity. The affinity denotes the strength or stability of a molecular interaction. The affinity is commonly given by the KD, or dissociation constant, which has units of mol/liter (or M). The affinity can also be expressed as an association constant, KA, which equals 1/KD and has units of $(\text{mol/liter})^{-1}$ (or $M^{-1}$).

The affinity is a measure for the binding strength between a moiety and a binding site on the target molecule: the lower the value of the KD, the stronger the binding strength between a target molecule and a targeting moiety.

Typically, binding units used in the present technology, such as ISVDs, will bind to their targets with a dissociation constant (KD) of $10^{-5}$ to $10^{-12}$ moles/liter or less, $10^{-7}$ to $10^{-12}$ moles/liter or less, or $10^{-8}$ to $10^{-12}$ moles/liter (i.e. with an association constant (KA) of $10^{5}$ to $10^{12}$ liter/moles or more, 10' to $10^{12}$ liter/moles or more, or $10^{8}$ to $10^{12}$ liter/moles).

Any KD value greater than $10^{-4}$ mol/liter (or any KA value lower than $10^{4}$ liters/mol) is generally considered to indicate non-specific binding.

The KD for biological interactions, such as the binding of immunoglobulin sequences to an antigen, which are considered specific are typically in the range of $10^{-5}$ moles/liter (10000 nM or 10 μM) to $10^{-12}$ moles/liter (0.001 nM or 1 pM) or less.

Accordingly, specific/selective binding may mean that-using the same measurement method, e.g. SPR-a binding unit (or polypeptide comprising the same) binds to TN Fa and/or IL-23 with a KD value of $10^{-5}$ to $10^{-12}$ moles/liter or less and binds to related cytokines with a KD value greater than $10^{-4}$ moles/liter. An example of a related cytokine for IL-23 is IL-12, as it shares the p40 subunit with IL-23. Examples of related cytokines for TNFα are TNF superfamily members FASL, TNFβ, LIGHT, TL-1A, RANKL. Thus, in an embodiment of the present technology, at least one ISVD comprised in the polypeptide binds to (human) TNFα with a KD value of $10^{-5}$ to $10^{-12}$ moles/liter or less and binds to FASL, TNFβ, LIGHT, TL-1A, RANKL of the same species with a KD value greater than $10^{-4}$ moles/liter, and at least two ISVDs comprised in the polypeptide bind to IL-23 with a KD value of $10^{-5}$ to $10^{-12}$ moles/liter or less and bind to IL-12 of the same species with a KD value greater than $10^{-4}$ moles/liter.

Thus, the polypeptide of the present technology has at least half the binding affinity, or at least the same binding affinity, to human TNFα and to human IL-23 as compared to a polypeptide consisting of the amino acid of SEQ ID NO: 1, wherein the binding affinity is measured using the same method, such as SPR.

Specific binding to a certain target from a certain species does not exclude that the binding unit can also specifically bind to the analogous target from a different species. For example, specific binding to human TNFα does not exclude that the binding unit or a polypeptide comprising the same can also specifically bind to TN Fa from cynomolgus monkeys. Likewise, for example, specific binding to human IL-23 does not exclude that the binding unit or a polypeptide comprising the same can also specifically bind to IL-23 from cynomolgus monkeys ("cyno").

Specific binding of a binding unit to its designated target can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person. Methods for determining the dissociation constant will be clear to the skilled person, and for example include the techniques mentioned below. In this respect, it will also be clear that it may not be possible to measure dissociation constants of more than $10^{-4}$ moles/liter or $10^{-3}$ moles/liter (e.g. of $10^{-2}$ moles/liter). Optionally, as will also be clear to the skilled person, the (actual or apparent) dissociation constant may be calculated on the basis of the (actual or apparent) association constant (KA), by means of the relationship [KD=1/KA].

The affinity of a molecular interaction between two molecules can be measured via different techniques known per se, such as the well-known surface plasmon resonance (SPR) biosensor technique (see for example Ober et al. 2001, Intern. Immunology 13: 1551-1559). The term "surface plasmon resonance", as used herein, refers to an optical phenomenon that allows for the analysis of real-time biospecific interactions by detection of alterations in protein concentrations within a biosensor matrix, where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIAcore® system (BIAcore International AB, a GE Healthcare company, Uppsala, Sweden and Piscataway, NJ). For further descriptions, see Jonsson et al. (1993, Ann. Biol. Clin. 51: 19-26), Jonsson et al. (1991 Biotechniques 11: 620-627), Johnsson et al. (1995, J. Mol. Recognit. 8: 125-131), and Johnnson et al. (1991, Anal. Biochem. 198: 268-277).

Another well-known biosensor technique to determine affinities of biomolecular interactions is bio-layer interferometry (BLI) (see for example Abdiche et al. 2008, Anal. Biochem. 377: 209-217). The term "bio-layer Interferometry" or "BLI", as used herein, refers to a label-free optical technique that analyzes the interference pattern of light reflected from two surfaces: an internal reference layer (reference beam) and a layer of immobilized protein on the biosensor tip (signal beam). A change in the number of molecules bound to the tip of the biosensor causes a shift in the interference pattern, reported as a wavelength shift (nm), the magnitude of which is a direct measure of the number of molecules bound to the biosensor tip surface. Since the interactions can be measured in real-time, association and dissociation rates and affinities can be determined. BLI can for example be performed using the well-known Octet® Systems (ForteBio, a division of Pall Life Sciences, Menlo Park, USA).

Alternatively, affinities can be measured in Kinetic Exclusion Assay (KinExA) (see for example Drake et al. 2004, Anal. Biochem., 328: 35-43), using the KinExA® platform (Sapidyne Instruments Inc, Boise, USA). The term "KinExA", as used herein, refers to a solution-based method to measure true equilibrium binding affinity and kinetics of unmodified molecules. Equilibrated solutions of an antibody/antigen complex are passed over a column with beads precoated with antigen (or antibody), allowing the free antibody (or antigen) to bind to the coated molecule. Detection of the antibody (or antigen) thus captured is accomplished with a fluorescently labeled protein binding the antibody (or antigen).

The GYROLAB® immunoassay system provides a platform for automated bioanalysis and rapid sample turnaround (Fraley et al. 2013, Bioanalysis 5: 1765-74).

5.3 (In Vivo) Half-Life Extension

The polypeptide may further comprise one or more other groups, residues, moieties or binding units, optionally linked via one or more peptidic linkers, in which said one or more other groups, residues, moieties or binding units provide the polypeptide with increased (in vivo) half-life, compared to the corresponding polypeptide without said one or more other groups, residues, moieties or binding units. In vivo half-life extension means, for example, that the polypeptide has an increased half-life in a mammal, such as a human subject, after administration. Half-life can be expressed for example as t1/2beta.

The type of groups, residues, moieties or binding units is not generally restricted and may for example be chosen from the group consisting of a polyethylene glycol molecule, serum proteins or fragments thereof, binding units that can bind to serum proteins, an Fc portion, and small proteins or peptides that can bind to serum proteins.

More specifically, said one or more other groups, residues, moieties or binding units that provide the polypeptide with increased half-life can be chosen from the group consisting of binding units that can bind to serum albumin, such as human serum albumin, or a serum immunoglobulin, such as IgG. In one embodiment, said one or more other groups, residues, moieties or binding units that provide the polypeptide with increased half-life is a binding unit that can bind to human serum albumin. In one embodiment, the binding unit is an ISVD.

For example, WO 2004/041865 describes ISVDs binding to serum albumin (and in particular against human serum albumin) that can be linked to other proteins (such as one or more other ISVDs binding to a desired target) in order to increase the half-life of said protein.

The international application WO 2006/122787 describes a number of ISVDs against (human) serum albumin. These ISVDs include the ISVDs called Alb-1 (SEQ ID NO: 52 in WO 2006/122787) and humanized variants thereof, such as Alb-8 (SEQ ID NO: 62 in WO 2006/122787). Again, these can be used to extend the half-life of therapeutic proteins and polypeptide and other therapeutic entities or moieties.

Moreover, WO 2012/175400 describes a further improved version of Alb-1, called Alb-23.

In one embodiment, the polypeptide comprises a serum albumin binding moiety selected from Alb-1, Alb-3, Alb-4, Alb-5, Alb-6, Alb-7, Alb-8, Alb-9, Alb-10 (WO 2006/122787) and Alb-23. In one embodiment, the serum albumin binding moiety is Alb-8 or Alb-23 or its variants, as shown on pages 7-9 of WO 2012/175400. In one embodiment, the serum albumin binding moiety is selected from the albumin binders described in WO 2012/175741, WO2015/173325, WO2017/080850, WO2017/085172, WO2018/104444, WO2018/134235, and WO2018/134234. Some serum albumin binders are also shown in Table A-4. In one embodiment, a further component of the polypeptide of the present technology is as described in the following item D:

D. An ISVD that binds to human serum albumin and comprises
   i. a CDR1 that is the amino acid sequence of SEQ ID NO: 8 or an amino acid sequence with 2 or 1 amino acid difference with SEQ ID NO: 8;

ii. a CDR2 that is the amino acid sequence of SEQ ID NO: 12 or an amino acid sequence with 2 or 1 amino acid difference with SEQ ID NO: 12; and iii. a CDR3 that is the amino acid sequence of SEQ ID NO: 16 or an amino acid sequence with 2 or 1 amino acid difference with SEQ ID NO: 16.

In one embodiment, the ISVD comprises a CDR1 that is the amino acid sequence of SEQ ID NO: 8, a CDR2 that is the amino acid sequence of SEQ ID NO: 12 and a CDR3 that is the amino acid sequence of SEQ ID NO: 16.

Examples of such an ISVD that binds to human serum albumin have one or more, or all, framework regions as indicated for construct ALB23002 in Table A-2 (in addition to the CDRs as defined in the preceding item D). In one embodiment, it is an ISVD comprising or consisting of the full amino acid sequence of construct ALB23002 (SEQ ID NO: 4, see Table A-1 and A-2).

Item D can be also described using the Kabat definition as:

D'. An ISVD that binds to human serum albumin and comprises i. a CDR1 that is the amino acid sequence of SEQ ID NO: 124 or an amino acid sequence with 2 or 1 amino acid difference with SEQ ID NO: 124;

ii. a CDR2 that is the amino acid sequence of SEQ ID NO: 132 or an amino acid sequence with 2 or 1 amino acid difference with SEQ ID NO: 132; and iii. a CDR3 that is the amino acid sequence of SEQ ID NO: 140 or an amino acid sequence with 2 or 1 amino acid difference with SEQ ID NO: 140.

In one embodiment, the ISVD comprises a CDR1 that is the amino acid sequence of SEQ ID NO: 124, a CDR2 that is the amino acid sequence of SEQ ID NO: 132 and a CDR3 that is the amino acid sequence of SEQ ID NO: 140.

Examples of such an ISVD that binds to human serum albumin have one or more, or all, framework regions as indicated for construct ALB23002 in Table A-2.1 (in addition to the CDRs as defined in the preceding item D'). In one embodiment, it is an ISVD comprising or consisting of the full amino acid sequence of construct ALB23002 (SEQ ID NO: 4, see Table A-1 and A-2.1).

Also in another embodiment, the amino acid sequence of an ISVD binding to human serum albumin may have a sequence identity of more than 90%, such as more than 95% or more than 99%, with SEQ ID NO: 4, wherein the CDRs are as defined in the preceding item D or D'. In one embodiment, the ISVD binding to human serum albumin comprises or consists of the amino acid sequence of SEQ ID NO: 4.

When such an ISVD binding to human serum albumin has 2 or 1 amino acid difference in at least one CDR relative to a corresponding reference CDR sequence (item D or D' above), the ISVD has at least half the binding affinity, or at least the same binding affinity, to human serum albumin compared to construct ALB23002 (SEQ ID NO: 4), wherein the binding affinity is measured using the same method, such as SPR.

In one embodiment, when such an ISVD binding to human serum albumin has a C-terminal position, it exhibits a C-terminal extension, such as a C-terminal alanine (A) or glycine (G) extension. In one embodiment such an ISVD is selected from SEQ ID NOs: 33, 34, 36, 38, 39, 40, 41, 42, 43, and 45 (see table A-4 below). In another embodiment, the ISVD binding to human serum albumin has another position than the C-terminal position (i.e. is not the C-terminal ISVD of the polypeptide of the technology). In one embodiment such an ISVD is selected from SEQ ID NOs: 4, 31, 32, 35, and 37 (see table A-4 below).

5.4 Nucleic Acid Molecules

Also provided is a nucleic acid molecule encoding the polypeptide of the present technology.

A "nucleic acid molecule" (used interchangeably with "nucleic acid") is a chain of nucleotide monomers linked to each other via a phosphate backbone to form a nucleotide sequence. A nucleic acid may be used to transform/transfect a host cell or host organism, e.g. for expression and/or production of a polypeptide. Suitable hosts or host cells for production purposes will be clear to the skilled person, and may for example be any suitable fungal, prokaryotic or eukaryotic cell or cell line or any suitable fungal, prokaryotic or eukaryotic organism. A host or host cell comprising a nucleic acid encoding the polypeptide of the present technology is also encompassed by the present technology.

A nucleic acid may be for example DNA, RNA, or a hybrid thereof, and may also comprise (e.g. chemically) modified nucleotides, like PNA. It can be single- or double-stranded. In one embodiment, it is in the form of double-stranded DNA. For example, the nucleotide sequences of the present technology may be genomic DNA, cDNA.

The nucleic acids of the present technology can be prepared or obtained in a manner known per se, and/or can be isolated from a suitable natural source. Nucleotide sequences encoding naturally occurring (poly)peptides can for example be subjected to site-directed mutagenesis, so as to provide a nucleic acid molecule encoding polypeptide with sequence variation. Also, as will be clear to the skilled person, to prepare a nucleic acid, also several nucleotide sequences, such as at least one nucleotide sequence encoding a targeting moiety and for example nucleic acids encoding one or more linkers can be linked together in a suitable manner.

Techniques for generating nucleic acids will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers.

5.5 Vectors

Also provided is a vector comprising the nucleic acid molecule encoding the polypeptide of the present technology. A vector as used herein is a vehicle suitable for carrying genetic material into a cell. A vector includes naked nucleic acids, such as plasmids or mRNAs, or nucleic acids embedded into a bigger structure, such as liposomes or viral vectors.

In some embodiments, vectors comprise at least one nucleic acid that is optionally linked to one or more regulatory elements, such as for example one or more suitable promoter(s), enhancer(s), terminator(s), etc.). In one embodiment, the vector is an expression vector, i.e. a vector suitable for expressing an encoded polypeptide or construct under suitable conditions, e.g. when the vector is introduced into a (e.g. human) cell. DNA-based vectors include the presence of elements for transcription (e.g. a promoter and a polyA signal) and translation (e.g. Kozak sequence).

In one embodiment, in the vector, said at least one nucleic acid and said regulatory elements are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promotor). Generally, when two nucleotide sequences are operably linked, they will be in the same orientation and usually also in the same reading frame. They will usually also be essentially contiguous, although this may also not be required.

In one embodiment, any regulatory elements of the vector are such that they are capable of providing their intended biological function in the intended host cell or host organism.

For instance, a promoter, enhancer or terminator should be "operable" in the intended host cell or host organism, by which is meant that for example said promoter should be capable of initiating or otherwise controlling/regulating the transcription and/or the expression of a nucleotide sequence—e.g. a coding sequence—to which it is operably linked.

5.6 Compositions

The present technology also provides a composition comprising at least one polypeptide of the present technology, at least one nucleic acid molecule encoding a polypeptide of the present technology or at least one vector comprising such a nucleic acid molecule. The composition may be a pharmaceutical composition. The composition may further comprise at least one pharmaceutically acceptable carrier, diluent or excipient and/or adjuvant, and optionally comprise one or more further pharmaceutically active polypeptides and/or compounds.

5.7 Host Organisms

The present technology also pertains to host cells or host organisms comprising the polypeptide of the present technology, the nucleic acid encoding the polypeptide of the present technology, and/or the vector comprising the nucleic acid molecule encoding the polypeptide of the present technology.

Suitable host cells or host organisms are clear to the skilled person, and are for example any suitable fungal, prokaryotic or eukaryotic cell or cell line or any suitable fungal, prokaryotic or eukaryotic organism. Specific examples include HEK293 cells, CHO cells, *Escherichia coli* or

*Pichia pastoris*. In one embodiment, the host is *Pichia pastoris*.

5.8 Methods and Uses of the Polypeptide

The present technology also provides a method for producing the polypeptide of the present technology. The method may comprise transforming/transfecting a host cell or host organism with a nucleic acid encoding the polypeptide, expressing the polypeptide in the host, optionally followed by one or more isolation and/or purification steps. Specifically, the method may comprise:

a) expressing, in a suitable host cell or host organism or in another suitable expression system, a nucleic acid sequence encoding the polypeptide; optionally followed by:

b) isolating and/or purifying the polypeptide.

Suitable host cells or host organisms for production purposes will be clear to the skilled person, and may for example be any suitable fungal, prokaryotic or eukaryotic cell or cell line or any suitable fungal, prokaryotic or eukaryotic organism. Specific examples include HEK293 cells, CHO cells, *Escherichia coli* or *Pichia pastoris*. In one embodiment, the host is *Pichia pastoris*.

The polypeptide of the present technology, a nucleic acid molecule or vector as described, or a composition comprising the polypeptide of the present technology, nucleic acid molecule or vector are useful as a medicament.

Accordingly, the present technology provides the polypeptide of the present technology, a nucleic acid molecule or vector as described, or a composition comprising the polypeptide of the present technology, nucleic acid molecule or vector for use as a medicament.

Also provided is the polypeptide of the present technology, a nucleic acid molecule or vector as described, or a composition comprising the polypeptide of the present technology, nucleic acid molecule or vector for use in the (prophylactic and/or therapeutic) treatment.

Also provided is the polypeptide of the present technology, a nucleic acid molecule or vector as described, or a composition comprising the polypeptide of the present technology, nucleic acid molecule or vector for use in the (prophylactic and/or therapeutic) treatment of an autoimmune or an inflammatory disease.

Also provided is the polypeptide of the present technology, a nucleic acid molecule or vector as described, or a composition comprising the polypeptide of the present technology, nucleic acid molecule or vector for use in the (prophylactic and/or therapeutic) treatment of inflammatory bowel disease, such as Crohn's disease and ulcerative colitis, psoriasis, psoriatic arthritis and Hidradenitis suppurativa.

Further provided is a (prophylactic and/or therapeutic) method of treating autoimmune or an inflammatory disease, wherein said method comprises administering, to a subject in need thereof, a pharmaceutically active amount of the polypeptide of the present technology, a nucleic acid molecule or vector as described, or a composition comprising the polypeptide of the present technology, nucleic acid molecule or vector.

Further provided is a (prophylactic and/or therapeutic) method of treating inflammatory bowel disease, such as Crohn's disease and ulcerative colitis, psoriasis, psoriatic arthritis and Hidradenitis suppurativa, wherein said method comprises administering, to a subject in need thereof, a pharmaceutically active amount of the polypeptide of the present technology, a nucleic acid molecule or vector as described, or a composition comprising the polypeptide of the present technology, nucleic acid molecule or vector.

Further provided is the use of the polypeptide of the present technology, a nucleic acid molecule or vector as described, or a composition comprising the polypeptide, nucleic acid molecule or vector in the preparation of a pharmaceutical composition, for treating an autoimmune or an inflammatory disease.

Further provided is the use of the polypeptide of the present technology, a nucleic acid molecule or vector as described, or a composition comprising the polypeptide, nucleic acid molecule or vector in the preparation of a pharmaceutical composition, for treating inflammatory bowel disease, such as Crohn's disease and ulcerative colitis, psoriasis, psoriatic arthritis or Hidradenitis suppurativa.

The inflammatory bowel disease may for example be Crohn's disease or ulcerative colitis.

A "subject" as referred to in the context of the present technology can be any animal. In one embodiment, the subject is a mammal. Among mammals, a distinction can be made between humans and non-human mammals. Non-human animals may be for example companion animals (e.g. dogs, cats), livestock (e.g. bovine, equine, ovine, caprine, or porcine animals), or animals used generally for research purposes and/or for producing antibodies (e.g. mice, rats, rabbits, cats, dogs, goats, sheep, horses, pigs, non-human primates, such as cynomolgus monkeys, or camelids, such as llama or alpaca).

In the context of prophylactic and/or therapeutic purposes, the subject can be any animal, and more specifically any mammal. In one embodiment, the subject is a human subject.

Substances, including polypeptides, nucleic acid molecules and vectors, or compositions may be administered to a subject by any suitable route of administration, for example by enteral (such as oral or rectal) or parenteral (such as epicutaneous, sublingual, buccal, nasal, intra-articular, intradermal, intramuscular, intraperitoneal, intravenous, subcutaneous, transdermal, or transmucosal) administration. In one embodiment, substances are administered by parenteral administration, such as intramuscular, subcutaneous or intradermal, administration. In one embodiment, subcutaneous administration is used.

An effective amount of a polypeptide, a nucleic acid molecule or vector as described, or a composition comprising the polypeptide, nucleic acid molecule or vector can be administered to a subject in order to provide the intended treatment results.

One or more doses can be administered. If more than one dose is administered, the doses can be administered in suitable intervals in order to maximize the effect of the polypeptide, composition, nucleic acid molecule or vector.

TABLE A-1

Amino acid sequences of the different monovalent $V_{HH}$ building blocks identified within the tetravalent polypeptide F027500069 ("ID" refers to the SEQ ID NO as used herein)

| Name | ID | Amino acid sequence |
|---|---|---|
| 6C11 | 2 | DVQLVESGGGVVQPGGSLRLSCTASGFTFSTADMGWFRQAPGKGRE FVARISGIDGTTYYDEPVKGRFTISRDNSKNTVYLQMNSLRPEDTALYY CRSPRYADQWSAYDYWGQGTLVTVSS |
| 119A03/1 | 3 | EVQLVESGGGVVQPGGSLRLSCAASGRIFSLPASGNIFNLLTIAWYRQ APGKQRELVATIESGSRTNYADSVKGRFTISRDNSKKTVYLQMNSLRP EDTALYYCQTSGSGSPNFWGQGTLVTVSS |
| ALB23002 | 4 | EVQLVESGGGVVQPGGSLRLSCAASGFTFRSFGMSWVRQAPGKGPE WVSSISGSGSDTLYADSVKGRFTISRDNSKNTLYLQMNSLRPEDTALYY CTIGGSLSRSSQGTLVTVSS |
| 81A12 | 5 | EVQLVESGGGVVQPGGSLRLSCAASGRTLSSYAMGWFRQAPGKERE FVARISQGGTAIYYADSVKGRFTISRDNSKNTVYLQMNSLRPEDTALYY CAKDPSPYYRGSAYLLSGSYDSWGQGTLVKVSS |

TABLE A-2

Sequences for CDRs according to AbM numbering and frameworks ("ID" refers to the given SEQ ID NO)

| ID | $V_{HH}$ | ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|---|
| 2 | 6C11 | 18 | DVQLVESGGG VVQPGGSLRL SCTAS | 6 | GFTFSTA DMG | 20 | WFRQAPGK GREFVA | 10 | RISGID GTTY | 24 | YDEPVKGRFTISRDNSK NTVYLQMNSLRPEDTAL YYCRS | 14 | PRYADQWS AYDY | 28 | WGQGT LVTVSS |
| 3 | 119A03/1 | 19 | EVQLVESGGG VVQPGGSLRL SCAAS | 7 | GRIFSLP ASGNIF NLLTIA | 21 | WYRQAPG KQRELVA | 11 | TIESGS RTN | 25 | YADSVKGRFTISRDNSK KTVYLQMNSLRPEDTAL YYCQT | 15 | SGSGSPNF | 28 | WGQGT LVTVSS |
| 4 | ALB23002 | 19 | EVQLVESGGG VVQPGGSLRL SCAAS | 8 | GFTFRSF GMS | 22 | WVRQAPG KGPEWVS | 12 | SISGSG SDTL | 26 | YADSVKGRFTISRDNSK NTLYLQMNSLRPEDTAL YYCTI | 16 | GGSLSR | 29 | SSQGTL VTVSS |
| 5 | 81A12 | 19 | EVQLVESGGG VVQPGGSLRL SCAAS | 9 | GRTLSSY AMG | 23 | WFRQAPGK EREFVA | 13 | RISQG GTAIY | 27 | YADSVKGRFTISRDNSK NTVYLQMNSLRPEDTAL YYCAK | 17 | DPSPYYRGS AYLLSGSYDS | 30 | WGQGT LVKVSS |

TABLE A-2.1

Sequences for CDRs according to Kabat numbering and frameworks ("ID" refers to the given SEQ ID NO)

| ID | $V_{HH}$ | ID | FRI | ID | CDR1 | ID | FR2 | ID | CDR2 | ID | FR3 | ID | CDR3 | ID | FR4 |
|---|---|---|---|---|---|---|---|---|---|---|---|---|---|---|---|
| 2 | 6C11 | 118 | DVQLVESGGG<br>VVQPGGSLRL<br>SCTASGFTFS | 122 | TADMG | 126 | WFRQAPG<br>KGREFVA | 130 | RISGID<br>GTTYYD<br>EPVKG | 134 | RFTISRDNSKNTVYLQ<br>MNSLRPEDTALYYCRS | 138 | PRYADQWS<br>AYDY | 142 | WGQGT<br>LVTVSS |
| 3 | 119A03/1 | 119 | EVQLVESGGG<br>VVQPGGSLRL<br>SCAASGRIFS | 123 | LPASGNI<br>FNLLTIA | 127 | WYRQAPG<br>KQRELVA | 131 | TIESGS<br>RTNYAD<br>SVKG | 135 | RFTISRDNSKKTVYLQ<br>MNSLRPEDTALYYCQT | 139 | SGSGSPNF | 143 | WGQGT<br>LVTVSS |
| 4 | ALB23002 | 120 | EVQLVESGGG<br>VVQPGGSLRL<br>SCAASGFTFR | 124 | SFGMS | 128 | WVRQAPG<br>KGPEWVS | 132 | SISGSG<br>SDTLYA<br>DSVKG | 136 | RFTISRDNSKNTLYLQ<br>MNSLRPEDTALYYCTI | 140 | GGSLSR | 144 | SSQGT<br>LVTVSS |
| 5 | 81A12 | 121 | EVQLVESGGG<br>VVQPGGSLRL<br>SCAASGRTLS | 125 | SYAMG | 129 | WFRQAPG<br>KEREFVA | 133 | RISQGG<br>TAIYYA<br>DSVKG | 137 | RFTISRDNSKNTVYLQ<br>MNSLRPEDTALYYCAK | 141 | DPSPYYRG<br>SAYLLSGS<br>YDS | 145 | WGQGT<br>LVKVSS |

TABLE A-3

Amino acid sequences of selected multivalent polypeptide ("ID" refers to the given SEQ ID NO)

| Name | ID | Amino acid sequence |
|---|---|---|
| F027500069 | 1 | DVQLVESGGGVVQPGGSLRLSCTASGFTFSTADMGWFR<br>QAPGKGREFVARISGIDGTTYYDEPVKGRFTISRDNSK<br>NTVYLQMNSLRPEDTALYYCRSPRYADQWSAYDYWGQG<br>TLVTVSSGGGGSGGGSEVQLVESGGGVVQPGGSLRLSC<br>AASGRIFSLPASGNIFNLLTIAWYRQAPGKQRELVATI<br>ESGSRTNYADSVKGRFTISRDNSKKTVYLQMNSLRPED<br>TALYYCQTSGSGSPNFWGQGTLVTVSSGGGGSGGGSEV<br>QLVESGGGVVQPGGSLRLSCAASGFTFRSFGMSWVRQA<br>PGKGPEWVSSISGSGSDTLYADSVKGRFTISRDNSKNT<br>LYLQMNSLRPEDTALYYCTIGGSLSRSSQGTLVTVSSG<br>GGGSGGGSEVQLVESGGGVVQPGGSLRLSCAASGRTLS<br>SYAMGWFRQAPGKEREFVARISQGGTAIYYADSVKGRF<br>TISRDNSKNTVYLQMNSLRPEDTALYYCAKDPSPYYRG<br>SAYLLSGSYDSWGQGTLVKVSSA |

TABLE A-4

Serum albumin binding ISVD sequences ("ID" refers to the SEQ ID NO as used herein)

| Name | ID | Amino acid sequence |
|---|---|---|
| Alb8 | 31 | EVQLVESGGGLVQPGNSLRLSCAASGFTFSSFGMSWVRQAPGKGLEWV<br>SSISGSGSDTLYADSVKGRFTISRDNAKTTLYLQMNSLRPEDTAVYYCTIG<br>GSLSRSSQGTLVTVSS |
| Alb23 | 32 | EVQLLESGGGLVQPGGSLRLSCAASGFTFRSFGMSWVRQAPGKGPEWV<br>SSISGSGSDTLYADSVKGRFTISRDNSKNTLYLQMNSLRPEDTAVYYCTIG<br>GSLSRSSQGTLVTVSS |
| Alb129 | 33 | EVQLVESGGGVVQPGNSLRLSCAASGFTFSSFGMSWVRQAPGKGLEW<br>VSSISGSGSDTLYADSVKGRFTISRDNAKTTLYLQMNSLRPEDTATYYCTIG<br>GSLSRSSQGTLVTVSSA |
| Alb132 | 34 | EVQLVESGGGVVQPGGSLRLSCAASGFTFRSFGMSWVRQAPGKGPEW<br>VSSISGSGSDTLYADSVKGRFTISRDNSKNTLYLQMNSLRPEDTATYYCTIG<br>GSLSRSSQGTLVTVSSA |
| Alb11 | 35 | EVQLVESGGGLVQPGNSLRLSCAASGFTFSSFGMSWVRQAPGKGLEWV<br>SSISGSGSDTLYADSVKGRFTISRDNAKTTLYLQMNSLRPEDTAVYYCTIG<br>GSLSRSSQGTLVTVSS |
| Alb11<br>(S112K)-A | 36 | EVQLVESGGGLVQPGNSLRLSCAASGFTFSSFGMSWVRQAPGKGLEWV<br>SSISGSGSDTLYADSVKGRFTISRDNAKTTLYLQMNSLRPEDTAVYYCTIG<br>GSLSRSSQGTLVKVSSA |
| Alb82 | 37 | EVQLVESGGGVVQPGNSLRLSCAASGFTFSSFGMSWVRQAPGKGLEW<br>VSSISGSGSDTLYADSVKGRFTISRDNAKTTLYLQMNSLRPEDTALYYCTIG<br>GSLSRSSQGTLVTVSS |
| Alb82-A | 38 | EVQLVESGGGVVQPGNSLRLSCAASGFTFSSFGMSWVRQAPGKGLEW<br>VSSISGSGSDTLYADSVKGRFTISRDNAKTTLYLQMNSLRPEDTALYYCTIG<br>GSLSRSSQGTLVTVSSA |

TABLE A-4-continued

| Serum albumin binding ISVD sequences ("ID" refers to the SEQ ID NO as used herein) | | |
|---|---|---|
| Name | ID | Amino acid sequence |
| Alb82-AA | 39 | EVQLVESGGGVVQPGNSLRLSCAASGFTFSSFGMSWVRQAPGKGLEW VSSISGSGSDTLYADSVKGRFTISRDNAKTTLYLQMNSLRPEDTALYYCTIG GSLSRSSQGTLVTVSSAA |
| Alb82-AAA | 40 | EVQLVESGGGVVQPGNSLRLSCAASGFTFSSFGMSWVRQAPGKGLEW VSSISGSGSDTLYADSVKGRFTISRDNAKTTLYLQMNSLRPEDTALYYCTIG GSLSRSSQGTLVTVSSAAA |
| Alb82-G | 41 | EVQLVESGGGVVQPGNSLRLSCAASGFTFSSFGMSWVRQAPGKGLEW VSSISGSGSDTLYADSVKGRFTISRDNAKTTLYLQMNSLRPEDTALYYCTIG GSLSRSSQGTLVTVSSG |
| Alb82-GG | 42 | EVQLVESGGGVVQPGNSLRLSCAASGFTFSSFGMSWVRQAPGKGLEW VSSISGSGSDTLYADSVKGRFTISRDNAKTTLYLQMNSLRPEDTALYYCTIG GSLSRSSQGTLVTVSSGG |
| Alb82-GGG | 43 | EVQLVESGGGVVQPGNSLRLSCAASGFTFSSFGMSWVRQAPGKGLEW VSSISGSGSDTLYADSVKGRFTISRDNAKTTLYLQMNSLRPEDTALYYCTIG GSLSRSSQGTLVTVSSGGG |
| Alb23002 | 4 | EVQLVESGGGVVQPGGSLRLSCAASGFTFRSFGMSWVRQAPGKGPEW VSSISGSGSDTLYADSVKGRFTISRDNSKNTLYLQMNSLRPEDTALYYCTIG GSLSRSSQGTLVTVSS |
| Alb223 | 45 | EVQLVESGGGVVQPGGSLRLSCAASGFTFRSFGMSWVRQAPGKGPEW VSSISGSGSDTLYADSVKGRFTISRDNSKNTLYLQMNSLRPEDTALYYCTIG GSLSRSSQGTLVTVSSA |

TABLE A-5

| Linker sequences ("ID" refers to the SEQ ID NO as used herein) | | |
|---|---|---|
| Name | ID | Amino acid sequence |
| 3A linker | 46 | AAA |
| 5GS linker | 47 | GGGGS |
| 7GS linker | 48 | SGGSGGS |
| 8GS linker | 49 | GGGGSGGS |
| 9GS linker | 50 | GGGGSGGGS |
| 10GS linker | 51 | GGGGSGGGGS |
| 15GS linker | 52 | GGGGSGGGGSGGGGS |
| 18GS linker | 53 | GGGGSGGGGSGGGGSGGS |
| 20GS linker | 54 | GGGGSGGGGSGGGGSGGGGS |
| 25GS linker | 55 | GGGGSGGGGSGGGGSGGGGSGGGGS |
| 30GS linker | 56 | GGGGSGGGGSGGGGSGGGGSGGGGS GGGGS |
| 35GS linker | 57 | GGGGSGGGGSGGGGSGGGGSGGGGS GGGGSGGGGS |
| 40GS linker | 58 | GGGGSGGGGSGGGGSGGGGSGGGGS GGGGSGGGGSGGGGS |
| G1 hinge | 59 | EPKSCDKTHTCPPCP |
| 9GS-G1 hinge | 60 | GGGGSGGGSEPKSCDKTHTCPPCP |

TABLE A-5-continued

| Linker sequences ("ID" refers to the SEQ ID NO as used herein) | | |
|---|---|---|
| Name | ID | Amino acid sequence |
| Llama upper long hinge region | 61 | EPKTPKPQPAAA |
| G3 hinge | 62 | ELKTPLGDTTHTCPRCPEPKSCDTP PPCPRCPEPKSCDTPPPCPRCPEPK SCDTPPPCPRCP |

EXAMPLES

6.1 Example 1: Multispecific ISVD Construct Generation

Identification of ISVD-containing polypeptide F027500069 (SEQ ID NO: 1) binding to TNFα and IL-23 resulted from a data-driven multispecific engineering and formatting campaign in which building blocks based on anti-TNFα $V_{HH}$ building blocks (TNF06C11 (WO 2017/081320), TNF01CO2 (WO 2015/173325, SEQ ID NO: 327) and $V_{HH}$#3E (WO 2004/041862, SEQ ID NO: 4)), anti-IL-23p19 $V_{HH}$ building blocks (231L37D05, 231L119A03 and 23IL81A12 (WO 2009/068627)) and anti-HSA $V_{HH}$ building block ALB23002 (WO2017085172, SEQ ID NO: 10) were included. Different positions/orientations of the building blocks and different linker lengths (9GS vs 35GS) were applied and proved to be critical for different parameters (potency, cross-reactivity, expression, etc.). Potency in this context refers to the inhibition of TNFα-induced NFκB activation in vitro as assayed in Example 6 and inhibition of IL-23-induced mIL-22 production ex vivo as well as inhibition of IL-23 induced SIE promotor activation in vitro as assayed in Examples 7 and 8.

A panel comprising 38 constructs (Table 1) was transformed in *Pichia pastoris* for small scale productions. Induction of ISVD construct expression occurred by stepwise addition of methanol. Clarified medium with secreted ISVD construct was used as starting material for purification via Protein A affinity chromatography followed by desalting. The purified samples were used for functional characterisation and expression evaluation.

Some constructs showed impaired potencies depending on linker length and relative position of ISVD building blocks. For example: potency of bivalent $V_{HH}$#3E towards cyno TNFα was strongly impaired when linked with a short 9GS linker. Another example is that the position of the anti-IL-23 ISVD building block, 37D05, in the multispecific construct was critical to obtain maximal potency.

TABLE 1

Listing of the 38 different multispecific ISVD formats evaluated. BB = building block, ALB = ALB23002.

| Construct ID | BB1 | linker 1 | BB2 | linker 2 | BB3 | linker 3 | BB4 | linker 4 | BB5 |
|---|---|---|---|---|---|---|---|---|---|
| F027500001 | 37D05 | 35GS | ALB | 35GS | 6C11 | | | | |
| F027500002 | 6C11 | 35GS | ALB | 35GS | 37D05 | | | | |
| F027500003 | 37D05 | 35GS | 6C11 | 35GS | ALB | | | | |
| F027500004 | 6C11 | 35GS | 37D05 | 35GS | ALB | | | | |
| F027500005 | 6C11 | 35GS | 119A03/1 | 9GS | ALB | 9GS | 81A12 | | |
| F027500006 | 119A03/1 | 9GS | ALB | 9GS | 81A12 | 35GS | 6C11 | | |
| F027500007 | 37D05 | 35GS | 1C02 | 9GS | ALB | 9GS | 1C02 | | |
| F027500008 | 1C02 | 9GS | ALB | 9GS | 1C02 | 35GS | 37D05 | | |
| F027500009 | 37D05 | 35GS | VHH#3E | 9GS | ALB | 9GS | VHH#3E | | |
| F027500010 | VHH#3E | 9GS | ALB | 9GS | VHH#3E | 35GS | 37D05 | | |
| F027500011 | 119A03/1 | 9GS | ALB | 9GS | 81A12 | 35GS | 1C02 | 30GS | 1C02 |
| F027500012 | 1C02 | 30GS | 1C02 | 35GS | 119A03/1 | 9GS | ALB | 9GS | 81A12 |
| F027500013 | 119A03/1 | 9GS | ALB | 9GS | 81A12 | 35GS | VHH#3E | 9GS | VHH#3E |
| F027500014 | VHH#3E | 9GS | VHH#3E | 35GS | 119A03/1 | 9GS | ALB | 9GS | 81A12 |
| F027500063 | 6C11 | 35GS | 119A03/1 | 9GS | ALB | 9GS | 81A12 | | |
| F027500064 | 119A03/1 | 9GS | ALB | 9GS | 81A12 | 35GS | 6C11 | | |
| F027500069 | 6C11 | 9GS | 119A03/1 | 9GS | ALB | 9GS | 81A12 | | |
| F027500070 | 119A03/1 | 9GS | ALB | 9GS | 81A12 | 9GS | 6C11 | | |
| F027500073 | 119A03/1 | 9GS | ALB | 9GS | 81A12 | 35GS | 1C02 | 35GS | 1C02 |
| F027500074 | 1C02 | 35GS | 1C02 | 35GS | 119A03/1 | 9GS | ALB | 9GS | 81A12 |
| F027500075 | 119A03/1 | 9GS | ALB | 9GS | 81A12 | 35GS | VHH#3E | 9GS | VHH#3E |
| F027500076 | VHH#3E | 9GS | VHH#3E | 35GS | 119A03/1 | 9GS | ALB | 9GS | 81A12 |
| F027500077 | 119A03/1 | 9GS | ALB | 9GS | 81A12 | 9GS | 1C02 | 35GS | 1C02 |
| F027500078 | 1C02 | 35GS | 1C02 | 9GS | 119A03/1 | 9GS | ALB | 9GS | 81A12 |
| F027500079 | 119A03/1 | 9GS | ALB | 9GS | 81A12 | 9GS | VHH#3E | 9GS | VHH#3E |
| F027500080 | VHH#3E | 9GS | VHH#3E | 9GS | 119A03/1 | 9GS | ALB | 9GS | 81A12 |
| F027500082 | 119A03/1 | 35GS | 81A12 | 9GS | 1C02 | 9GS | ALB | 9GS | 1C02 |
| F027500083 | VHH#3E | 9GS | ALB | 9GS | VHH#3E | 9GS | 119A03/1 | 35GS | 81A12 |
| F027500084 | 119A03/1 | 35GS | 81A12 | 9GS | VHH#3E | 9GS | ALB | 9GS | VHH#3E |
| F027500085 | 1C02 | 9GS | ALB | 9GS | 1C02 | 35GS | 119A03/1 | 35GS | 81A12 |
| F027500086 | 119A03/1 | 35GS | 81A12 | 35GS | 1C02 | 9GS | ALB | 9GS | 1C02 |
| F027500087 | VHH#3E | 9GS | ALB | 9GS | VHH#3E | 35GS | 119A03/1 | 35GS | 81A12 |
| F027500088 | 119A03/1 | 35GS | 81A12 | 35GS | VHH#3E | 9GS | ALB | 9GS | VHH#3E |
| F027500093 | 37D05 | 9GS | ALB | 9GS | 6C11 | | | | |
| F027500094 | 37D05 | 9GS | 6C11 | 9GS | ALB | | | | |
| F027500095 | 37D05 | 9GS | 1C02 | 9GS | ALB | 9GS | 1C02 | | |
| F027500096 | 37D05 | 9GS | VHH#3E | 9GS | ALB | 9GS | VHH#3E | | |

Subsequently, the large panel was trimmed down to a panel of 4 multispecific constructs, consisting of ISVD constructs F027500069, F027500093, F027500095 and F027500096, proven to be potent on both targets (human and cyno) and comprising the potential of high expression levels, based on preliminary yield estimates.

Larger scale 2 L productions in *Pichia pastoris* were done for expression yield determination and assessment of biophysical properties and pre-existing antibody reactivity. Table 2 shows that a specific orientation of the buildings blocks was required to obtain high expression levels in *Pichia pastoris*. The expression yields, obtained from 5 ml cultures, for 4 formatted ISVD constructs with the same building blocks, but in different orientations and with different linker lengths, clearly indicate that ISVD 6C11 needs an N-terminal position for good expression. This was confirmed upon 2 L fermentation of F027500069 and F027500070, where the ISVD construct with N-terminal 6C11 (F027500069) reached a titer of 6.4 g/L which was 3.2-fold higher than for F027500070, with C-terminal 6C11.

TABLE 2

Expression levels of 4 ISVD constructs with the building block 6C11, 119A03/1 and 81A12 in different orientations and with different linker lengths.

| Construct ID | BB1 | linker 1 | BB2 | linker 2 | BB3 | linker 3 | BB4 | Yield from 5 ml culture (μg/ml) | Yield from 2 L fermentation (g/L) |
|---|---|---|---|---|---|---|---|---|---|
| F027500063 | 6C11 | 35GS | 119A03/1 | 9GS | ALB | 9GS | 81A12 | 129.0 | |
| F027500064 | 119A03/1 | 9GS | ALB | 9GS | 81A12 | 35GS | 6C11 | 81.7 | |
| F027500069 | 6C11 | 9GS | 119A03/1 | 9GS | ALB | 9GS | 81A12 | 165.2 | 6.4 |
| F027500070 | 119A03/1 | 9GS | ALB | 9GS | 81A12 | 9GS | 6C11 | 104.6 | 2.0 |

Table 3 and example 9 show that the pre-existing antibody reactivity is driven by the composition and the valency of the respective ISVD constructs.

TABLE 3

Binding of pre-existing antibodies present in 96 human serum samples to F027500069, F027500093, F027500095 and F027500096 compared to control ISVD constructs F027301099 and F027301186

| Construct ID | BB1 | linker l | BB2 | linker 2 | BB3 | linker 3 | BB4 | linker 4 | BB5 | 25% percentile | Median RU level | 75% percentile |
|---|---|---|---|---|---|---|---|---|---|---|---|---|
| F027301099 | 1B11 | 35GS | ALB | 35GS | 1B11 | 35GS | 6C11 | | | 47 | 92 | 350 |
| F027301186 | 1E07 | 35GS | 1E07 | 35GS | 1C02 | 9GS | ALB | 9GS | 1C02 | 61 | 135 | 622 |
| F027500069 | 6C11 | 9GS | 119A03/1 | 9GS | ALB | 9GS | 81A12-A | | | −15 | −8 | 5 |
| F027500093 | 37D05 | 9GS | ALB | 9GS | 6C11-A | | | | | −12 | −5 | 22 |
| F027500095 | 37D05 | 9GS | 1C02 | 9GS | ALB | 9GS | 1C02-A | | | 0 | 7 | 22 |
| F027500096 | 37D05 | 9GS | VHH#3E | 9GS | ALB | 9GS | VHH#3E-A | | | 5 | 14 | 22 |

Finally, ISVD construct F027500069 was selected based on potency, reduced binding to pre-existing antibodies, superior expression levels and CMC characteristics, with low viscosity of 3.3 cP at a concentration of 100 mg/mL, and 6.4 cP at 146 mg/mL in a defined buffer.

6.2 Example 2: Multispecific ISVD Construct Binding Affinity to TNFα, IL-23 and Serum Albumin The affinity, expressed as the equilibrium dissociation constant ($K_D$), of F027500069 towards human and cyno TNFα, human and cyno IL-23 and human and cyno serum albumin was quantified by means of in-solution affinity measurements on a Gyrolab xP Workstation (Gyros).

Under $K_D$-controlled measurements, a serial dilution of TNFα or IL-23 (ranging from 1 μM-0.1 pM) or serum albumin (ranging from 10 μM-1 pM) and a fixed amount of F027500069 (50 pM in case of TNFα, 20 pM or 12.5 pM in case of IL-23 and 1 nM in case of serum albumin) were mixed to allow interaction and incubated for either 24 or 48 hours (in case of IL-23 and TNFα) or 2 hours (in case of serum albumin) to reach equilibrium.

Under receptor-controlled measurements a serial dilution of TNFα or IL-23 (ranging from 1 μM-0.1 pM) or serum albumin (ranging from 10 μM-1 pM) and a fixed amount of F027500069 (5 nM in case of TNFα, 1.25 nM in case of IL-23 and 50 nM in case of serum albumin) were mixed to allow interaction and incubated for either 24 or 48 hours (in case of IL-23 and TNFα) or 2 hours (in case of serum albumin) to reach equilibrium.

Biotinylated human TNFα/IL-23/serum albumin was captured in the microstructures of a Gyrolab Bioaffy 1000 CD, which contains columns of beads and is used as a molecular probe to capture free F027500069 from the equilibrated solution. The mixture of TNFα/IL-23/serum albumin and F027500069 (containing free TNFα/IL-23/serum albumin, free F027500069 and TNFα/IL-23/serum albumin-F027500069 complexes) was allowed to flow through the beads, and a small percentage of free F027500069 was captured, which is proportional to the free ISVD concentration. A fluorescently labelled anti-$V_{HH}$ antibody was then injected to label any captured F027500069 and after rinsing away excess of fluorescent probe, the change in fluorescence was determined. Fitting of the dilution series was done using Gyrolab Analysis software, where $K_D$- and receptor-controlled curves were analyzed to determine the $K_D$ value.

The results (Table 4) demonstrate that the multispecific ISVD construct binds human/cyno IL-23 and human/cyno TNFα with high affinity.

TABLE 4

Binding affinities of F027500069 to human and cyno IL-23, TNFα and serum albumin

| | human | | cynomolgus monkey | | Incubation |
|---|---|---|---|---|---|
| Antigen | $K_D$ (pM) | 95% Cl (pM) | $K_D$ (pM) | 95% Cl (pM) | time (h) |
| IL-23 | 14.1 | 3.2-26.4 | 33.5 | 4.8-62.0 | 24 |
| | 28.1 | 17.0-39.0 | 51.2 | 22.1-80.1 | 48 |
| TNFα | 3.23 | 2.10-4.35 | 27.5 | 17.9-31.1 | 24 |
| | 3.39 | 1.53-5.26 | 18.6 | 12.9-24.4 | 48 |
| SA | 5900 | 5320-6480 | 10800 | 9010-12500 | 2 |

6.3 Example 3: Multispecific ISVD Construct Binding to Membrane Bound TNFα

Binding of F027500069 to membrane bound TNFα was demonstrated using flow cytometry on human membrane TNFα expressing HEK293H cells and on activated CD4+ cells that were isolated from PBMC's and stimulated with PMA and lonomycin (data shown for TNFα expressing HEK293H cells). Briefly, cells were seeded at a density of $1\times10^4$ cells/well and incubated with a dilution series of F027500069 starting from 100 nM up to 0.5 pM, for 1 hour at 4° C. In parallel, cells were fixed with 4% paraformaldehyde and 0.1% Glutaraldehyde in PBS, before seeding (to increase detection of membrane bound TNFα) and incubated with a dilution series of ISVD for 1 hour at 4° C. or for 24 hours at room temperature. Cells were washed 3 times and subsequently incubated with an anti-$V_{HH}$ mAb for 30 min at 4° C., washed again, and incubated for 30 min at 4° C. with a goat anti-mouse PE labelled antibody. Samples were washed and resuspended in FACS Buffer (D-PBS with 10% FBS and 0.05% sodium azide supplemented with 5 nM TOPRO3). Cell suspensions were then analysed on an iQuescreener. EC50 values were calculated using GraphPad Prism. EC50 values for F027500069 were in the same range for viable and fixed cells after 1-hour incubation, though fixation of the cells resulted in higher expression levels of TNFα on the membrane (Table 5). After 24 hours incubation, binding equilibrium was reached, with a concomitant 6.6-fold improvement of the EC50.

TABLE 5

Binding affinity of F027500069 to membrane expressed TNFα after incubation times of 1 hour or 24 hours

| Analyte | T = 1 h viable cells EC50 (M) | T = 1 h fixed cells EC50 (M) | T = 24 h fixed cells EC50 (M) |
|---|---|---|---|
| F027500069 | 6.93E−10 | 8.11E−10 | 1.22E−10 |

6.4 Example 4: Multispecific ISVD Construct Binds Selectively to TNFα and IL-23

Absence of binding to TNFα and IL-23 related human cytokines was assessed via SPR. hIL-12 was tested, as it shares the p40 subunit with IL-23. TNF superfamily members human FASL, TNFβ, LIGHT, TL-1A, RANKL were tested as related cytokines for TNFα.

Targets were immobilized at 10 μg/mL for 600s using amine coupling with 420 seconds injection of EDC/NHS for activation and a 420-seconds injection of 1 M Ethanolamine HCl for deactivation (Sierra Sensors Amine Coupling Kit II Cat No ACK-001-025). Flow rate during activation, deactivation and ligand injection was set to 10 μl/min. The pH of the 10 mM Acetate immobilization buffer was chosen by subtracting ~1.5 from the pl of each ligand.

Next, 1 μM of F027500069 was injected for 2 minutes and allowed to dissociate for 900s at a flow rate of 45 μL/min. As running buffer 1×HBS-EP+pH7.4 was used. As positive controls, 0.2 μM α-hulL-12 Ab and 0.5 μM α-huFASL Ab, 0.5 μM α-huTNFβAb, 0.5 μM α-huLIGHT Ab, 0.5 μM α-huTL-1A Ab and 0.5 μM α-huRANKL $V_{HH}$ were injected. Interaction between F027500069 and the positive controls with the immobilized targets was measured by detection of increases in refractory index which occurs as a result of mass changes on the chip upon binding.

All positive controls did bind to their respective target. No binding was detected of F027500069 to human IL-12, FASL, TNFβ, LIGHT, TL-1A, RANKL.

6.5 Example 5: Simultaneous Binding of Multispecific ISVD Construct to hIL-23 and hTNFα

A ProteOn XPR36 instalment was used to determine whether F027500069 can bind simultaneously to hTNFα and hIL-23. To this end HSA was immobilized on a GLC ProteOn Sensor chip via amine coupling. 100 nM of F027500069 was injected for 2 min at 10 μl/min over the HSA surface in order to capture the ISVD via the ALB23002 building block. Subsequently either 100 nM of hIL-23, hTNFα or hOX40L were injected or mixtures of 100 nM IL-23+100 nM TNFα, 100 nM IL-23+100 nM OX40L or 100 nM TNFα+100 nM IL-13, at a flow rate of 10 μl/min for 2 min followed by a subsequent 600 seconds dissociation step. The HSA surfaces were regenerated with a 2-minute injection of HCl (100 mM) at 45 μl/min. The sensorgram (FIG. 1) demonstrates that F027500069 can bind human IL-23 and human TNFα simultaneously as shown by the increase in response units: ~500 RU increase from TNFα only, ~880 RU increase from IL-23 only and ~1300 RU increase for the IL-23 and TNFα mixture.

6.6 Example 6: Multispecific ISVD Construct Inhibition of TNFα-Induced NFkB Activation In Vitro HEK293_NFkB-NLucP cells are TNF receptor expressing cells that were stably transfected with a reporter construct encoding Nano luciferase under control of a NFkB dependent promoter. Incubation of the cells with soluble human and cyno TNFα resulted in NFκB mediated Nano luciferase gene expression. Nano luciferase luminescence was measured using Nano-Glo Luciferase substrate mixed with lysing buffer at the ratio of 1:50 added onto cells. Samples were mixed 5 min on a shaker to obtain complete lysis.

Glo Response™ HEK293_NFkB-NLucP cells were seeded at 20000 cells/well in normal growth medium in white tissue culture (TC) treated 96-well plates with transparent bottom. Dilution series of F027500069 or reference compound (anti-TNFα reference mAb) were added to 25 pM human or 70 pM cyno TNFα and incubated with the cells for 5 hours at 37° C. in the presence of 30 μM HSA.

F027500069 inhibited human and cyno TNFα-induced NFκB activation in a concentration-dependent manner with an IC50 of 38.8 pM (for human TNFα) and 128 pM (for cyno TNFα) comparable to the anti-TNFα reference mAb (Table 6, FIG. 2).

TABLE 6

IC50 values of F027500069 mediated neutralization of human and cyno TNFα in the Glo response ™ HEK293_NFκB-NLucP reporter assay versus the reference compound anti-hTNFα reference mAb

| | F02750069 | | anti-hTNFα referencem Ab | |
|---|---|---|---|---|
| antigen | Human TNFα | Cyno TNFα | Human TNFα | Cyno TNFα |
| NFkB assay IC50 (M) | 3.88E−11 | 1.28E−10 | 5.74E−11 | 7.00E−11 |

6.7 Example 7: Multispecific ISVD Construct Inhibition of IL-23-Induced mIL-22 Production Ex Vivo Human (and cyno) IL-23 stimulated mIL-17 and mIL-22 secretion from mouse spleen cells (Aggarwal et al. 2003, J. Biol. Chem. 278(3): 1910-4). It was demonstrated that F027500069 blocks the 1L-23-induced expression of mIL-22 ex vivo. Spleens of 5 C57BL/6 mice were removed, splenocytes harvested and a single cell suspension was prepared. Cells were cultured in the presence of 20 ng/ml recombinant mIL-2 and seeded at 400 000 cells/well in 96-well flat bottom plates. Serial dilutions of F027500069 or reference compounds (anti-hIL-23 reference mAb1 and anti-hIL-23 reference mAb2) were pre-incubated with recombinant hIL-23 (36 pM) or recombinant IL-23 from cynomolgus monkey (36 pM) in culture medium for 30 minutes at room temperature and then incubated for another 3 days with the splenocytes in the presence of 30 μM HSA at 37° C. Supernatants were collected and levels of mIL-22 were measured using ELISA.

The results shown in Table 7 demonstrate that F027500069 inhibited hIL-23- and cyno IL-23-induced mIL-22 production in a concentration-dependent manner with and IC50 of 43 pM (for human IL-23) and 31 pM (for cyno IL-23). The inhibition was more potent than the inhibition by the reference compounds anti-hIL-23 reference mAb1 and anti-hIL-23 reference mAb2.

6.8 Example 8: Multispecific ISVD Construct Inhibition of IL-23 Induced SIE Promotor Activation In Vitro Glo Response™ HEK293_human IL-23R/IL-12Rb1-Luc2P cells were stably transfected with a reporter construct containing the luciferase gene under control of the SIE responsive promotor. Additionally, these cells constitutively overexpressed both subunits of the human IL-23 receptor, i.e. IL-12Rb1 and IL-23R. Upon triggering of these cells by IL-23, the luciferase reporter protein was expressed, which is quantified based on its enzymatic activity by addition of the substrate, 5'-fluoroluciferin (Bio-Glo™ Luciferase Assay System).

Cells were cultured in normal growth medium and seeded at 15000 cells/well in 96-well white tissue culture treated plates with transparent bottom. Serial dilutions of F027500069 or reference compounds (anti-hIL-23 reference mAb1 and anti-hIL-23 reference mAb2) were added to the cells, followed by the addition of recombinant hIL-23 (10 pM) or cyno IL-23 (40 pM). Cells were incubated for 4 hours 15 min at 37° C. in the presence of 30 μM HSA. Subsequently Bio-Glo was added in each well onto cells and luciferase luminescence was measured. F027500069 inhibited the human and cyno IL-23-dependent signalling with an IC50 of 250 pM and 323 pM respectively (Table 7 and FIG. 3).

TABLE 7

IC50 values of F027500069 mediated neutralization of human and cyno IL-23 in the mouse splenocyte assay and the Glo response ™ HEK293_human IL-23R/IL-12Rb1-Luc2P reporter assay, versus the reference compounds anti-hIL-23 reference mAb1 and anti-hIL-23 reference mAb2.

| | F02750069 | | anti-hIL-23reference mAb1 | | anti-hIL-23reference mAb2 | |
|---|---|---|---|---|---|---|
| antigen | Human IL-23 | Cyno IL-23 | Human IL-23 | Cyno IL-23 | Human IL-23 | Cyno IL-23 |
| Mouse splenocyte assay IC50 (M) | 4.34E−11 | 3.07E−11 | 1.55E−10 | 7.95E−10 | 6.80E−10 | 4.95E−09 |
| IL-23 reporter assay IC50 (M) | 2.50E−10 | 3.23E−10 | 3.23E−10 | 5.73E−10 | 5.41E−10 | 7.21E−10 |

6.9 Example 9: Multispecific ISVD Construct Binding to Pre-Existing Antibodies The pre-existing antibody reactivity of ISVD construct F027500069 was assessed in normal human serum (n=96) using the ProteOn XPR36 (Bio-Rad Laboratories, Inc.). PBS/Tween (phosphate buffered saline, pH 7.4, 0.005% Tween20) was used as running buffer and the experiments were performed at 25° C.

ISVDs were captured on the chip via binding of the ALB23002 building block to HSA, which was immobilized on the chip. To immobilize HSA, the ligand lanes of a ProteOn GLC Sensor Chip were activated with EDC/NHS (flow rate 30 μl/min) and HSA was injected at 100 μl/ml in ProteOn Acetate buffer pH 4.5 to render immobilization levels of approximately 3200 RU. After immobilization, surfaces were deactivated with ethanolamine HCl (flow rate 30 μl/min).

Subsequently, ISVD constructs were injected for 2 min at 45 μl/min over the HSA surface to render a ISVD capture level of approximately 800 RU. The samples containing pre-existing antibodies were centrifuged for 2 minutes at 14,000 rpm and supernatant was diluted 1:10 in PBS-Tween20 (0.005%) before being injected for 2 minutes at 45 μl/min followed by a subsequent 400 seconds dissociation step. After each cycle (i.e. before a new ISVD capture and blood sample injection step) the HSA surfaces were regenerated with a 2-minute injection of HCl (100 mM) at 45 μl/min. Sensorgrams showing pre-existing antibody binding were obtained after double referencing by subtracting 1) ISVD-HSA dissociation and 2) non-specific binding to reference ligand lane. Binding levels of pre-existing antibodies were determined by setting report points at 125 seconds (5 seconds after end of association). Percentage reduction in pre-existing antibody binding was calculated relative to the binding levels at 125 seconds of a reference ISVD.

The tetravalent ISVD construct F027500069, optimized for reduced pre-existing antibody binding by introduction of mutations L11V and V89L in each building block and a C-terminal alanine, showed substantially less binding to pre-existing antibodies compared to a control non-optimized tetravalent ISVD construct F027301099, (Table 8 and FIG. 4).

TABLE 8

Binding of pre-existing antibodies present in 96 human serum samples to F027500069 compared to control ISVD construct F027301099

| ID | Short description | 25% per-centile | Median RU level | 75% per-centile |
|---|---|---|---|---|
| F027301099 | 1B11-35GS-ALB23000-35GS-1B11-35GS-6C11 | 47 | 92 | 350 |
| F027500069 | 6C11-9GS-119A03/1-9GS-ALB23002-9GS-81A12-A | −15 | −8 | 5 |

Pre-existing antibody binding depended on the valency and composition of the multispecific constructs. Table 3 and FIG. 5 demonstrate that construct F027500069 showed lower pre-existing antibody reactivity than constructs F027500095 and F027500096.

6.10 Example 10: Evaluation of F027500069 in the Human TNFα Transgenic Tg197 Polyarthritis Model F027500069 was profiled in the Tg197 mouse model of TNF-driven progressive polyarthritis (Keffer at al., 1991, EMBO J., 10:4025-4031). In these mice, a modified human TNFα gene was inserted as a transgene into mice. The human gene was modified in a way to render the transcribed mRNA more stable, and thus led to overexpression of TNFα and a spontaneous progressive arthritis in all four paws at 100% penetrance. Signs and symptoms become visible at about 6 weeks of age and are constantly increasing until they lead to significant moribundity and mortality from about 10 weeks of age onwards if left untreated. Arthritis severity was clinically assessed by a scoring system as detailed below:

| ARTHRITIS SCORE[1] | CHARACTERISTICS |
|---|---|
| 0/no disease | no arthritis (normal appearance, mouse can support its weight clinging to an inverted or tilted surface such as a wire grid or a cage lid for a period of time, whole body flexibility/evasiveness normal, grip strength maximum) |
| 0.5/mild disease | onset of arthritis (mild joint swelling, all other parameters as above) |
| 1/mild to moderate disease | mild to moderate (joint distortion by swelling, inflamed paw, all other parameters as above) |
| 1.5/moderate disease | moderate arthritis (joint-paw swelling, distortion + last finger inward deformation, brief support clinging to an inverted or tilted surface such as a wire grid or a cage lid, whole body flexibility reduced, reduced grip strength) |

-continued

| ARTHRITIS SCORE[1] | CHARACTERISTICS |
|---|---|
| 2/moderate to severe disease | moderate to severe arthritis (severe joint, paw and finger swelling, joint-leg deformation, no support clinging to an inverted or tilted surface such as a wire grid or a cage lid, no whole-body flexibility, no grip strength, climbing/feeding affected, starts shaking when trying to move, but manages to move forward) |
| 2.5/severe disease | severe arthritis (as above 2 + finger deformation in front paws, mouse movement impaired, shaking not willing to move) |
| 3/very severe disease | very severe arthritis (ankylosis detected on flexion and severely impaired movement, mouse moribund, not shaking anymore, cannot turn/flip around readily when tilted to the side). |

[1]Arthritis score as indicated on the y-axis in FIG. 6.

Arthritis was sensitive to treatment with therapeutic agents directed towards inhibition of human TNFα (Shealy et al., 2002, Arthritis Res. 4(5): R7).

For the purpose of establishing dose-dependent efficacy, different doses of F027500069 were administered by twice weekly intraperitoneal injection in a therapeutic manner to animals of 6 weeks of age with visible signs and symptoms of arthritis (n=8 animals per group). Human IgG1 purified from human myeloma serum (BioXcell #BE0297) was used as negative control, and anti-hTNFα reference mAb was used as positive control to suppress arthritis. F027500069 was administered at three different dose strengths of 1.3 mg/kg of body weight, 4 mg/kg, and 13.5 mg/kg, respectively. Treatment was continued until 11 weeks of age. Clinical arthritis scores were determined once per week. As shown in FIG. 6, treatment with F027500069 resulted in a dose-dependent suppression of clinical arthritis scores over time.

Animals treated with human IgG1 negative control antibody developed a mean arthritis score of 1.099±0.1071 by week 11. Anti-hTNFα reference mAb fully suppressed arthritis progression, with a mean score of 0.4844±0.0594 by week 11. F027500069 reduced the arthritis progression to week 11 with mean scores of 0.8047±0.0929 (1.3 mg/kg), 0.7969±0.0585 (4 mg/kg), and 0.6016±0.0349 (13.5 mg/kg). Overall suppression of arthritis was analysed by Area Under the Curve (AUC, FIG. 7). All doses of F027500069 significantly suppressed arthritis progression comparable to anti-hTNFα reference mAb in the Tg197 arthritis model.

Upon completion of treatment, hindlimb ankle joints were processed for histology and section were evaluated for structural signs of arthritis with the following scoring system:

CUMULATIVE HISTOPATHOLOGICAL CRITERIA FOR SCORING ARTHRITIC PHENOTYPE IN THE ANKLE JOINTS

| SCORE[1] | DISEASE | CRITERIA |
|---|---|---|
| 0 | Normal | no detectable pathology |
| 1 | Mild | hyperplasia of the synovial membrane and presence of polymorphonuclear infiltrates. Mild tendonitis may be present. |
| 2 | Moderate | pannus and fibrous tissue formation and focal subchondrial bone erosion |
| 3 | Moderate-Severe | cartilage destruction and bone erosion |
| 4 | Severe | extensive cartilage destruction and bone erosion. Bone outline structure is lost |

[1]arthritis score as indicated on the y-axis in FIG. 8.

The results of the histology scoring are depicted in FIG. 8. Structural arthritis and joint destruction were significantly suppressed by F027500069 at higher doses.

In conclusion, the results demonstrate dose dependent suppression of arthritis signs and symptoms as well as inhibition of structural progression by the F027500069 to an extent comparable with anti-TNFα reference mAb.

6.11 Example 11: Evaluation of F027500069 in the Human IL-23 Induced Skin Inflammation Model Intradermal injection of recombinant IL-23 in mice led to an acute skin inflammation with reddening and swelling around the injection site. Histologically, hallmarks of psoriatic skin inflammation were visible such as epidermal thickening by keratinocyte hyperplasia, keratosis, and immune cell infiltration like T cells and macrophages. On a molecular level, transcriptome changes in the model largely overlapped with those observed in human psoriatic lesional skin versus normal skin (Gauld et al., 2018, Journal of Dermatological Science 92:45-53). Thus, the IL-23 skin inflammation model resembles a mechanistic model of psoriasis.

To investigate the inhibition of IL-23 mediated inflammation, F027500069 was tested in the skin inflammation model adapted from Rizzo et al., 2011, J Immunol; 186: 1495-1502. 1 μg of recombinant human IL-23 in a total volume of 20 μl was intradermally injected on day 1, 2, 3, and 4 into the right ear of female C57BL/6 mice. PBS was injected as a control into the ears of one group of mice. Ear skin thickening was measured daily by calipers. F027500069 and control compounds were administered on day 1 and 3 by intraperitoneal injection. On day 5, mice were sacrificed, and a skin punch biopsy was taken. The biopsy was homogenized in PBS supplemented with protease inhibitor cocktail, and downstream effector cytokine IL-22 levels were determined.

For the purpose of establishing dose-dependent efficacy, different doses of the ISVD construct were administered by twice weekly intraperitoneal injection: in a therapeutic manner to animals of 6 weeks of age with visible signs and symptoms of arthritis (n=10 animals per group). Human IgG1 purified from human myeloma serum (BioXcell #BE0297) was used as negative control, and anti-hIL-23 reference mAb1 was used as positive control to suppress skin inflammation. F027500069 was administered at four different dose strengths of 0.13 mg/kg of body weight, 0.4 mg/kg, 1 mg/kg, and 4 mg/kg, respectively. As shown in FIG. 9, treatment with F027500069 resulted in a dose-dependent suppression of skin swelling, depicted as change in ear thickness from baseline at day 5.

Skin biopsies were taken at day 5 and tissue homogenates were prepared. Murine IL-22 levels were measured utilizing Mesoscale Discovery V-plex mouse IL-22 assay kit (#K152WVD, FIG. 10). Administration of IL-23 led to measurable levels of IL-22, as all samples from the PBS-injected skin were below the lower limit of quantitation (LLOQ) of the assay employed. All doses of F027500069 as well as anti-hIL-23 reference mAb1 significantly suppressed IL-22 tissue level (for the 1 mg/kg dose group, no IL-22 levels were determined).

In addition, the feasibility for subcutaneous administration was assessed in another experiment in the IL-23 induced skin inflammation model. Two doses of F027500069 (0.1 mg/kg and 1 mg/kg) were administered on day 1 and day 3 either as intraperitoneal or subcutaneous injection, and ear thickness change was obtained (FIG. 11). In this experiment, a 1 mg/kg dose of an unrelated $V_{HH}$ was used as negative control (Nab ctrl), and a 3 mg/kg dose of anti-hIL-23 reference mAb1 (IP) was used as positive control.

In addition, tissue IL-22 level was measured from day 5 skin biopsy homogenates (FIG. 12).

In conclusion, the results demonstrate suppression of IL-23 induced skin inflammation both on skin thickening as well as on tissue effector cytokine level. Both intraperitoneal as well as subcutaneous routes of administration are feasible.

6.12 Example 12: Evaluation of F027500069 in the Collagen Antibody-Induced Arthritis Model in Human TNFα/TNFR1 Knock in Mice F027500069 was profiled in the Collagen Antibody-Induced Arthritis (CAIA) model in proprietary mice where the gene loci of both TNFα as well as TNF receptor 1 (TNFR1) were replaced by the respective human gene loci.

8 animals per group were injected at day 0 with 8 mg of a cocktail of monoclonal antibodies directed against collagen 2 of cartilage (ArthritoMab, MDbioscience, CIA-MAB-2C). On day 1, development of arthritis was triggered by injection of 25 μg bacterial lipopolysaccharide (LPS). Test compounds were administered as a single injection once at 6 hours after LPS injection. Development of sign and symptoms of arthritis was assessed daily until day 7, based on an arthritis score as detailed below:

| ARTHRITIS SCORE[1] | CHARACTERISTICS |
|---|---|
| 0 | No clinical signs or symptoms |
| 1 | Mild swelling of ankle joint and carpus. |
| 2 | Moderate swelling of ankle joint and carpus; involvement of digits. Mild erythema |
| 3 | Severe swelling of whole paw including digits. Severe erythema. |

Each limb is scored separately from 0 to 3, the total arthritis score is the sum of scores of all 4 limbs with a maximum sum score of 12.

[1]arthritis score as indicated on the y-axis in FIG. 13.

F027500069 was administered at 1.3 mg/kg of body weight, anti hTNFα reference mAb positive ctrl was administered at 0.5 mg/kg. FIG. 13 shows the development of arthritis signs and symptoms over time. Single preventative administration of both F027500069 or anti hTNFα reference mAb resulted in complete suppression of arthritis development.

6.13 Example 13: Evaluation of F027500069 in the Human IL-23 Induced Skin Inflammation Model in Human TNFα Knock-In Mice Since F027500069 only binds and inhibits human or primate targets (both IL-23 as well as TNFα), the human IL-23 induced skin inflammation was repeated in TNFα-humanized mice. In this proprietary strain, the whole genomic TNFα locus in mice was replaced by the human gene locus. Exon-intron structure and regulatory elements are conserved between mouse and human. Faithful expression as well as functional competence of human TNFα to elicit responses in the mice has been assessed beforehand.

Intradermal injection of hIL-23 led to a modest increase in TNFα expression (own data and Gauld et al. 2018, Journal of Dermatological Science 92:45-53). Equimolar doses of F027500069 and the corresponding monospecific ISVD building blocks F027500101 (anti-TNFα) and F027500017 (anti-IL-23) were administered in this model to address potential additive effects of dual targeting. The administered dose strength was 3.6 nmol/kg, corresponding to about 0.1 mg/kg. This low dose was chosen to allow for some remaining free IL-23 and thus downstream TNFα secretion. In addition, high doses of F027500069 as well as anti-hIL-23 reference mAb1 were administered as positive controls. The change in ear thickness was normalized to high (Nab negative control) and low (no IL-23 injection) controls (sample minus low ctrl divided by high ctrl minus low ctrl). FIG. 14 illustrates the results. Monospecific TNFα inhibition with 3.6 nmol/kg F027500101 did not inhibit skin swelling, while monospecific IL-23 inhibition with 3.6 nmol/kg F027500017 had a moderate but significant effect. Dual targeting of both TNFα and IL-23 with 3.6 nmol/kg F027500069 led to a numerically superior suppression of skin swelling.

Skin biopsies were taken at day 5 and mRNA was prepared using standard methods. mRNA was subjected to paired-end, bulk based whole transcriptome sequencing on an Ilumina NovaSeg™ 6000 platform. Genes differentially expressed versus NAb ctrl (DEGs, fold change >2 at p<0.001) were analyzed for overlap between treatment groups. As shown in FIG. 15, despite large overlap of the monospecific treatment groups with the multispecific treatment group, still 199 out of 769 DEGs were specific for F027500069 treatment. This indicates that dual targeting of both TNFα and IL-23 in this model led to a unique molecular response and possibly synergistic amelioration of human disease.

In conclusion, the results demonstrate that multispecific inhibition of both IL-23 and TNFα in the IL-23 induced skin inflammation led to numerically additive effects on skin thickening and elicited a unique transcriptomic profile.

INDUSTRIAL APPLICABILITY

The polypeptides, nucleic acid molecules encoding the same, vectors comprising the nucleic acids and compositions described herein may be used for example in the treatment, such as treatment of subjects suffering from inflammatory bowel disease, psoriasis, psoriatic arthritis or Hidradenitis suppurativa.

The invention claimed is:

1. A method of treating an autoimmune or inflammatory disease that comprises IL-23-mediated inflammation or both TNFα-mediated inflammation and IL-23 mediated inflammation, wherein said method comprises administering, to a subject in need thereof, a pharmaceutically active amount of a polypeptide or a composition comprising the same, wherein the polypeptide specifically binds TNFα and the p19 subunit of IL-23, wherein the polypeptide comprises at least three immunoglobulin single variable domains (ISVDs), wherein each of said ISVDs comprises three complementarity determining regions (CDR1 to CDR3, respectively), optionally linked via one or more peptidic linkers; and wherein:

a) a first ISVD comprises
   i. a CDR1 that is the amino acid sequence of SEQ ID NO: 6;
   ii. a CDR2 that is the amino acid sequence of SEQ ID NO: 10; and
   iii. a CDR3 that is the amino acid sequence of SEQ ID NO: 14;
b) a second ISVD comprises
   iv. a CDR1 that is the amino acid sequence of SEQ ID NO: 7;
   v. a CDR2 that is the amino acid sequence of SEQ ID NO: 11; and
   vi. a CDR3 that is the amino acid sequence of SEQ ID NO: 15; and
c) a third ISVD comprises
   vii. a CDR1 that is the amino acid sequence of SEQ ID NO: 9;
   viii. a CDR2 that is the amino acid sequence of SEQ ID NO: 13; and
   ix. a CDR3 that is the amino acid sequence of SEQ ID NO: 17.

2. The method according to claim 1, wherein:

a) said first ISVD consists of the amino acid sequence of SEQ ID NO: 2;
b) said second ISVD consists of the amino acid sequence of SEQ ID NO: 3; and
c) said third ISVD consists of the amino acid sequence of SEQ ID NO: 5.

3. The method according to claim 1, wherein said polypeptide further comprises an ISVD that binds to human serum albumin which comprises i. a CDR1 that is the amino acid sequence of SEQ ID NO: 8;
ii. a CDR2 that is the amino acid sequence of SEQ ID NO: 12; and
iii. a CDR3 that is the amino acid sequence of SEQ ID NO: 16.

4. The method according to claim 1, wherein the polypeptide consists of four immunoglobulin single variable domains (ISVDs), wherein each of said ISVDs comprises three complementarity determining regions (CDR1 to CDR3, respectively), optionally linked via one or more peptidic linkers; and wherein:

a) a first ISVD comprises
   i. a CDR1 that is the amino acid sequence of SEQ ID NO: 6;
   ii. a CDR2 that is the amino acid sequence of SEQ ID NO: 10; and
   iii. a CDR3 that is the amino acid sequence of SEQ ID NO: 14;
b) a second ISVD comprises
   iv. a CDR1 that is the amino acid sequence of SEQ ID NO: 7;
   v. a CDR2 that is the amino acid sequence of SEQ ID NO: 11; and
   vi. a CDR3 that is the amino acid sequence of SEQ ID NO: 15;
c) a third ISVD comprises
   vii. a CDR1 that is the amino acid sequence of SEQ ID NO: 9;
   viii. a CDR2 that is the amino acid sequence of SEQ ID NO: 13; and ix. a CDR3 that is the amino acid sequence of SEQ ID NO: 17; and d) a fourth ISVD comprises x. a CDR1 that is the amino acid sequence of SEQ ID NO: 8;

xi. a CDR2 that is the amino acid sequence of SEQ ID NO: 12; and xii. a CDR3 that is the amino acid sequence of SEQ ID NO: 16.

5. The method according to claim 4, wherein:

a) said first ISVD consists of the amino acid sequence of SEQ ID NO: 2;

b) said second ISVD consists of the amino acid sequence of SEQ ID NO: 3;

c) said third ISVD consists of the amino acid sequence of SEQ ID NO: 5; and d) said fourth ISVD consists of the amino acid sequence of SEQ ID NO: 4.

6. The method according to claim 1, wherein the autoimmune or inflammatory disease is an inflammatory bowel disease, psoriasis, psoriatic arthritis, or Hidradenitis suppurativa.

7. The method of claim 2, wherein the autoimmune or inflammatory disease is an inflammatory bowel disease, psoriasis, psoriatic arthritis, or Hidradenitis suppurativa.

8. The method of claim 3, wherein the autoimmune or inflammatory disease is an inflammatory bowel disease, psoriasis, psoriatic arthritis, or Hidradenitis suppurativa.

9. The method of claim 4, wherein the autoimmune or inflammatory disease is an inflammatory bowel disease, psoriasis, psoriatic arthritis, or Hidradenitis suppurativa.

10. The method of claim 5, wherein the autoimmune or inflammatory disease is an inflammatory bowel disease, psoriasis, psoriatic arthritis, or Hidradenitis suppurativa.

11. The method of claim 1, wherein the autoimmune or inflammatory disease is an inflammatory bowel disease.

12. The method of claim 11, wherein the inflammatory bowel disease is Crohn's disease.

13. The method of claim 11, wherein the inflammatory bowel disease is ulcerative colitis.

14. The method of claim 1, wherein the autoimmune or inflammatory disease is psoriasis.

15. The method of claim 1, wherein the autoimmune or inflammatory disease is psoriatic arthritis.

16. The method of claim 1, wherein the autoimmune or inflammatory disease is Hidradenitis suppurativa.

17. A method of treating an autoimmune or inflammatory disease that comprises IL-23-mediated inflammation or both TNFα-mediated inflammation and IL-23 mediated inflammation, wherein said method comprises administering, to a subject in need thereof, a pharmaceutically active amount of a polypeptide or a composition comprising the same, wherein the polypeptide specifically binds TNFα and the p19 subunit of IL-23, wherein the polypeptide comprises the amino acid sequence of SEQ ID NO: 1.

18. The method according to claim 17, wherein the polypeptide consists of the amino acid sequence of SEQ ID NO: 1.

19. The method of claim 17, wherein the autoimmune or inflammatory disease is an inflammatory bowel disease, psoriasis, psoriatic arthritis, or Hidradenitis suppurativa.

20. The method of claim 18, wherein the autoimmune or inflammatory disease is an inflammatory bowel disease, psoriasis, psoriatic arthritis, or Hidradenitis suppurativa.

* * * * *

SEQUENCE LISTING

<160> NUMBER OF SEQ ID NOS: 157

<210> SEQ ID NO 1
<211> LENGTH: 517
<212> TYPE: PRT
<213> ORGANISM: Artificial Sequence
<220> FEATURE:
<223> OTHER INFORMATION: F027500069

<400> SEQUENCE: 1

Asp Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ala Arg Ile Ser Gly Ile Asp Gly Thr Thr Tyr Tyr Asp Glu Pro Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Ser Ser Gly Gly Gly Gly Ser Gly Gly
        115                 120                 125

Gly Ser Glu Val Gln Leu Val Glu Ser Gly Gly Gly Val Val Gln Pro
    130                 135                 140

Gly Gly Ser Leu Arg Leu Ser Cys Ala Ala Ser Gly Arg Ile Phe Ser
145                 150                 155                 160

Leu Pro Ala Ser Gly Asn Ile Phe Asn Leu Leu Thr Ile Ala Trp Tyr
                165                 170                 175

Arg Gln Ala Pro Gly Lys Gln Arg Glu Leu Val Ala Thr Ile Glu Ser
            180                 185                 190

Gly Ser Arg Thr Asn Tyr Ala Asp Ser Val Lys Gly Arg Phe Thr Ile
        195                 200                 205

Ser Arg Asp Asn Ser Lys Lys Thr Val Tyr Leu Gln Met Asn Ser Leu
    210                 215                 220

Arg Pro Glu Asp Thr Ala Leu Tyr Tyr Cys Gln Thr Ser Gly Ser Gly
225                 230                 235                 240

Ser Pro Asn Phe Trp Gly Gln Gly Thr Leu Val Thr Val Ser Ser Gly
                245                 250                 255

Gly Gly Gly Ser Gly Gly Gly Ser Glu Val Gln Leu Val Glu Ser Gly
            260                 265                 270

Gly Gly Val Val Gln Pro Gly Gly Ser Leu Arg Leu Ser Cys Ala Ala
        275                 280                 285

Ser Gly Phe Thr Phe Arg Ser Phe Gly Met Ser Trp Val Arg Gln Ala
    290                 295                 300

Pro Gly Lys Gly Pro Glu Trp Val Ser Ser Ile Ser Gly Ser Gly Ser
305                 310                 315                 320

Asp Thr Leu Tyr Ala Asp Ser Val Lys Gly Arg Phe Thr Ile Ser Arg
                325                 330                 335

Asp Asn Ser Lys Asn Thr Leu Tyr Leu Gln Met Asn Ser Leu Arg Pro
            340                 345                 350

Glu Asp Thr Ala Leu Tyr Tyr Cys Thr Ile Gly Gly Ser Leu Ser Arg

```
        355                 360                 365

Ser Ser Gln Gly Thr Leu Val Thr Val Ser Ser Gly Gly Gly Gly Ser
    370                 375                 380

Gly Gly Gly Ser Glu Val Gln Leu Val Glu Ser Gly Gly Gly Val Val
385                 390                 395                 400

Gln Pro Gly Gly Ser Leu Arg Leu Ser Cys Ala Ala Ser Gly Arg Thr
                405                 410                 415

Leu Ser Ser Tyr Ala Met Gly Trp Phe Arg Gln Ala Pro Gly Lys Glu
            420                 425                 430

Arg Glu Phe Val Ala Arg Ile Ser Gln Gly Gly Thr Ala Ile Tyr Tyr
        435                 440                 445

Ala Asp Ser Val Lys Gly Arg Phe Thr Ile Ser Arg Asp Asn Ser Lys
    450                 455                 460

Asn Thr Val Tyr Leu Gln Met Asn Ser Leu Arg Pro Glu Asp Thr Ala
465                 470                 475                 480

Leu Tyr Tyr Cys Ala Lys Asp Pro Ser Pro Tyr Tyr Arg Gly Ser Ala
                485                 490                 495

Tyr Leu Leu Ser Gly Ser Tyr Asp Ser Trp Gly Gln Gly Thr Leu Val
            500                 505                 510

Lys Val Ser Ser Ala
        515


<210> SEQ ID NO 2
<211> LENGTH: 121
<212> TYPE: PRT
<213> ORGANISM: Artificial Sequence
<220> FEATURE:
<223> OTHER INFORMATION: 6C11

<400> SEQUENCE: 2

Asp Val Gln Leu Val Glu Ser Gly Gly Gly Val Val Gln Pro Gly Gly
1               5                   10                  15

Ser Leu Arg Leu Ser Cys Thr Ala Ser Gly Phe Thr Phe Ser Thr Ala
            20                  25                  30

Asp Met Gly Trp Phe Arg Gln Ala Pro Gly Lys Gly Arg Glu Phe Val
        35                  40                  45

Ala Arg Ile Ser Gly Ile Asp Gly Thr Thr Tyr Tyr Asp Glu Pro Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Arg Ser Pro Arg Tyr Ala Asp Gln Trp Ser Ala Tyr Asp Tyr Trp Gly
            100                 105                 110

Gln Gly Thr Leu Val Thr Val Ser Ser
        115                 120


<210> SEQ ID NO 3
<211> LENGTH: 125
<212> TYPE: PRT
<213> ORGANISM: Artificial Sequence
<220> FEATURE:
<223> OTHER INFORMATION: 119A03/1

<400> SEQUENCE: 3

Glu Val Gln Leu Val Glu Ser Gly Gly Gly Val Val Gln Pro Gly Gly
1               5                   10                  15
```

Ser Leu Arg Leu Ser Cys Ala Ala Ser Gly Arg Ile Phe Ser Leu Pro
20 25 30

Ala Ser Gly Asn Ile Phe Asn Leu Leu Thr Ile Ala Trp Tyr Arg Gln
35 40 45

Ala Pro Gly Lys Gln Arg Glu Leu Val Ala Thr Ile Glu Ser Gly Ser
50 55 60

Arg Thr Asn Tyr Ala Asp Ser Val Lys Gly Arg Phe Thr Ile Ser Arg
65 70 75 80

Asp Asn Ser Lys Lys Thr Val Tyr Leu Gln Met Asn Ser Leu Arg Pro
85 90 95

Glu Asp Thr Ala Leu Tyr Tyr Cys Gln Thr Ser Gly Ser Gly Ser Pro
100 105 110

Asn Phe Trp Gly Gln Gly Thr Leu Val Thr Val Ser Ser
115 120 125

<210> SEQ ID NO 4
<211> LENGTH: 115
<212> TYPE: PRT
<213> ORGANISM: Artificial Sequence
<220> FEATURE:
<223> OTHER INFORMATION: ALB23002

<400> SEQUENCE: 4

Glu Val Gln Leu Val Glu Ser Gly Gly Gly Val Val Gln Pro Gly Gly
1 5 10 15

Ser Leu Arg Leu Ser Cys Ala Ala Ser Gly Phe Thr Phe Arg Ser Phe
20 25 30

Gly Met Ser Trp Val Arg Gln Ala Pro Gly Lys Gly Pro Glu Trp Val
35 40 45

Ser Ser Ile Ser Gly Ser Gly Ser Asp Thr Leu Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Pro Glu Asp Thr Ala Leu Tyr Tyr Cys
85 90 95

Thr Ile Gly Gly Ser Leu Ser Arg Ser Ser Gln Gly Thr Leu Val Thr
100 105 110

Val Ser Ser
115

<210> SEQ ID NO 5
<211> LENGTH: 128
<212> TYPE: PRT
<213> ORGANISM: Artificial Sequence
<220> FEATURE:
<223> OTHER INFORMATION: 81A12

<400> SEQUENCE: 5

Glu Val Gln Leu Val Glu Ser Gly Gly Gly Val Val Gln Pro Gly Gly
1 5 10 15

Ser Leu Arg Leu Ser Cys Ala Ala Ser Gly Arg Thr Leu Ser Ser Tyr
20 25 30

Ala Met Gly Trp Phe Arg Gln Ala Pro Gly Lys Glu Arg Glu Phe Val
35 40 45

Ala Arg Ile Ser Gln Gly Gly Thr Ala Ile Tyr Tyr Ala Asp Ser Val
50 55 60

Lys Gly Arg Phe Thr Ile Ser Arg Asp Asn Ser Lys Asn Thr Val Tyr
65 70 75 80

```
Leu Gln Met Asn Ser Leu Arg Pro Glu Asp Thr Ala Leu Tyr Tyr Cys
                85                  90                  95

Ala Lys Asp Pro Ser Pro Tyr Tyr Arg Gly Ser Ala Tyr Leu Leu Ser
            100                 105                 110

Gly Ser Tyr Asp Ser Trp Gly Gln Gly Thr Leu Val Lys Val Ser Ser
        115                 120                 125


<210> SEQ ID NO 6
<211> LENGTH: 10
<212> TYPE: PRT
<213> ORGANISM: Artificial Sequence
<220> FEATURE:
<223> OTHER INFORMATION: CDR1

<400> SEQUENCE: 6

Gly Phe Thr Phe Ser Thr Ala Asp Met Gly
1               5                   10


<210> SEQ ID NO 7
<211> LENGTH: 19
<212> TYPE: PRT
<213> ORGANISM: Artificial Sequence
<220> FEATURE:
<223> OTHER INFORMATION: CDR1

<400> SEQUENCE: 7

Gly Arg Ile Phe Ser Leu Pro Ala Ser Gly Asn Ile Phe Asn Leu Leu
1               5                   10                  15

Thr Ile Ala


<210> SEQ ID NO 8
<211> LENGTH: 10
<212> TYPE: PRT
<213> ORGANISM: Artificial Sequence
<220> FEATURE:
<223> OTHER INFORMATION: CDR1

<400> SEQUENCE: 8

Gly Phe Thr Phe Arg Ser Phe Gly Met Ser
1               5                   10


<210> SEQ ID NO 9
<211> LENGTH: 10
<212> TYPE: PRT
<213> ORGANISM: Artificial Sequence
<220> FEATURE:
<223> OTHER INFORMATION: CDR1

<400> SEQUENCE: 9

Gly Arg Thr Leu Ser Ser Tyr Ala Met Gly
1               5                   10


<210> SEQ ID NO 10
<211> LENGTH: 10
<212> TYPE: PRT
<213> ORGANISM: Artificial Sequence
<220> FEATURE:
<223> OTHER INFORMATION: CDR2

<400> SEQUENCE: 10

Arg Ile Ser Gly Ile Asp Gly Thr Thr Tyr
1               5                   10


<210> SEQ ID NO 11
```

<211> LENGTH: 9
<212> TYPE: PRT
<213> ORGANISM: Artificial Sequence
<220> FEATURE:
<223> OTHER INFORMATION: CDR2

<400> SEQUENCE: 11

Thr Ile Glu Ser Gly Ser Arg Thr Asn
1               5

<210> SEQ ID NO 12
<211> LENGTH: 10
<212> TYPE: PRT
<213> ORGANISM: Artificial Sequence
<220> FEATURE:
<223> OTHER INFORMATION: CDR2

<400> SEQUENCE: 12

Ser Ile Ser Gly Ser Gly Ser Asp Thr Leu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: CDR2

<400> SEQUENCE: 13

Arg Ile Ser Gln Gly Gly Thr Ala Ile Tyr
1               5                   10

<210> SEQ ID NO 14
<211> LENGTH: 12
<212> TYPE: PRT
<213> ORGANISM: Artificial Sequence
<220> FEATURE:
<223> OTHER INFORMATION: CDR3

<400> SEQUENCE: 14

Pro Arg Tyr Ala Asp Gln Trp Ser Ala Tyr Asp Tyr
1               5                   10

<210> SEQ ID NO 15
<211> LENGTH: 8
<212> TYPE: PRT
<213> ORGANISM: Artificial Sequence
<220> FEATURE:
<223> OTHER INFORMATION: CDR3

<400> SEQUENCE: 15

Ser Gly Ser Gly Ser Pro Asn Phe
1               5

<210> SEQ ID NO 16
<211> LENGTH: 6
<212> TYPE: PRT
<213> ORGANISM: Artificial Sequence
<220> FEATURE:
<223> OTHER INFORMATION: CDR3

<400> SEQUENCE: 16

Gly Gly Ser Leu Ser Arg
1               5

<210> SEQ ID NO 17
<211> LENGTH: 19

<212> TYPE: PRT
<213> ORGANISM: Artificial Sequence
<220> FEATURE:
<223> OTHER INFORMATION: CDR3

<400> SEQUENCE: 17

Asp Pro Ser Pro Tyr Tyr Arg Gly Ser Ala Tyr Leu Leu Ser Gly Ser
1 5 10 15

Tyr Asp Ser

<210> SEQ ID NO 18
<211> LENGTH: 25
<212> TYPE: PRT
<213> ORGANISM: Artificial Sequence
<220> FEATURE:
<223> OTHER INFORMATION: FR1

<400> SEQUENCE: 18

Asp Val Gln Leu Val Glu Ser Gly Gly Gly Val Val Gln Pro Gly Gly
1 5 10 15

Ser Leu Arg Leu Ser Cys Thr Ala Ser
20 25

<210> SEQ ID NO 19
<211> LENGTH: 25
<212> TYPE: PRT
<213> ORGANISM: Artificial Sequence
<220> FEATURE:
<223> OTHER INFORMATION: FR1

<400> SEQUENCE: 19

Glu Val Gln Leu Val Glu Ser Gly Gly Gly Val Val Gln Pro Gly Gly
1 5 10 15

Ser Leu Arg Leu Ser Cys Ala Ala Ser
20 25

<210> SEQ ID NO 20
<211> LENGTH: 14
<212> TYPE: PRT
<213> ORGANISM: Artificial Sequence
<220> FEATURE:
<223> OTHER INFORMATION: FR2

<400> SEQUENCE: 20

Trp Phe Arg Gln Ala Pro Gly Lys Gly Arg Glu Phe Val Ala
1 5 10

<210> SEQ ID NO 21
<211> LENGTH: 14
<212> TYPE: PRT
<213> ORGANISM: Artificial Sequence
<220> FEATURE:
<223> OTHER INFORMATION: FR2

<400> SEQUENCE: 21

Trp Tyr Arg Gln Ala Pro Gly Lys Gln Arg Glu Leu Val Ala
1 5 10

<210> SEQ ID NO 22
<211> LENGTH: 14
<212> TYPE: PRT
<213> ORGANISM: Artificial Sequence
<220> FEATURE:
<223> OTHER INFORMATION: FR2

<400> SEQUENCE: 22

Trp Val Arg Gln Ala Pro Gly Lys Gly Pro Glu Trp Val Ser
1 5 10

<210> SEQ ID NO 23
<211> LENGTH: 14
<212> TYPE: PRT
<213> ORGANISM: Artificial Sequence
<220> FEATURE:
<223> OTHER INFORMATION: FR2

<400> SEQUENCE: 23

Trp Phe Arg Gln Ala Pro Gly Lys Glu Arg Glu Phe Val Ala
1 5 10

<210> SEQ ID NO 24
<211> LENGTH: 39
<212> TYPE: PRT
<213> ORGANISM: Artificial Sequence
<220> FEATURE:
<223> OTHER INFORMATION: FR3

<400> SEQUENCE: 24

Tyr Asp Glu Pro Val Lys Gly Arg Phe Thr Ile Ser Arg Asp Asn Ser
1 5 10 15

Lys Asn Thr Val Tyr Leu Gln Met Asn Ser Leu Arg Pro Glu Asp Thr
20 25 30

Ala Leu Tyr Tyr Cys Arg Ser
35

<210> SEQ ID NO 25
<211> LENGTH: 39
<212> TYPE: PRT
<213> ORGANISM: Artificial Sequence
<220> FEATURE:
<223> OTHER INFORMATION: FR3

<400> SEQUENCE: 25

Tyr Ala Asp Ser Val Lys Gly Arg Phe Thr Ile Ser Arg Asp Asn Ser
1 5 10 15

Lys Lys Thr Val Tyr Leu Gln Met Asn Ser Leu Arg Pro Glu Asp Thr
20 25 30

Ala Leu Tyr Tyr Cys Gln Thr
35

<210> SEQ ID NO 26
<211> LENGTH: 39
<212> TYPE: PRT
<213> ORGANISM: Artificial Sequence
<220> FEATURE:
<223> OTHER INFORMATION: FR3

<400> SEQUENCE: 26

Tyr Ala Asp Ser Val Lys Gly Arg Phe Thr Ile Ser Arg Asp Asn Ser
1 5 10 15

Lys Asn Thr Leu Tyr Leu Gln Met Asn Ser Leu Arg Pro Glu Asp Thr
20 25 30

Ala Leu Tyr Tyr Cys Thr Ile
35

<210> SEQ ID NO 27
<211> LENGTH: 39
<212> TYPE: PRT
<213> ORGANISM: Artificial Sequence

<220> FEATURE:
<223> OTHER INFORMATION: FR3

<400> SEQUENCE: 27

Tyr Ala Asp Ser Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Leu Tyr Tyr Cys Ala Lys
        35

<210> SEQ ID NO 28
<211> LENGTH: 11
<212> TYPE: PRT
<213> ORGANISM: Artificial Sequence
<220> FEATURE:
<223> OTHER INFORMATION: FR4

<400> SEQUENCE: 28

Trp Gly Gln Gly Thr Leu Val Thr Val Ser Ser
1               5                   10

<210> SEQ ID NO 29
<211> LENGTH: 11
<212> TYPE: PRT
<213> ORGANISM: Artificial Sequence
<220> FEATURE:
<223> OTHER INFORMATION: FR4

<400> SEQUENCE: 29

Ser Ser Gln Gly Thr Leu Val Thr Val Ser Ser
1               5                   10

<210> SEQ ID NO 30
<211> LENGTH: 11
<212> TYPE: PRT
<213> ORGANISM: Artificial Sequence
<220> FEATURE:
<223> OTHER INFORMATION: FR4

<400> SEQUENCE: 30

Trp Gly Gln Gly Thr Leu Val Lys Val Ser Ser
1               5                   10

<210> SEQ ID NO 31
<211> LENGTH: 115
<212> TYPE: PRT
<213> ORGANISM: Artificial Sequence
<220> FEATURE:
<223> OTHER INFORMATION: Alb8

<400> SEQUENCE: 31

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys

```
                85                  90                  95

Thr Ile Gly Gly Ser Leu Ser Arg Ser Ser Gln Gly Thr Leu Val Thr
            100                 105                 110

Val Ser Ser
        115


<210> SEQ ID NO 32
<211> LENGTH: 115
<212> TYPE: PRT
<213> ORGANISM: Artificial Sequence
<220> FEATURE:
<223> OTHER INFORMATION: Alb23

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115


<210> SEQ ID NO 33
<211> LENGTH: 116
<212> TYPE: PRT
<213> ORGANISM: Artificial Sequence
<220> FEATURE:
<223> OTHER INFORMATION: Alb129

<400> SEQUENCE: 33

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115


<210> SEQ ID NO 34
<211> LENGTH: 116
```

<212> TYPE: PRT
<213> ORGANISM: Artificial Sequence
<220> FEATURE:
<223> OTHER INFORMATION: Alb132

<400> SEQUENCE: 34

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115
```

<210> SEQ ID NO 35
<211> LENGTH: 115
<212> TYPE: PRT
<213> ORGANISM: Artificial Sequence
<220> FEATURE:
<223> OTHER INFORMATION: Alb11

<400> SEQUENCE: 35

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115
```

<210> SEQ ID NO 36
<211> LENGTH: 116
<212> TYPE: PRT
<213> ORGANISM: Artificial Sequence
<220> FEATURE:
<223> OTHER INFORMATION: Alb11 (S112K)-A

<400> SEQUENCE: 36

```
Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
```

```
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Lys
            100                 105                 110

Val Ser Ser Ala
        115


<210> SEQ ID NO 37
<211> LENGTH: 115
<212> TYPE: PRT
<213> ORGANISM: Artificial Sequence
<220> FEATURE:
<223> OTHER INFORMATION: Alb82

<400> SEQUENCE: 37

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115


<210> SEQ ID NO 38
<211> LENGTH: 116
<212> TYPE: PRT
<213> ORGANISM: Artificial Sequence
<220> FEATURE:
<223> OTHER INFORMATION: Alb82-A

<400> SEQUENCE: 38

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80
```

```
Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115


<210> SEQ ID NO 39
<211> LENGTH: 117
<212> TYPE: PRT
<213> ORGANISM: Artificial Sequence
<220> FEATURE:
<223> OTHER INFORMATION: Alb82-AA

<400> SEQUENCE: 39

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala
        115


<210> SEQ ID NO 40
<211> LENGTH: 118
<212> TYPE: PRT
<213> ORGANISM: Artificial Sequence
<220> FEATURE:
<223> OTHER INFORMATION: Alb82-AAA

<400> SEQUENCE: 40

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala Ala
        115


<210> SEQ ID NO 41
```

<211> LENGTH: 116
<212> TYPE: PRT
<213> ORGANISM: Artificial Sequence
<220> FEATURE:
<223> OTHER INFORMATION: Alb82-G

<400> SEQUENCE: 41

```
Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly
        115
```

<210> SEQ ID NO 42
<211> LENGTH: 117
<212> TYPE: PRT
<213> ORGANISM: Artificial Sequence
<220> FEATURE:
<223> OTHER INFORMATION: Alb82-GG

<400> SEQUENCE: 42

```
Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly
        115
```

<210> SEQ ID NO 43
<211> LENGTH: 118
<212> TYPE: PRT
<213> ORGANISM: Artificial Sequence
<220> FEATURE:
<223> OTHER INFORMATION: Alb82-GGG

<400> SEQUENCE: 43

```
Glu Val Gln Leu Val Glu Ser Gly Gly Gly Val Val Gln Pro Gly Asn
1               5                   10                  15
```

```
Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly
        115


<210> SEQ ID NO 44
<211> LENGTH: 115
<212> TYPE: PRT
<213> ORGANISM: Artificial Sequence
<220> FEATURE:
<223> OTHER INFORMATION: Alb23002

<400> SEQUENCE: 44

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser
        115


<210> SEQ ID NO 45
<211> LENGTH: 116
<212> TYPE: PRT
<213> ORGANISM: Artificial Sequence
<220> FEATURE:
<223> OTHER INFORMATION: Alb223

<400> SEQUENCE: 45

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Pro Glu Asp Thr Ala Leu Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115


<210> SEQ ID NO 46
<211> LENGTH: 3
<212> TYPE: PRT
<213> ORGANISM: Artificial Sequence
<220> FEATURE:
<223> OTHER INFORMATION: 3A

<400> SEQUENCE: 46

Ala Ala Ala
1


<210> SEQ ID NO 47
<211> LENGTH: 5
<212> TYPE: PRT
<213> ORGANISM: Artificial Sequence
<220> FEATURE:
<223> OTHER INFORMATION: 5GS

<400> SEQUENCE: 47

Gly Gly Gly Gly Ser
1               5


<210> SEQ ID NO 48
<211> LENGTH: 7
<212> TYPE: PRT
<213> ORGANISM: Artificial Sequence
<220> FEATURE:
<223> OTHER INFORMATION: 7GS

<400> SEQUENCE: 48

Ser Gly Gly Ser Gly Gly Ser
1               5


<210> SEQ ID NO 49
<211> LENGTH: 8
<212> TYPE: PRT
<213> ORGANISM: Artificial Sequence
<220> FEATURE:
<223> OTHER INFORMATION: 8GS

<400> SEQUENCE: 49

Gly Gly Gly Gly Ser Gly Gly Ser
1               5


<210> SEQ ID NO 50
<211> LENGTH: 9
<212> TYPE: PRT
<213> ORGANISM: Artificial Sequence
<220> FEATURE:
<223> OTHER INFORMATION: 9GS

<400> SEQUENCE: 50

Gly Gly Gly Gly Ser Gly Gly Gly Ser
1               5


<210> SEQ ID NO 51
<211> LENGTH: 10
<212> TYPE: PRT
```

<213> ORGANISM: Artificial Sequence
<220> FEATURE:
<223> OTHER INFORMATION: 10GS

<400> SEQUENCE: 51

Gly Gly Gly Gly Ser Gly Gly Gly Gly Ser
1 5 10

<210> SEQ ID NO 52
<211> LENGTH: 15
<212> TYPE: PRT
<213> ORGANISM: Artificial Sequence
<220> FEATURE:
<223> OTHER INFORMATION: 15GS

<400> SEQUENCE: 52

Gly Gly Gly Gly Ser Gly Gly Gly Gly Ser Gly Gly Gly Gly Ser
1 5 10 15

<210> SEQ ID NO 53
<211> LENGTH: 18
<212> TYPE: PRT
<213> ORGANISM: Artificial Sequence
<220> FEATURE:
<223> OTHER INFORMATION: 18GS

<400> SEQUENCE: 53

Gly Gly Gly Gly Ser Gly Gly Gly Gly Ser Gly Gly Gly Gly Ser Gly
1 5 10 15

Gly Ser

<210> SEQ ID NO 54
<211> LENGTH: 20
<212> TYPE: PRT
<213> ORGANISM: Artificial Sequence
<220> FEATURE:
<223> OTHER INFORMATION: 20GS

<400> SEQUENCE: 54

Gly Gly Gly Gly Ser Gly Gly Gly Gly Ser Gly Gly Gly Gly Ser Gly
1 5 10 15

Gly Gly Gly Ser
20

<210> SEQ ID NO 55
<211> LENGTH: 25
<212> TYPE: PRT
<213> ORGANISM: Artificial Sequence
<220> FEATURE:
<223> OTHER INFORMATION: 25GS

<400> SEQUENCE: 55

Gly Gly Gly Gly Ser Gly Gly Gly Gly Ser Gly Gly Gly Gly Ser Gly
1 5 10 15

Gly Gly Gly Ser Gly Gly Gly Gly Ser
20 25

<210> SEQ ID NO 56
<211> LENGTH: 30
<212> TYPE: PRT
<213> ORGANISM: Artificial Sequence
<220> FEATURE:
<223> OTHER INFORMATION: 30GS

<400> SEQUENCE: 56

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser
20 25 30

<210> SEQ ID NO 57
<211> LENGTH: 35
<212> TYPE: PRT
<213> ORGANISM: Artificial Sequence
<220> FEATURE:
<223> OTHER INFORMATION: 35GS

<400> SEQUENCE: 57

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser
35

<210> SEQ ID NO 58
<211> LENGTH: 40
<212> TYPE: PRT
<213> ORGANISM: Artificial Sequence
<220> FEATURE:
<223> OTHER INFORMATION: 40GS

<400> SEQUENCE: 58

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser
35 40

<210> SEQ ID NO 59
<211> LENGTH: 15
<212> TYPE: PRT
<213> ORGANISM: Artificial Sequence
<220> FEATURE:
<223> OTHER INFORMATION: G1 hinge

<400> SEQUENCE: 59

Glu Pro Lys Ser Cys Asp Lys Thr His Thr Cys Pro Pro Cys Pro
1 5 10 15

<210> SEQ ID NO 60
<211> LENGTH: 24
<212> TYPE: PRT
<213> ORGANISM: Artificial Sequence
<220> FEATURE:
<223> OTHER INFORMATION: 9GS-G1 hinge

<400> SEQUENCE: 60

Gly Gly Gly Gly Ser Gly Gly Gly Ser Glu Pro Lys Ser Cys Asp Lys
1 5 10 15

Thr His Thr Cys Pro Pro Cys Pro
20

<210> SEQ ID NO 61
<211> LENGTH: 12
<212> TYPE: PRT
<213> ORGANISM: Artificial Sequence
<220> FEATURE:

<223> OTHER INFORMATION: Llama upper long hinge region

<400> SEQUENCE: 61

Glu Pro Lys Thr Pro Lys Pro Gln Pro Ala Ala Ala
1               5                   10

<210> SEQ ID NO 62
<211> LENGTH: 62
<212> TYPE: PRT
<213> ORGANISM: Artificial Sequence
<220> FEATURE:
<223> OTHER INFORMATION: G3 hinge

<400> SEQUENCE: 62

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Glu
        35                  40                  45

Pro Lys Ser Cys Asp Thr Pro Pro Pro Cys Pro Arg Cys Pro
    50                  55                  60

<210> SEQ ID NO 63
<211> LENGTH: 4
<212> TYPE: PRT
<213> ORGANISM: Artificial Sequence
<220> FEATURE:
<223> OTHER INFORMATION: Motif

<400> SEQUENCE: 63

Lys Glu Arg Glu
1

<210> SEQ ID NO 64
<211> LENGTH: 4
<212> TYPE: PRT
<213> ORGANISM: Artificial Sequence
<220> FEATURE:
<223> OTHER INFORMATION: Motif

<400> SEQUENCE: 64

Lys Gln Arg Glu
1

<210> SEQ ID NO 65
<211> LENGTH: 4
<212> TYPE: PRT
<213> ORGANISM: Artificial Sequence
<220> FEATURE:
<223> OTHER INFORMATION: Motif

<400> SEQUENCE: 65

Gly Leu Glu Trp
1

<210> SEQ ID NO 66
<211> LENGTH: 5
<212> TYPE: PRT
<213> ORGANISM: Artificial Sequence
<220> FEATURE:
<223> OTHER INFORMATION: Motif

<400> SEQUENCE: 66

Lys Glu Arg Glu Leu

```
1               5


<210> SEQ ID NO 67
<211> LENGTH: 5
<212> TYPE: PRT
<213> ORGANISM: Artificial Sequence
<220> FEATURE:
<223> OTHER INFORMATION: Motif

<400> SEQUENCE: 67

Lys Glu Arg Glu Phe
1               5


<210> SEQ ID NO 68
<211> LENGTH: 5
<212> TYPE: PRT
<213> ORGANISM: Artificial Sequence
<220> FEATURE:
<223> OTHER INFORMATION: Motif

<400> SEQUENCE: 68

Lys Gln Arg Glu Leu
1               5


<210> SEQ ID NO 69
<211> LENGTH: 5
<212> TYPE: PRT
<213> ORGANISM: Artificial Sequence
<220> FEATURE:
<223> OTHER INFORMATION: Motif

<400> SEQUENCE: 69

Lys Gln Arg Glu Phe
1               5


<210> SEQ ID NO 70
<211> LENGTH: 5
<212> TYPE: PRT
<213> ORGANISM: Artificial Sequence
<220> FEATURE:
<223> OTHER INFORMATION: Motif

<400> SEQUENCE: 70

Lys Glu Arg Glu Gly
1               5


<210> SEQ ID NO 71
<211> LENGTH: 5
<212> TYPE: PRT
<213> ORGANISM: Artificial Sequence
<220> FEATURE:
<223> OTHER INFORMATION: Motif

<400> SEQUENCE: 71

Lys Gln Arg Glu Trp
1               5


<210> SEQ ID NO 72
<211> LENGTH: 5
<212> TYPE: PRT
<213> ORGANISM: Artificial Sequence
<220> FEATURE:
<223> OTHER INFORMATION: Motif

<400> SEQUENCE: 72

Lys Gln Arg Glu Gly
1               5
```

<210> SEQ ID NO 73
<211> LENGTH: 4
<212> TYPE: PRT
<213> ORGANISM: Artificial Sequence
<220> FEATURE:
<223> OTHER INFORMATION: Motif

<400> SEQUENCE: 73

Thr Glu Arg Glu
1

<210> SEQ ID NO 74
<211> LENGTH: 5
<212> TYPE: PRT
<213> ORGANISM: Artificial Sequence
<220> FEATURE:
<223> OTHER INFORMATION: Motif

<400> SEQUENCE: 74

Thr Glu Arg Glu Leu
1 5

<210> SEQ ID NO 75
<211> LENGTH: 4
<212> TYPE: PRT
<213> ORGANISM: Artificial Sequence
<220> FEATURE:
<223> OTHER INFORMATION: Motif

<400> SEQUENCE: 75

Thr Gln Arg Glu
1

<210> SEQ ID NO 76
<211> LENGTH: 5
<212> TYPE: PRT
<213> ORGANISM: Artificial Sequence
<220> FEATURE:
<223> OTHER INFORMATION: Motif

<400> SEQUENCE: 76

Thr Gln Arg Glu Leu
1 5

<210> SEQ ID NO 77
<211> LENGTH: 4
<212> TYPE: PRT
<213> ORGANISM: Artificial Sequence
<220> FEATURE:
<223> OTHER INFORMATION: Motif

<400> SEQUENCE: 77

Lys Glu Cys Glu
1

<210> SEQ ID NO 78
<211> LENGTH: 5
<212> TYPE: PRT
<213> ORGANISM: Artificial Sequence
<220> FEATURE:
<223> OTHER INFORMATION: Motif

<400> SEQUENCE: 78

Lys Glu Cys Glu Leu
1 5

<210> SEQ ID NO 79
<211> LENGTH: 5
<212> TYPE: PRT
<213> ORGANISM: Artificial Sequence
<220> FEATURE:
<223> OTHER INFORMATION: Motif

<400> SEQUENCE: 79

Lys Glu Cys Glu Arg
1               5

<210> SEQ ID NO 80
<211> LENGTH: 4
<212> TYPE: PRT
<213> ORGANISM: Artificial Sequence
<220> FEATURE:
<223> OTHER INFORMATION: Motif

<400> SEQUENCE: 80

Lys Gln Cys Glu
1

<210> SEQ ID NO 81
<211> LENGTH: 5
<212> TYPE: PRT
<213> ORGANISM: Artificial Sequence
<220> FEATURE:
<223> OTHER INFORMATION: Motif

<400> SEQUENCE: 81

Lys Gln Cys Glu Leu
1               5

<210> SEQ ID NO 82
<211> LENGTH: 4
<212> TYPE: PRT
<213> ORGANISM: Artificial Sequence
<220> FEATURE:
<223> OTHER INFORMATION: Motif

<400> SEQUENCE: 82

Arg Glu Arg Glu
1

<210> SEQ ID NO 83
<211> LENGTH: 5
<212> TYPE: PRT
<213> ORGANISM: Artificial Sequence
<220> FEATURE:
<223> OTHER INFORMATION: Motif

<400> SEQUENCE: 83

Arg Glu Arg Glu Gly
1               5

<210> SEQ ID NO 84
<211> LENGTH: 4
<212> TYPE: PRT
<213> ORGANISM: Artificial Sequence
<220> FEATURE:
<223> OTHER INFORMATION: Motif

<400> SEQUENCE: 84

Arg Gln Arg Glu
1

<210> SEQ ID NO 85
<211> LENGTH: 5
<212> TYPE: PRT
<213> ORGANISM: Artificial Sequence
<220> FEATURE:
<223> OTHER INFORMATION: Motif

<400> SEQUENCE: 85

Arg Gln Arg Glu Leu
1               5

<210> SEQ ID NO 86
<211> LENGTH: 5
<212> TYPE: PRT
<213> ORGANISM: Artificial Sequence
<220> FEATURE:
<223> OTHER INFORMATION: Motif

<400> SEQUENCE: 86

Arg Gln Arg Glu Phe
1               5

<210> SEQ ID NO 87
<211> LENGTH: 5
<212> TYPE: PRT
<213> ORGANISM: Artificial Sequence
<220> FEATURE:
<223> OTHER INFORMATION: Motif

<400> SEQUENCE: 87

Arg Gln Arg Glu Trp
1               5

<210> SEQ ID NO 88
<211> LENGTH: 4
<212> TYPE: PRT
<213> ORGANISM: Artificial Sequence
<220> FEATURE:
<223> OTHER INFORMATION: Motif

<400> SEQUENCE: 88

Gln Glu Arg Glu
1

<210> SEQ ID NO 89
<211> LENGTH: 5
<212> TYPE: PRT
<213> ORGANISM: Artificial Sequence
<220> FEATURE:
<223> OTHER INFORMATION: Motif

<400> SEQUENCE: 89

Gln Glu Arg Glu Gly
1               5

<210> SEQ ID NO 90
<211> LENGTH: 4
<212> TYPE: PRT
<213> ORGANISM: Artificial Sequence
<220> FEATURE:
<223> OTHER INFORMATION: Motif

<400> SEQUENCE: 90

Gln Gln Arg Glu
1

<210> SEQ ID NO 91

<211> LENGTH: 5
<212> TYPE: PRT
<213> ORGANISM: Artificial Sequence
<220> FEATURE:
<223> OTHER INFORMATION: Motif

<400> SEQUENCE: 91

Gln Gln Arg Glu Trp
1 5

<210> SEQ ID NO 92
<211> LENGTH: 5
<212> TYPE: PRT
<213> ORGANISM: Artificial Sequence
<220> FEATURE:
<223> OTHER INFORMATION: Motif

<400> SEQUENCE: 92

Gln Gln Arg Glu Leu
1 5

<210> SEQ ID NO 93
<211> LENGTH: 5
<212> TYPE: PRT
<213> ORGANISM: Artificial Sequence
<220> FEATURE:
<223> OTHER INFORMATION: Motif

<400> SEQUENCE: 93

Gln Gln Arg Glu Phe
1 5

<210> SEQ ID NO 94
<211> LENGTH: 4
<212> TYPE: PRT
<213> ORGANISM: Artificial Sequence
<220> FEATURE:
<223> OTHER INFORMATION: Motif

<400> SEQUENCE: 94

Lys Gly Arg Glu
1

<210> SEQ ID NO 95
<211> LENGTH: 5
<212> TYPE: PRT
<213> ORGANISM: Artificial Sequence
<220> FEATURE:
<223> OTHER INFORMATION: Motif

<400> SEQUENCE: 95

Lys Gly Arg Glu Gly
1 5

<210> SEQ ID NO 96
<211> LENGTH: 4
<212> TYPE: PRT
<213> ORGANISM: Artificial Sequence
<220> FEATURE:
<223> OTHER INFORMATION: Motif

<400> SEQUENCE: 96

Lys Asp Arg Glu
1

<210> SEQ ID NO 97
<211> LENGTH: 5

<212> TYPE: PRT
<213> ORGANISM: Artificial Sequence
<220> FEATURE:
<223> OTHER INFORMATION: Motif

<400> SEQUENCE: 97

Lys Asp Arg Glu Val
1               5

<210> SEQ ID NO 98
<211> LENGTH: 5
<212> TYPE: PRT
<213> ORGANISM: Artificial Sequence
<220> FEATURE:
<223> OTHER INFORMATION: Motif

<400> SEQUENCE: 98

Asp Glu Cys Lys Leu
1               5

<210> SEQ ID NO 99
<211> LENGTH: 5
<212> TYPE: PRT
<213> ORGANISM: Artificial Sequence
<220> FEATURE:
<223> OTHER INFORMATION: Motif

<400> SEQUENCE: 99

Asn Val Cys Glu Leu
1               5

<210> SEQ ID NO 100
<211> LENGTH: 4
<212> TYPE: PRT
<213> ORGANISM: Artificial Sequence
<220> FEATURE:
<223> OTHER INFORMATION: Motif

<400> SEQUENCE: 100

Gly Val Glu Trp
1

<210> SEQ ID NO 101
<211> LENGTH: 4
<212> TYPE: PRT
<213> ORGANISM: Artificial Sequence
<220> FEATURE:
<223> OTHER INFORMATION: Motif

<400> SEQUENCE: 101

Glu Pro Glu Trp
1

<210> SEQ ID NO 102
<211> LENGTH: 4
<212> TYPE: PRT
<213> ORGANISM: Artificial Sequence
<220> FEATURE:
<223> OTHER INFORMATION: Motif

<400> SEQUENCE: 102

Gly Leu Glu Arg
1

<210> SEQ ID NO 103
<211> LENGTH: 4
<212> TYPE: PRT

<213> ORGANISM: Artificial Sequence
<220> FEATURE:
<223> OTHER INFORMATION: Motif

<400> SEQUENCE: 103

Asp Gln Glu Trp
1

<210> SEQ ID NO 104
<211> LENGTH: 4
<212> TYPE: PRT
<213> ORGANISM: Artificial Sequence
<220> FEATURE:
<223> OTHER INFORMATION: Motif

<400> SEQUENCE: 104

Asp Leu Glu Trp
1

<210> SEQ ID NO 105
<211> LENGTH: 4
<212> TYPE: PRT
<213> ORGANISM: Artificial Sequence
<220> FEATURE:
<223> OTHER INFORMATION: Motif

<400> SEQUENCE: 105

Gly Ile Glu Trp
1

<210> SEQ ID NO 106
<211> LENGTH: 4
<212> TYPE: PRT
<213> ORGANISM: Artificial Sequence
<220> FEATURE:
<223> OTHER INFORMATION: Motif

<400> SEQUENCE: 106

Glu Leu Glu Trp
1

<210> SEQ ID NO 107
<211> LENGTH: 4
<212> TYPE: PRT
<213> ORGANISM: Artificial Sequence
<220> FEATURE:
<223> OTHER INFORMATION: Motif

<400> SEQUENCE: 107

Gly Pro Glu Trp
1

<210> SEQ ID NO 108
<211> LENGTH: 4
<212> TYPE: PRT
<213> ORGANISM: Artificial Sequence
<220> FEATURE:
<223> OTHER INFORMATION: Motif

<400> SEQUENCE: 108

Glu Trp Leu Pro
1

<210> SEQ ID NO 109
<211> LENGTH: 4
<212> TYPE: PRT
<213> ORGANISM: Artificial Sequence
<220> FEATURE:
<223> OTHER INFORMATION: Motif

<400> SEQUENCE: 109

Gly Pro Glu Arg
1

<210> SEQ ID NO 110
<211> LENGTH: 4
<212> TYPE: PRT
<213> ORGANISM: Artificial Sequence
<220> FEATURE:
<223> OTHER INFORMATION: Motif

<400> SEQUENCE: 110

Gly Leu Glu Arg
1

<210> SEQ ID NO 111
<211> LENGTH: 4
<212> TYPE: PRT
<213> ORGANISM: Artificial Sequence
<220> FEATURE:
<223> OTHER INFORMATION: Motif

<400> SEQUENCE: 111

Glu Leu Glu Trp
1

<210> SEQ ID NO 112
<211> LENGTH: 5
<212> TYPE: PRT
<213> ORGANISM: Artificial Sequence
<220> FEATURE:
<223> OTHER INFORMATION: C-terminus

<400> SEQUENCE: 112

Val Thr Val Ser Ser
1 5

<210> SEQ ID NO 113
<211> LENGTH: 5
<212> TYPE: PRT
<213> ORGANISM: Artificial Sequence
<220> FEATURE:
<223> OTHER INFORMATION: C-terminus

<400> SEQUENCE: 113

Val Lys Val Ser Ser
1 5

<210> SEQ ID NO 114
<211> LENGTH: 5
<212> TYPE: PRT
<213> ORGANISM: Artificial Sequence
<220> FEATURE:
<223> OTHER INFORMATION: C-terminus

<400> SEQUENCE: 114

Val Gln Val Ser Ser
1 5

<210> SEQ ID NO 115
<211> LENGTH: 6
<212> TYPE: PRT
<213> ORGANISM: Artificial Sequence
<220> FEATURE:

<223> OTHER INFORMATION: C-terminus

<400> SEQUENCE: 115

Val Thr Val Ser Ser Ala
1 5

<210> SEQ ID NO 116
<211> LENGTH: 6
<212> TYPE: PRT
<213> ORGANISM: Artificial Sequence
<220> FEATURE:
<223> OTHER INFORMATION: C-terminus

<400> SEQUENCE: 116

Val Lys Val Ser Ser Ala
1 5

<210> SEQ ID NO 117
<211> LENGTH: 6
<212> TYPE: PRT
<213> ORGANISM: Artificial Sequence
<220> FEATURE:
<223> OTHER INFORMATION: C-terminus

<400> SEQUENCE: 117

Val Gln Val Ser Ser Ala
1 5

<210> SEQ ID NO 118
<211> LENGTH: 30
<212> TYPE: PRT
<213> ORGANISM: Artificial Sequence
<220> FEATURE:
<223> OTHER INFORMATION: FR1

<400> SEQUENCE: 118

Asp Val Gln Leu Val Glu Ser Gly Gly Gly Val Val Gln Pro Gly Gly
1 5 10 15

Ser Leu Arg Leu Ser Cys Thr Ala Ser Gly Phe Thr Phe Ser
20 25 30

<210> SEQ ID NO 119
<211> LENGTH: 30
<212> TYPE: PRT
<213> ORGANISM: Artificial Sequence
<220> FEATURE:
<223> OTHER INFORMATION: FR1

<400> SEQUENCE: 119

Glu Val Gln Leu Val Glu Ser Gly Gly Gly Val Val Gln Pro Gly Gly
1 5 10 15

Ser Leu Arg Leu Ser Cys Ala Ala Ser Gly Arg Ile Phe Ser
20 25 30

<210> SEQ ID NO 120
<211> LENGTH: 30
<212> TYPE: PRT
<213> ORGANISM: Artificial Sequence
<220> FEATURE:
<223> OTHER INFORMATION: FR1

<400> SEQUENCE: 120

Glu Val Gln Leu Val Glu Ser Gly Gly Gly Val Val Gln Pro Gly Gly
1 5 10 15

Ser Leu Arg Leu Ser Cys Ala Ala Ser Gly Phe Thr Phe Arg 20 25 30

<210> SEQ ID NO 121
<211> LENGTH: 30
<212> TYPE: PRT
<213> ORGANISM: Artificial Sequence
<220> FEATURE:
<223> OTHER INFORMATION: FR1

<400> SEQUENCE: 121

Glu Val Gln Leu Val Glu Ser Gly Gly Gly Val Val Gln Pro Gly Gly
1 5 10 15

Ser Leu Arg Leu Ser Cys Ala Ala Ser Gly Arg Thr Leu Ser
20 25 30

<210> SEQ ID NO 122
<211> LENGTH: 5
<212> TYPE: PRT
<213> ORGANISM: Artificial Sequence
<220> FEATURE:
<223> OTHER INFORMATION: CDR1

<400> SEQUENCE: 122

Thr Ala Asp Met Gly
1 5

<210> SEQ ID NO 123
<211> LENGTH: 14
<212> TYPE: PRT
<213> ORGANISM: Artificial Sequence
<220> FEATURE:
<223> OTHER INFORMATION: CDR1

<400> SEQUENCE: 123

Leu Pro Ala Ser Gly Asn Ile Phe Asn Leu Leu Thr Ile Ala
1 5 10

<210> SEQ ID NO 124
<211> LENGTH: 5
<212> TYPE: PRT
<213> ORGANISM: Artificial Sequence
<220> FEATURE:
<223> OTHER INFORMATION: CDR1

<400> SEQUENCE: 124

Ser Phe Gly Met Ser
1 5

<210> SEQ ID NO 125
<211> LENGTH: 5
<212> TYPE: PRT
<213> ORGANISM: Artificial Sequence
<220> FEATURE:
<223> OTHER INFORMATION: CDR1

<400> SEQUENCE: 125

Ser Tyr Ala Met Gly
1 5

<210> SEQ ID NO 126
<211> LENGTH: 14
<212> TYPE: PRT
<213> ORGANISM: Artificial Sequence
<220> FEATURE:
<223> OTHER INFORMATION: FR2

<400> SEQUENCE: 126

Trp Phe Arg Gln Ala Pro Gly Lys Gly Arg Glu Phe Val Ala
1 5 10

<210> SEQ ID NO 127
<211> LENGTH: 14
<212> TYPE: PRT
<213> ORGANISM: Artificial Sequence
<220> FEATURE:
<223> OTHER INFORMATION: FR2

<400> SEQUENCE: 127

Trp Tyr Arg Gln Ala Pro Gly Lys Gln Arg Glu Leu Val Ala
1 5 10

<210> SEQ ID NO 128
<211> LENGTH: 14
<212> TYPE: PRT
<213> ORGANISM: Artificial Sequence
<220> FEATURE:
<223> OTHER INFORMATION: FR2

<400> SEQUENCE: 128

Trp Val Arg Gln Ala Pro Gly Lys Gly Pro Glu Trp Val Ser
1 5 10

<210> SEQ ID NO 129
<211> LENGTH: 14
<212> TYPE: PRT
<213> ORGANISM: Artificial Sequence
<220> FEATURE:
<223> OTHER INFORMATION: FR2

<400> SEQUENCE: 129

Trp Phe Arg Gln Ala Pro Gly Lys Glu Arg Glu Phe Val Ala
1 5 10

<210> SEQ ID NO 130
<211> LENGTH: 17
<212> TYPE: PRT
<213> ORGANISM: Artificial Sequence
<220> FEATURE:
<223> OTHER INFORMATION: CDR2

<400> SEQUENCE: 130

Arg Ile Ser Gly Ile Asp Gly Thr Thr Tyr Tyr Asp Glu Pro Val Lys
1 5 10 15

Gly

<210> SEQ ID NO 131
<211> LENGTH: 16
<212> TYPE: PRT
<213> ORGANISM: Artificial Sequence
<220> FEATURE:
<223> OTHER INFORMATION: CDR2

<400> SEQUENCE: 131

Thr Ile Glu Ser Gly Ser Arg Thr Asn Tyr Ala Asp Ser Val Lys Gly
1 5 10 15

<210> SEQ ID NO 132
<211> LENGTH: 17
<212> TYPE: PRT
<213> ORGANISM: Artificial Sequence
<220> FEATURE:
<223> OTHER INFORMATION: CDR2

<400> SEQUENCE: 132

Ser Ile Ser Gly Ser Gly Ser Asp Thr Leu Tyr Ala Asp Ser Val Lys
1 5 10 15

Gly

<210> SEQ ID NO 133
<211> LENGTH: 17
<212> TYPE: PRT
<213> ORGANISM: Artificial Sequence
<220> FEATURE:
<223> OTHER INFORMATION: CDR2

<400> SEQUENCE: 133

Arg Ile Ser Gln Gly Gly Thr Ala Ile Tyr Tyr Ala Asp Ser Val Lys
1 5 10 15

Gly

<210> SEQ ID NO 134
<211> LENGTH: 32
<212> TYPE: PRT
<213> ORGANISM: Artificial Sequence
<220> FEATURE:
<223> OTHER INFORMATION: FR3

<400> SEQUENCE: 134

Arg Phe Thr Ile Ser Arg Asp Asn Ser Lys Asn Thr Val Tyr Leu Gln
1 5 10 15

Met Asn Ser Leu Arg Pro Glu Asp Thr Ala Leu Tyr Tyr Cys Arg Ser
20 25 30

<210> SEQ ID NO 135
<211> LENGTH: 32
<212> TYPE: PRT
<213> ORGANISM: Artificial Sequence
<220> FEATURE:
<223> OTHER INFORMATION: FR3

<400> SEQUENCE: 135

Arg Phe Thr Ile Ser Arg Asp Asn Ser Lys Lys Thr Val Tyr Leu Gln
1 5 10 15

Met Asn Ser Leu Arg Pro Glu Asp Thr Ala Leu Tyr Tyr Cys Gln Thr
20 25 30

<210> SEQ ID NO 136
<211> LENGTH: 32
<212> TYPE: PRT
<213> ORGANISM: Artificial Sequence
<220> FEATURE:
<223> OTHER INFORMATION: FR3

<400> SEQUENCE: 136

Arg Phe Thr Ile Ser Arg Asp Asn Ser Lys Asn Thr Leu Tyr Leu Gln
1 5 10 15

Met Asn Ser Leu Arg Pro Glu Asp Thr Ala Leu Tyr Tyr Cys Thr Ile
20 25 30

<210> SEQ ID NO 137
<211> LENGTH: 32
<212> TYPE: PRT
<213> ORGANISM: Artificial Sequence
<220> FEATURE:
<223> OTHER INFORMATION: FR3

<400> SEQUENCE: 137

Arg Phe Thr Ile Ser Arg Asp Asn Ser Lys Asn Thr Val Tyr Leu Gln
1 5 10 15

Met Asn Ser Leu Arg Pro Glu Asp Thr Ala Leu Tyr Tyr Cys Ala Lys
20 25 30

<210> SEQ ID NO 138
<211> LENGTH: 12
<212> TYPE: PRT
<213> ORGANISM: Artificial Sequence
<220> FEATURE:
<223> OTHER INFORMATION: CDR3

<400> SEQUENCE: 138

Pro Arg Tyr Ala Asp Gln Trp Ser Ala Tyr Asp Tyr
1 5 10

<210> SEQ ID NO 139
<211> LENGTH: 8
<212> TYPE: PRT
<213> ORGANISM: Artificial Sequence
<220> FEATURE:
<223> OTHER INFORMATION: CDR3

<400> SEQUENCE: 139

Ser Gly Ser Gly Ser Pro Asn Phe
1 5

<210> SEQ ID NO 140
<211> LENGTH: 6
<212> TYPE: PRT
<213> ORGANISM: Artificial Sequence
<220> FEATURE:
<223> OTHER INFORMATION: CDR3

<400> SEQUENCE: 140

Gly Gly Ser Leu Ser Arg
1 5

<210> SEQ ID NO 141
<211> LENGTH: 19
<212> TYPE: PRT
<213> ORGANISM: Artificial Sequence
<220> FEATURE:
<223> OTHER INFORMATION: CDR3

<400> SEQUENCE: 141

Asp Pro Ser Pro Tyr Tyr Arg Gly Ser Ala Tyr Leu Leu Ser Gly Ser
1 5 10 15

Tyr Asp Ser

<210> SEQ ID NO 142
<211> LENGTH: 11
<212> TYPE: PRT
<213> ORGANISM: Artificial Sequence
<220> FEATURE:
<223> OTHER INFORMATION: FR4

<400> SEQUENCE: 142

Trp Gly Gln Gly Thr Leu Val Thr Val Ser Ser
1 5 10

<210> SEQ ID NO 143
<211> LENGTH: 11
<212> TYPE: PRT
<213> ORGANISM: Artificial Sequence

<220> FEATURE:
<223> OTHER INFORMATION: FR4

<400> SEQUENCE: 143

Trp Gly Gln Gly Thr Leu Val Thr Val Ser Ser
1 5 10

<210> SEQ ID NO 144
<211> LENGTH: 11
<212> TYPE: PRT
<213> ORGANISM: Artificial Sequence
<220> FEATURE:
<223> OTHER INFORMATION: FR4

<400> SEQUENCE: 144

Ser Ser Gln Gly Thr Leu Val Thr Val Ser Ser
1 5 10

<210> SEQ ID NO 145
<211> LENGTH: 11
<212> TYPE: PRT
<213> ORGANISM: Artificial Sequence
<220> FEATURE:
<223> OTHER INFORMATION: FR4

<400> SEQUENCE: 145

Trp Gly Gln Gly Thr Leu Val Lys Val Ser Ser
1 5 10

<210> SEQ ID NO 146
<211> LENGTH: 5
<212> TYPE: PRT
<213> ORGANISM: Artificial Sequence
<220> FEATURE:
<223> OTHER INFORMATION: C-terminus

<400> SEQUENCE: 146

Val Thr Val Lys Ser
1 5

<210> SEQ ID NO 147
<211> LENGTH: 5
<212> TYPE: PRT
<213> ORGANISM: Artificial Sequence
<220> FEATURE:
<223> OTHER INFORMATION: C-terminus

<400> SEQUENCE: 147

Val Thr Val Gln Ser
1 5

<210> SEQ ID NO 148
<211> LENGTH: 5
<212> TYPE: PRT
<213> ORGANISM: Artificial Sequence
<220> FEATURE:
<223> OTHER INFORMATION: C-terminus

<400> SEQUENCE: 148

Val Lys Val Lys Ser
1 5

<210> SEQ ID NO 149
<211> LENGTH: 5
<212> TYPE: PRT
<213> ORGANISM: Artificial Sequence
<220> FEATURE:

<223> OTHER INFORMATION: C-terminus

<400> SEQUENCE: 149

Val Lys Val Gln Ser
1 5

<210> SEQ ID NO 150
<211> LENGTH: 5
<212> TYPE: PRT
<213> ORGANISM: Artificial Sequence
<220> FEATURE:
<223> OTHER INFORMATION: C-terminus

<400> SEQUENCE: 150

Val Gln Val Lys Ser
1 5

<210> SEQ ID NO 151
<211> LENGTH: 5
<212> TYPE: PRT
<213> ORGANISM: Artificial Sequence
<220> FEATURE:
<223> OTHER INFORMATION: C-terminus

<400> SEQUENCE: 151

Val Gln Val Gln Ser
1 5

<210> SEQ ID NO 152
<211> LENGTH: 6
<212> TYPE: PRT
<213> ORGANISM: Artificial Sequence
<220> FEATURE:
<223> OTHER INFORMATION: C-terminus

<400> SEQUENCE: 152

Val Thr Val Lys Ser Ala
1 5

<210> SEQ ID NO 153
<211> LENGTH: 6
<212> TYPE: PRT
<213> ORGANISM: Artificial Sequence
<220> FEATURE:
<223> OTHER INFORMATION: C-terminus

<400> SEQUENCE: 153

Val Thr Val Gln Ser Ala
1 5

<210> SEQ ID NO 154
<211> LENGTH: 6
<212> TYPE: PRT
<213> ORGANISM: Artificial Sequence
<220> FEATURE:
<223> OTHER INFORMATION: C-terminus

<400> SEQUENCE: 154

Val Lys Val Lys Ser Ala
1 5

<210> SEQ ID NO 155
<211> LENGTH: 6
<212> TYPE: PRT
<213> ORGANISM: Artificial Sequence
<220> FEATURE:
<223> OTHER INFORMATION: C-terminus

```
<400> SEQUENCE: 155

Val Lys Val Gln Ser Ala
1               5


<210> SEQ ID NO 156
<211> LENGTH: 6
<212> TYPE: PRT
<213> ORGANISM: Artificial Sequence
<220> FEATURE:
<223> OTHER INFORMATION: C-terminus

<400> SEQUENCE: 156

Val Gln Val Lys Ser Ala
1               5


<210> SEQ ID NO 157
<211> LENGTH: 6
<212> TYPE: PRT
<213> ORGANISM: Artificial Sequence
<220> FEATURE:
<223> OTHER INFORMATION: C-terminus

<400> SEQUENCE: 157

Val Gln Val Gln Ser Ala
1               5
```